(12) United States Patent
Slack et al.

(10) Patent No.: US 8,221,980 B2
(45) Date of Patent: Jul. 17, 2012

(54) GENETIC LESION ASSOCIATED WITH CANCER

(75) Inventors: Frank J. Slack, Branford, CT (US); Joanne B. Weidhaas, Westport, CT (US); Lena J. Chin, East Brunswick, NJ (US); Elena Ratner, Fairfield, CT (US)

(73) Assignee: Yale University, New Haven, CT (US)

( * ) Notice: Subject to any disclaimer, the term of this patent is extended or adjusted under 35 U.S.C. 154(b) by 6 days.

(21) Appl. No.: 12/683,827

(22) Filed: Jan. 7, 2010

(65) Prior Publication Data

US 2010/0173312 A1    Jul. 8, 2010

Related U.S. Application Data

(63) Continuation of application No. 12/600,013, filed as application No. PCT/US2008/065302 on May 30, 2008.

(60) Provisional application No. 61/124,610, filed on Apr. 18, 2008, provisional application No. 61/065,745, filed on Feb. 14, 2008, provisional application No. 61/001,965, filed on Nov. 5, 2007, provisional application No. 60/932,575, filed on May 31, 2007.

(51) Int. Cl.
*C12Q 1/68* (2006.01)

(52) U.S. Cl. .................. 435/6.11; 435/6.1; 435/6.14

(58) Field of Classification Search .................. None
See application file for complete search history.

(56) References Cited

FOREIGN PATENT DOCUMENTS
WO    2006/104289 A    10/2006

OTHER PUBLICATIONS

Kumar et al., "Impaired microRNA processing enhances cellular transformation and tumorigenesis," Nature Genetics, Apr. 2007, vol. 39, No. 5, pp. 673-677.*

Chen et al. "The second intron of the K-ras gene contains regulatory elements associated with mouse lung tumor susceptibility." Proceedings of the National Academy of Sciences of the United States of America. vol. 91, No. 4, pp. 1589-1593. 1994.
Johnson et al. "RAS is regulated by the let-7 microRNA family." Cell, Cell Press, Cambridge, MA, US. vol. 120, pp. 635-647. Mar. 11, 2005.
Lewis et al. "Prediction of Mammalian MicroRNA Targets." Cell, Cell Press, Cambridge, MA, US. vol. 115, No. 7, pp. 787-798. Dec. 26, 2003.
Loda, M.D. "Polymerase Chain Reaction-based methods for the detection of mutations in oncogenes and tumor suppressor genes." Human Pathology, Saunders, Philadelphia, PA, US. vol. 25, No. 6, pp. 564-571. Jun. 1, 1994.
Matzinger et al. "Tissue-specific expression of the K-ras allele from the A/J parent in (A/J x TSG-p53) F1 mice." Gene, Elsevier, Amsterdam, NL. vol. 188, No. 2, pp. 261-269. Apr. 1, 1997.
Weidhaas et al. "A microRNA binding site SNP acting as a marker of increased cancer risk." AACR Meeting Abstracts, Apr. 12, 2008.
Online Database EMBL; EBI; "BM975422." Retrieved from www.ebi.ac.uk. Accession No. BM975422. Feb. 24, 2003.
Online Database SNP; NCBI; Reference SNP (refSNP) Cluster Report: rs617764370. Retrieved from www.ncbi.nlm.nih.gov. Accession No. rs617764370. Dec. 12, 2007.
Halushka et al. "Patterns of Single-Nucleotide Polymorphisms in Candidate Genes for Blood-Pressure Homeostasis" *Nature* 22 (1999): 239-247.
Hirschhorn et al. "A Comprehensive Review of Genetic Association Studies" *Genetics in Medicine* 4.2 (2002): 45-61.
Ioannidis et al. "Replication Validity of Genetic Association Studies" *Nature Genetics* 29 (2001): 306-309.
Lucentini, J. "Gene Association Studies Typically Wrong: Reproducible Gene-disease Associations are Few and Far between" *The Scientist* 18 (2004): 20.
Wacholder et al. "Assessing the Probability that a Positive Report is False: An Approach for Molecular Epidemiology Studies" *J. Natl. Cancer Institute* 96.6 (2004): 434-442.

* cited by examiner

*Primary Examiner* — Young J Kim
(74) *Attorney, Agent, or Firm* — Mintz, Levin, Cohn, Ferris, Glovsky and Popeo, P.C.; Ivor Elrifi, Esq.; Katherine J. Miller

(57) ABSTRACT

The invention comprises methods for identifying mutations within the 3' UTRs of genes that lead to increased risk or probability of developing cancer.

6 Claims, 34 Drawing Sheets

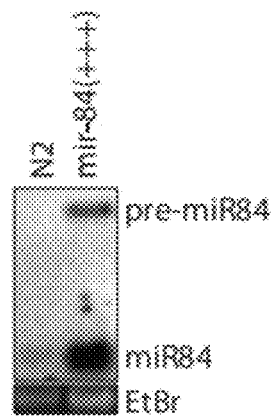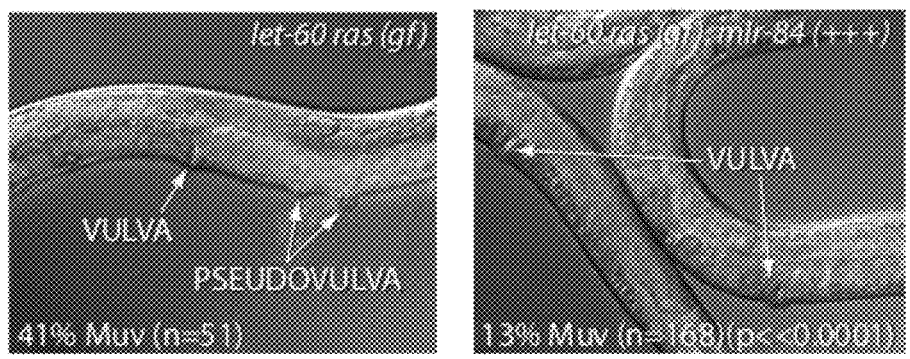
Fig. 7

*let-7* GENES MAP TO "FRAGILE REGIONS" ASSOCIATED WITH VARIOUS CANCERS

TABLE 2. EXAMPLES OF miRs LOCATED IN MINIMAL DELETED REGIONS, MINIMAL AMPLIFIED REGIONS, AND BREAKPOINT REGIONS INVOLVED IN HUMAN CANCERS

| CHROMOSOME | LOCATION (DEFINING MARKERS) | SIZE, Mb | miR | HISTOTYPE | KNOWN OG/TS |
|---|---|---|---|---|---|
| 3p21.1-21.2-D | ARP-D3R1 | 7 | let-7g/miR-135-1 | LUNG, BREAST CANCER | --- |
| 3p21.3(AP20)-D | GOLGA4-MLL | 0.75 | miR-26a | EPITHELIAL CANCER | --- |
| 3p23-21.31(MDR2)-D | D3S1788-D3S1767 | 12.32 | miR-26a, miR-138-1 | NASOPHARYNGEAL CANCER | --- |
| 5q32-D | ADRB2-ATX1 | 2.92 | miR-145, miR-143 | MYELODYSPLASTIC SYNDROME | --- |
| 9q22.3-D | D9S280-D9S1809 | 1.46 | miR-24-1/miR-27b/miR-23b; let-7a-1/let-7f-1/let-7d | UROTHELIAL CANCER | PTC, FANCC |
| 9q33-D | D9S1826-D9S158 | 0.4 | miR-123 | NSCLC | --- |
| 11q23-q24-D | D11S927-D11S1347 | 1.994 | miR-34a-1/mir-34a-2 | BREAST, LUNG CANCER | --- |
| 11q23-q24-D | D11S1345-D11S1328 | 1.725 | miR-125b-1/let-7a-2/miR-100 | BREAST, LUNG, OVARY, CERVIX CANCER | PPP2R1B |
| 13q14-D | D13S272-D13S25 | 0.54 | miR-15a/miR-16a | B-CLL | --- |
| 13q33-A | stSG1303-stSG31824 | 7.15 | miR-17/miR-18/miR-19a/miR-19b/miR-20/miR-106b-1/miR-92-1 | FOLLICULAR LYMPHOMA | --- |
| 17p13-D | D17S1866-D17S1574 | 1.899 | miR-22/miR-132/miR-212 | HCC | --- |
| 17p13-D | ENO3-TP53 | 2.275 | miR-195 | LUNG CANCER | TP53 |
| 17q22-q(8;17) | miR-142/c-MYC | --- | miR-142as/miR-142as | PROLYMPHOCYTIC LEUKEMIA | c-MYC |
| 17q23-A | CLTC-PPM1D | 0.97 | miR-21 | NEUROBLASTOMA | --- |
| 20q13-A | FLJ38732NF217 | 0.55 | miR-297-3 | COLON CANCER | --- |
| 21q11.1-D | D21S1911-ANA | 2.84 | miR-99a/let-7c/miR-125b | LUNG CANCER | --- |

D, DELETED REGION; A, AMPLIFIED REGION; NSCLC, NON-SMALL-CELL LUNG CANCER; HCC, HEPATOCELLULAR CARCINOMA; PTC, PATCHED HOMOLOG (DROSOPHILA); FANCC, FANCONI ANEMIA, COMPLEMENTATION GROUP C; PPP2R1B, PROTEIN PHOSPHATASE 2, REGULATORY SUBUNIT A (PR 65) β ISOFORM. miRs IN A CLUSTER ARE SEPARATED BY A SLASH. FOR REFERENCES, SEE TABLE 6.

LCS6      GAUUCACCCACCUUGGCCUCA
VARIANT LCS6   GAUGCACCCACCUUGGCCUCA

|  | PRIMARY LUNG TUMOR/ADJACENT NON-TUMOR TISSUE | PRIMARY LUNG TUMOR |
|---|---|---|
| LCS6 4th bp = T | 35 | 24 |
| 4th bp = T/G | 8* | 6 |
| 4th bp = G/G | 0 | 1 |
| TOTAL PATIENTS | 43 | 31 | let-7s AND LCS6 OR VARIANT LCS6 mfe VALUE (kcal/mol)

|        | LCS6  | alt LCS6 | Δ mfe |
|--------|-------|----------|-------|
| let-7a | -18.7 | -22.9    | -4.2  |
| let-7b | -23.3 | -24.5    | -1.2  |
| let-7c | -20.3 | -22.9    | -2.6  |
| let-7d | -18.5 | -24.7    | -6.2  |
| let-7e | -19.4 | -23.9    | -4.5  |
| let-7f | -14.2 | -16.8    | -2.6  |
| let-7g | -14.1 | -15.4    | -1.3  |
| let-7i | -15.7 | -19.8    | -4.1  |

Fig. 24

SEQUENCE LISTING

<160> NUMBER OF SEQ ID NOS: 94

<210> SEQ ID NO 1
<211> LENGTH: 25
<212> TYPE: RNA
<213> ORGANISM: Homo sapiens

<400> SEQUENCE: 1
aguucucaga auaacuaccu ccuca                                         25

<210> SEQ ID NO 2
<211> LENGTH: 26
<212> TYPE: RNA
<213> ORGANISM: Homo sapiens

<400> SEQUENCE: 2
ggcugucuga ccagagaaug caccuc                                        26

<210> SEQ ID NO 3
<211> LENGTH: 18
<212> TYPE: RNA
<213> ORGANISM: Homo sapiens

<400> SEQUENCE: 3
acagcacaaa cacaccuc                                                 18

<210> SEQ ID NO 4
<211> LENGTH: 28
<212> TYPE: RNA
<213> ORGANISM: Homo sapiens

<400> SEQUENCE: 4
agcugugauc agugauuuuc aaaccyca                                      28

<210> SEQ ID NO 5
<211> LENGTH: 32
<212> TYPE: RNA
<213> ORGANISM: Homo sapiens

<400> SEQUENCE: 5
aauugccuuc aaucccuuc ucaccccacc uc                                  32

<210> SEQ ID NO 6
<211> LENGTH: 24
<212> TYPE: RNA
<213> ORGANISM: Homo sapiens

<400> SEQUENCE: 6
aucuaaauac uuacugaggu ccuc                                          24

<210> SEQ ID NO 7
<211> LENGTH: 25
<212> TYPE: RNA
<213> ORGANISM: Homo sapiens

<400> SEQUENCE: 7
aauuuuccug aggcuuauca ccuca                                         25

<210> SEQ ID NO 8
<211> LENGTH: 30
<212> TYPE: RNA
<213> ORGANISM: Homo sapiens

```
<400> SEQUENCE: 8
gauugcugaa aagaauucua guuuaccuca                                    30

<210> SEQ ID NO 9
<211> LENGTH: 19
<212> TYPE: RNA
<213> ORGANISM: Homo sapiens

<400> SEQUENCE: 9
aacaggaacu auuggccuc                                                19

<210> SEQ ID NO 10
<211> LENGTH: 25
<212> TYPE: RNA
<213> ORGANISM: Homo sapiens

<400> SEQUENCE: 10
gacaguggaa guuuuuuuu ccucg                                          25

<210> SEQ ID NO 11
<211> LENGTH: 19
<212> TYPE: RNA
<213> ORGANISM: Homo sapiens

<400> SEQUENCE: 11
auuaguguca ucuugccuc                                                19

<210> SEQ ID NO 12
<211> LENGTH: 25
<212> TYPE: RNA
<213> ORGANISM: Homo sapiens

<400> SEQUENCE: 12
aaugcccuac aucuuauuuu ccuca                                         25

<210> SEQ ID NO 13
<211> LENGTH: 24
<212> TYPE: RNA
<213> ORGANISM: Homo sapiens

<400> SEQUENCE: 13
gguucaagcg auucucgugc cucg                                          24

<210> SEQ ID NO 14
<211> LENGTH: 24
<212> TYPE: RNA
<213> ORGANISM: Homo sapiens

<400> SEQUENCE: 14
ggcugguccg aacuccugac cuca                                          24

<210> SEQ ID NO 15
<211> LENGTH: 21
<212> TYPE: RNA
<213> ORGANISM: Homo sapiens

<400> SEQUENCE: 15
gauucaccca ccuuggccuc a                                             21

<210> SEQ ID NO 16
<211> LENGTH: 28
<212> TYPE: RNA
<213> ORGANISM: Homo sapiens
```

```
<400> SEQUENCE: 16
ggguguuaag acuugacaca guaccucg                                        28

<210> SEQ ID NO 17
<211> LENGTH: 28
<212> TYPE: RNA
<213> ORGANISM: Homo sapiens

<400> SEQUENCE: 17
agugcuuaug aggggauauu uaggccuc                                        28

<210> SEQ ID NO 18
<211> LENGTH: 30
<212> TYPE: RNA
<213> ORGANISM: Homo sapiens

<400> SEQUENCE: 18
gaccgugggc cgaggugacu gcagacccuc                                      30

<210> SEQ ID NO 19
<211> LENGTH: 25
<212> TYPE: RNA
<213> ORGANISM: Homo sapiens

<400> SEQUENCE: 19
ggaaccccag cccuuagcuc cccuc                                           25

<210> SEQ ID NO 20
<211> LENGTH: 26
<212> TYPE: RNA
<213> ORGANISM: Homo sapiens

<400> SEQUENCE: 20
agcccuuagc uccccuccca ggccuc                                          26

<210> SEQ ID NO 21
<211> LENGTH: 21
<212> TYPE: RNA
<213> ORGANISM: Homo sapiens

<400> SEQUENCE: 21
gaugcaccca ccuuggccuc a                                               21

<210> SEQ ID NO 22
<211> LENGTH: 1061
<212> TYPE: DNA
<213> ORGANISM: Homo sapiens

<400> SEQUENCE: 22
tgccctgcgc ccgcaacccg agccgcaccc gccgcggacg agcccatgc gcggggcgaa      60 ccgcgcgccc ccgccccgc cccgcccgg cctcggcccc ggcccggcc ccggggcag        120 tcgcgcctgt gaacggtggg gcaggagacc ctgtaggagg accccgggcc gcaggcccct    180
gaggagcgat gacggaatat aagctggtgg tggtgggcgc cggcggtgtg ggcaagagtg    240
cgctgaccat ccagctgatc cagaaccatt ttgtggacga atacgacccc actatagagg    300
attcctaccg gaagcaggtg gtcattgatg gggagacgtg cctgttggac atcctggata    360
ccgccggcca ggaggagtac agcgccatgc gggaccagta catgcgcacc ggggagggct    420
tcctgtgtgt gtttgccatc aacaacacca agtcttttga ggacatccac cagtacaggg    480
agcagatcaa acgggtgaag gactcggatg acgtgcccat ggtgctggtg gggaacaagt    540
```

```
gtgacctggc tgcacgcact gtggaatctc ggcaggctca ggacctcgcc cgaagctacg    600
gcatccccta catcgagacc tcggccaaga cccggcaggg agtggaggat gccttctaca    660
cgttggtgcg tgagatccgg cagcacaagc tgcggaagct gaaccctcct gatgagagtg    720 gccccgctg catgagctgc aagtgtgtgc tctcctgacg cagcacaagc tcaggacatg     780
gaggtgccgg atgcaggaag gaggtgcaga cggaaggagg aggaaggaag gacggaagca    840
aggaaggaag gaagggctgc tggagcccag tcaccccggg accgtgggcc gaggtgactg    900
cagaccctcc cagggaggct gtgcacagac tgtcttgaac atcccaaatg ccaccggaac    960
cccagccctt agctcccctc ccaggcctct gtgggccctt gtcgggcaca gatgggatca   1020
cagtaaatta ttggatggtc ttgaaaaaaa aaaaaaaaa a                        1061

<210> SEQ ID NO 23
<211> LENGTH: 1143
<212> TYPE: DNA
<213> ORGANISM: Homo sapiens

<400> SEQUENCE: 23
tgccctgcgc ccgcaacccg agccgcaccc gccgcggacg gagcccatgc gcggggcgaa     60
ccgcgcgccc ccgccccgc cccgcccgg cctcggcccc ggccctggcc ccgggggcag     120
tcgcgcctgt gaacggtggg gcaggagacc ctgtaggagg accccgggcc gcaggccct    180 gaggagcgat gacggaatat aagctggtgg tggtgggcgc cggcggtgtg ggcaagagtg    240
cgctgaccat ccagctgatc cagaaccatt ttgtggacga atacgacccc actatagagg    300
attcctaccg gaagcaggtg gtcattgatg gggagacgtg cctgttggac atcctggata    360
ccgccggcca ggaggagtac agcgccatgc gggaccagta catgcgcacc ggggagggct    420
tcctgtgtgt gtttgccatc aacaacacca agtcttttga ggacatccac cagtacaggg    480
agcagatcaa acgggtgaag gactcggatg acgtgcccat ggtgctggtg gggaacaagt    540
gtgacctggc tgcacgcact gtggaatctc ggcaggctca ggacctcgcc cgaagctacg    600
gcatccccta catcgagacc tcggccaaga cccggcaggg cagccgctct ggctctagct    660
ccagctccgg gaccctctgg accccccgg gacccatgtg acccagcggc ccctcgcgct    720
ggagtggagg atgccttcta cacgttggtg cgtgagatcc ggcagcacaa gctgcggaag    780
ctgaaccctc tgatgagag tggccccggc tgcatgagct gcaagtgtgt gctctcctga    840
cgcagcacaa gctcaggaca tggaggtgcc ggatgcagga aggaggtgca gacggaagga    900
ggaggaagga aggacggaag caaggaagga aggaagggct gctggagccc agtcaccccg    960
ggaccgtggg ccgaggtgac tgcagaccct cccagggagg ctgtgcacag actgtcttga   1020
acatcccaaa tgccaccgga accccagccc ttagctcccc tcccaggcct ctgtgggccc   1080
ttgtcgggca cagatgggat cacagtaaat tattggatgg tcttgaaaaa aaaaaaaaaa   1140
aaa                                                                1143

<210> SEQ ID NO 24
<211> LENGTH: 5436
<212> TYPE: DNA
<213> ORGANISM: Homo sapiens

<400> SEQUENCE: 24
ggccgcggcg gcggaggcag cagcggcggc ggcagtggcg gcggcgaagg tggcggcggc     60
tcggccagta ctcccggccc ccgccatttc ggactgggag cgagcgcggc gcaggcactg    120
aaggcggcgg cggggccaga ggctcagcgg ctcccaggtg cgggagagag gcctgctgaa    180
```

```
aatgactgaa tataaacttg tggtagttgg agctggtggc gtaggcaaga gtgccttgac    240
gatacagcta attcagaatc attttgtgga cgaatatgat ccaacaatag aggattccta    300
caggaagcaa gtagtaattg atggagaaac ctgtctcttg gatattctcg acacagcagg    360
tcaagaggag tacagtgcaa tgagggacca gtacatgagg actggggagg gctttctttg    420
tgtatttgcc ataaataata ctaaatcatt tgaagatatt caccattata gagaacaaat    480
taaaagagtt aaggactctg aagatgtacc tatggtccta gtaggaaata aatgtgattt    540
gccttctaga acagtagaca caaaacaggc tcaggactta gcaagaagtt atggaattcc    600
ttttattgaa acatcagcaa agacaagaca gagagtggag gatgcttttt atacattggt    660
gagggagatc cgacaataca gattgaaaaa aatcagcaaa gaagaaaaga ctcctggctg    720
tgtgaaaatt aaaaaatgca ttataatgta atctgggtgt tgatgatgcc ttctatacat    780
tagttcgaga aattcgaaaa cataaagaaa agatgagcaa agatggtaaa aagaagaaaa    840
agaagtcaaa gacaaagtgt gtaattatgt aaatacaatt tgtacttttt tcttaaggca    900
tactagtaca agtggtaatt tttgtacatt acactaaatt attagcattt gttttagcat    960
tacctaattt ttttcctgct ccatgcagac tgttagcttt taccttaaat gcttatttta   1020
aaatgacagt ggaagttttt ttttcctcta agtgccagta ttcccagagt tttggttttt   1080
gaactagcaa tgcctgtgaa aaagaaactg aatacctaag atttctgtct tggggttttt   1140
ggtgcatgca gttgattact tcttattttt cttaccaatt gtgaatgttg gtgtgaaaca   1200
aattaatgaa gcttttgaat catccctatt ctgtgtttta tctagtcaca taaatggatt   1260
aattactaat ttcagttgag accttctaat tggtttttac tgaaacattg agggaacaca   1320
aatttatggg cttcctgatg atgattcttc taggcatcat gtcctatagt ttgtcatccc   1380
tgatgaatgt aaagttacac tgttcacaaa ggttttgtct cctttccact gctattagtc   1440
atggtcactc tccccaaaat attatatttt ttctataaaa agaaaaaaat ggaaaaaaat   1500
tacaaggcaa tggaaactat tataaggcca tttcctttto acattagata aattactata   1560
aagactccta atagcttttc ctgttaaggc agacccagta tgaaatgggg attattatag   1620
caaccatttt ggggctatat ttacatgcta ctaaattttt ataataattg aaaagatttt   1680
aacaagtata aaaaattctc ataggaatta aatgtagtct ccctgtgtca gactgctctt   1740
tcatagtata actttaaatc ttttcttcaa cttgagtctt tgaagatagt tttaattctg   1800
cttgtgacat taaaagatta tttgggccag ttatagctta ttaggtgttg aagagaccaa   1860
ggttgcaagg ccaggccctg tgtgaacctt tgagctttca tagagagttt cacagcatgg   1920
actgtgtccc cacggtcatc cagtgttgtc atgcattggt tagtcaaaat ggggagggac   1980
tagggcagtt tggatagctc aacaagatac aatctcactc tgtggtggtc ctgctgacaa   2040
atcaagagca ttgcttttgt ttcttaagaa aacaaactct tttttaaaaa ttacttttaa   2100
atattaactc aaaagttgag attttggggt ggtggtgtgc caagacatta atttttttt    2160
taaacaatga agtgaaaaag ttttacaatc tctaggtttg gctagttctc ttaacactgg   2220
ttaaattaac attgcataaa cactttttcaa gtctgatcca tatttaataa tgctttaaaa   2280
taaaaataaa aacaatcctt tgataaaatt taaaatgtta cttattttaa aataaatgaa   2340
gtgagatggc atggtgaggt gaaagtatca ctggactagg aagaaggtga cttaggttct   2400
agataggtgt cttttaggac tctgattttg aggacatcac ttactatcca tttcttcatg   2460
ttaaaagaag tcatctcaaa ctcttagttt ttttttttta caactatgta atttatattc   2520
catttacata aggatacact tatttgtcaa gctcagcaca atctgtaaat ttttaaccta   2580
```

```
tgttacacca tcttcagtgc cagtcttggg caaaattgtg caagaggtga agtttatatt    2640
tgaatatcca ttctcgtttt aggactcttc ttccatatta gtgtcatctt gcctccctac    2700
cttccacatg ccccatgact tgatgcagtt ttaatacttg taattcccct aaccataaga    2760
tttactgctg ctgtggatat ctccatgaag ttttcccact gagtcacatc agaaatgccc    2820
tacatcttat ttcctcaggg ctcaagagaa tctgacagat accataaagg gatttgacct    2880
aatcactaat tttcaggtgg tggctgatgc tttgaacatc tctttgctgc ccaatccatt    2940
agcgacagta ggatttttca aacctggtat gaatagacag aaccctatcc agtggaagga    3000
gaatttaata aagatagtgc tgaaagaatt ccttaggtaa tctataacta ggactactcc    3060
tggtaacagt aatacattcc attgttttag taaccagaaa tcttcatgca atgaaaaata    3120
ctttaattca tgaagcttac tttttttttt tggtgtcaga gtctcgctct tgtcacccag    3180
gctggaatgc agtggcgcca tctcagctca ctgcaacctc catctcccag gttcaagcga    3240
ttctcgtgcc tcggcctcct gagtagctgg gattacaggc gtgtgccact acactcaact    3300 aattttgta ttttaggag agacggggtt tcaccctgtt ggccaggctg gtctcgaact    3360
cctgacctca gtgattcac ccaccttggc ctcataaacc tgttttgcag aactcattta    3420
ttcagcaaat atttattgag tgcctaccag atgccagtca ccgcacaagg cactgggtat    3480
atggtatccc caaacaagag acataatccc ggtccttagg tagtgctagt gtggtctgta    3540
atatcttact aaggcctttg gtatacgacc cagagataac acgatgcgta ttttagtttt    3600
gcaaagaagg ggtttggtct ctgtgccagc tctataattg ttttgctacg attccactga    3660
aactcttcga tcaagctact ttatgtaaat cacttcattg ttttaaagga ataaacttga    3720
ttatattgtt tttttatttg gcataactgt gattcttta ggacaattac tgtacacatt    3780
aaggtgtatg tcagatattc atattgaccc aaatgtgtaa tattccagtt ttctctgcat    3840
aagtaattaa aatatactta aaaattaata gttttatctg ggtacaaata aacaggtgcc    3900
tgaactagtt cacagacaag gaaacttcta tgtaaaaatc actatgattt ctgaattgct    3960
atgtgaaact acagatcttt ggaacactgt ttaggtaggg tgttaagact tacacagtac    4020
ctcgtttcta cacagagaaa gaaatggcca tacttcagga actgcagtgc ttatgagggg    4080
atatttaggc ctcttgaatt tttgatgtag atgggcattt ttttaaggta gtggttaatt    4140
acctttatgt gaactttgaa tggtttaaca aaagattgt ttttgtagag attttaaagg    4200
gggagaattc tagaaataaa tgttacctaa ttattacagc cttaaagaca aaaatccttg    4260
ttgaagtttt tttaaaaaaa gctaaattac atagacttag gcattaacat gtttgtggaa    4320
gaatatagca gacgtatatt gtatcatttg agtgaatgtt cccaagtagg cattctaggc    4380
tctatttaac tgagtcacac tgcataggaa tttagaacct aacttttata ggttatcaaa    4440
actgttgtca ccattgcaca attttgtcct aatatataca tagaaacttt gtggggcatg    4500
ttaagttaca gtttgcacaa gttcatctca tttgtattcc attgattttt tttttcttct    4560
aaacattttt tcttcaaaca gtatataact tttttttaggg gatttttttt tagacagcaa    4620
aaactatctg aagatttcca tttgtcaaaa agtaatgatt tcttgataat tgtgtagtaa    4680
tgttttttag aacccagcag ttaccttaaa gctgaattta tatttagtaa cttctgtgtt    4740
aatactggat agcatgaatt ctgcattgag aaactgaata gctgtcataa aatgaaactt    4800
tctttctaaa gaaagatact cacatgagtt cttgaagaat agtcataact agattaagat    4860
ctgtgtttta gtttaatagt ttgaagtgcc tgttttggat aatgataggt aatttagatg    4920
aatttagggg aaaaaaaagt tatctgcaga tatgttgagg gcccatctct cccccacac    4980
```

| | | | | |
|---|---|---|---|---|
| ccccacagag | ctaactgggt | tacagtgttt | tatccgaaag | tttccaattc | cactgtcttg | 5040 |
| tgttttcatg | ttgaaaatac | ttttgcattt | ttccttt gag | tgccaatttc | ttactagtac | 5100 |
| tatttcttaa | tgtaacatgt | ttacctggaa | tgtattttaa | ctattttt gt | atagtgtaaa | 5160 |
| ctgaaacatg | cacattttgt | acattgtgct | ttcttttgtg | ggacatatgc | agtgtgatcc | 5220 |
| agttgttttc | catcatttgg | ttgcgctgac | ctaggaatgt | tggtcatatc | aaacattaaa | 5280 |
| aatgaccact | cttttaattg | aaattaactt | ttaaatgttt | ataggagtat | gtgctgtgaa | 5340 |
| gtgatctaaa | atttgtaata | ttttt gtcat | gaactgtact | actcctaatt | attgtaatgt | 5400 |
| aataaaaata | gttacagtga | caaaaaaaaa | aaaaaa | | | 5436 |

<210> SEQ ID NO 25
<211> LENGTH: 5312
<212> TYPE: DNA
<213> ORGANISM: Homo sapiens

<400> SEQUENCE: 25

| | | | | | | |
|---|---|---|---|---|---|---|
| ggccgcggcg | gcggaggcag | cagcggcggc | ggcagtggcg | gcggcgaagg | tggcggcggc | 60 |
| tcggccagta | ctcccggccc | ccgccatttc | ggactgggag | cgagcgcggc | gcaggcactg | 120 |
| aaggcggcgg | cggggccaga | ggctcagcgg | ctcccaggtg | cgggagagag | gcctgctgaa | 180 |
| aatgactgaa | tataaacttg | tggtagttgg | agctggtggc | gtaggcaaga | gtgccttgac | 240 |
| gatacagcta | attcagaatc | attttgtgga | cgaatatgat | ccaacaatag | aggattccta | 300 |
| caggaagcaa | gtagtaattg | atggagaaac | ctgtctcttg | gatattctcg | acacagcagg | 360 |
| tcaagaggag | tacagtgcaa | tgagggacca | gtacatgagg | actggggagg | gctttctttg | 420 |
| tgtatttgcc | ataaataata | ctaaatcatt | tgaagatatt | caccattata | gagaacaaat | 480 |
| taaaagagtt | aaggactctg | aagatgtacc | tatggtccta | gtaggaaata | atgtgattt | 540 |
| gccttctaga | acagtagaca | caaaacaggc | tcaggactta | gcaagaagtt | atggaattcc | 600 |
| ttttattgaa | acatcagcaa | agacaagaca | gggtgttgat | gatgccttct | atacattagt | 660 |
| tcgagaaatt | cgaaaacata | agaaaagat | gagcaaagat | ggtaaaaaga | agaaaaagaa | 720 |
| gtcaaagaca | aagtgtgtaa | ttatgtaaat | acaatttgta | cttttttctt | aaggcatact | 780 |
| agtacaagtg | gtaattttt g | tacattacac | taaattatta | gcatttgttt | tagcattacc | 840 |
| taattttttt | cctgctccat | gcagactgtt | agcttttacc | ttaaatgctt | attttaaaat | 900 |
| gacagtggaa | gttttttttt | cctctaagtg | ccagtattcc | cagagttttg | gttttt gaac | 960 |
| tagcaatgcc | tgtgaaaaag | aaactgaata | cctaagattt | ctgtcttggg | gttttt ggtg | 1020 |
| catgcagttg | attacttctt | attttttctta | ccaattgtga | atgttggtgt | gaaacaaatt | 1080 |
| aatgaagctt | ttgaatcatc | cctattctgt | gttttatcta | gtcacataaa | tggattaatt | 1140 |
| actaatttca | gttgagacct | tctaattggt | ttttactgaa | acattgaggg | aacacaaatt | 1200 |
| tatgggcttc | ctgatgatga | ttcttctagg | catcatgtcc | tatagtttgt | catccctgat | 1260 |
| gaatgtaaag | ttacactgtt | cacaaaggtt | ttgtctcctt | tccactgcta | ttagtcatgg | 1320 |
| tcactctccc | caaatatta | tatttttttct | ataaaagaa | aaaatgaa | aaaaattaca | 1380 |
| aggcaatgga | aactattata | aggccatttc | cttttcacat | tagataaatt | actataaaga | 1440 |
| ctcctaatag | cttttcctgt | taaggcagac | ccagtatgaa | atggggatta | ttatagcaac | 1500 |
| cattttgggg | ctatatttac | atgctactaa | attttttataa | taattgaaaa | gattttaaca | 1560 |
| agtataaaaa | attctcatag | gaattaaatg | tagtctccct | gtgtcagact | gctctttcat | 1620 |
| agtataactt | taaatctttt | cttcaacttg | agtctttgaa | gatagttttta | attctgcttg | 1680 |

```
tgacattaaa agattatttg ggccagttat agcttattag gtgttgaaga gaccaaggtt      1740
gcaaggccag gccctgtgtg aacctttgag ctttcataga gagtttcaca gcatggactg      1800
tgtccccacg gtcatccagt gttgtcatgc attggttagt caaaatgggg agggactagg      1860
gcagtttgga tagctcaaca agatacaatc tcactctgtg gtggtcctgc tgacaaatca      1920
agagcattgc ttttgtttct taagaaaaca aactcttttt taaaaattac ttttaaatat      1980
taactcaaaa gttgagattt tggggtggtg gtgtgccaag acattaattt ttttttttaaa     2040 caatgaagtg aaaaagtttt acaatctcta ggtttggcta gttctcttaa cactggttaa      2100
attaacattg cataaacact tttcaagtct gatccatatt taataatgct ttaaaataaa      2160
aataaaaaca atccttttga taaatttaaa atgttactta ttttaaaata aatgaagtga      2220
gatggcatgg tgaggtgaaa gtatcactgg actaggaaga aggtgactta ggttctagat      2280
aggtgtcttt taggactctg attttgagga catcacttac tatccatttc ttcatgttaa      2340
aagaagtcat ctcaaactct tagttttttt ttttttacaac tatgtaattt atattccatt     2400
tacataagga tacacttatt tgtcaagctc agcacaatct gtaaattttt aacctatgtt      2460
acaccatctt cagtgccagt cttgggcaaa attgtgcaag aggtgaagtt tatatttgaa      2520
tatccattct cgttttagga ctcttcttcc atattagtgt catcttgcct ccctaccttc      2580
cacatgcccc atgacttgat gcagttttaa tacttgtaat tccctaacc ataagattta       2640 ctgctgctgt ggatatctcc atgaagtttt cccactgagt cacatcagaa atgccctaca      2700
tcttatttcc tcagggctca agagaatctg acagatacca taagggggatt tgacctaatc     2760 actaattttc aggtggtggc tgatgctttg aacatctctt tgctgcccaa tccattagcg      2820
acagtaggat ttttcaaacc tggtatgaat agacagaacc ctatccagtg aaggagaat       2880 ttaataaaga tagtgctgaa agaattcctt aggtaatcta taactaggac tactcctggt      2940
aacagtaata cattccattg ttttagtaac cagaaatctt catgcaatga aaaatacttt      3000
aattcatgaa gcttactttt tttttttggt gtcagagtct cgctcttgtc acccaggctg      3060
gaatgcagtg gcgccatctc agctcactgc aacctccatc tcccaggttc aagcgattct      3120
cgtgcctcgg cctcctgagt agctgggatt acaggcgtgt gccactacac tcaactaatt      3180
tttgtatttt taggagagac ggggtttcac cctgttggcc aggctggtct cgaactcctg      3240
acctcaagtg attcacccac cttggcctca taaacctgtt ttgcagaact catttattca      3300
gcaaatattt attgagtgcc taccagatgc cagtcaccgc acaaggcact gggtatatgg      3360
tatccccaaa caagagacat aatcccggtc cttaggtagt gctagtgtgg tctgtaatat      3420
cttactaagg cctttggtat acgacccaga gataacacga tgcgtatttt agttttgcaa      3480 agaagggggtt tggtctctgt gccagctcta taattgtttt gctacgattc cactgaaact     3540
cttcgatcaa gctactttat gtaaatcact tcattgttt aaaggaataa acttgattat       3600
attgtttttt tatttggcat aactgtgatt cttttaggac aattactgta cacattaagg      3660
tgtatgtcag atattcatat tgacccaaat gtgtaatatt ccagttttct ctgcataagt      3720
aattaaaata tacttaaaaa ttaatagttt tatctgggta caaataaaca ggtgcctgaa      3780
ctagttcaca gacaaggaaa cttctatgta aaaatcacta tgatttctga attgctatgt      3840
gaaactacag atcttttggaa cactgtttag gtagggtgt aagacttaca cagtacctcg      3900
tttctacaca gagaaagaaa tggccatact tcaggaactg cagtgcttat gagggatat       3960 ttaggcctct tgaattttg atgtagatgg gcattttttt aaggtagtgg ttaattacct       4020
ttatgtgaac tttgaatggt ttaacaaaag atttgttttt gtagagattt taaagggggga     4080
```

```
gaattctaga aataaatgtt acctaattat tacagcctta aagacaaaaa tccttgttga    4140
agttttttta aaaaaagcta aattacatag acttaggcat taacatgttt gtggaagaat    4200
atagcagacg tatattgtat catttgagtg aatgttccca agtaggcatt ctaggctcta    4260
tttaactgag tcacactgca taggaattta gaacctaact tttataggtt atcaaaactg    4320
ttgtcaccat tgcacaattt tgtcctaata tatacataga aactttgtgg ggcatgttaa    4380
gttacagttt gcacaagttc atctcatttg tattccattg atttttttt tcttctaaac    4440 atttttcctt caaacagtat ataactttt ttagggatt ttttttaga cagcaaaaac      4500 tatctgaaga tttccatttg tcaaaaagta atgatttctt gataattgtg tagtaatgtt    4560
ttttagaacc cagcagttac cttaaagctg aatttatatt tagtaacttc tgtgttaata    4620
ctggatagca tgaattctgc attgagaaac tgaatagctg tcataaaatg aaactttctt    4680
tctaaagaaa gatactcaca tgagttcttg aagaatagtc ataactagat taagatctgt    4740
gttttagttt aatagtttga agtgcctgtt tgggataatg ataggtaatt tagatgaatt    4800
taggggaaaa aaaagttatc tgcagatatg ttgagggccc atctctcccc ccacaccccc    4860
acagagctaa ctgggttaca gtgtttatc cgaaagtttc caattccact gtcttgtgtt     4920
ttcatgttga aaatactttt gcattttcc tttgagtgcc aatttcttac tagtactatt     4980
tcttaatgta acatgtttac ctggaatgta ttttaactat ttttgtatag tgtaaactga    5040
aacatgcaca ttttgtacat tgtgctttct tttgtgggac atatgcagtg tgatccagtt    5100
gttttccatc atttggttgc gctgacctag gaatgttggt catatcaaac attaaaaatg    5160
accactcttt taattgaaat taacttttaa atgtttatag gagtatgtgc tgtgaagtga    5220
tctaaaattt gtaatatttt tgtcatgaac tgtactactc ctaattattg taatgtaata    5280
aaaatagtta cagtgacaaa aaaaaaaaaa aa                                  5312
```

<210> SEQ ID NO 26
<211> LENGTH: 5436
<212> TYPE: DNA
<213> ORGANISM: Homo sapiens

<400> SEQUENCE: 26

```
ggccgcggcg gcggaggcag cagcggcggc ggcagtggcg gcggcgaagg tggcggcggc      60
tcggccagta ctcccggccc ccgccatttc ggactgggag cgagcgcggc gcaggcactg     120
aaggcggcgg cggggccaga ggctcagcgg ctcccaggtg cgggagagag gcctgctgaa     180
aatgactgaa tataaacttg tggtagttgg agctggtggc gtaggcaaga gtgccttgac     240
gatacagcta attcagaatc attttgtgga cgaatatgat ccaacaatag aggattccta    300
caggaagcaa gtagtaattg atggagaaac ctgtctcttg gatattctcg acacagcagg    360
tcaagaggag tacagtgcaa tgagggacca gtacatgagg actggggagg gctttctttg    420
tgtatttgcc ataaataata ctaaatcatt tgaagatatt caccattata gagaacaaat    480
taaaagagtt aaggactctg aagatgtacc tatggtccta gtaggaaata atgtgatttt    540
gccttctaga acagtagaca caaaacaggc tcaggactta gcaagaagtt atggaattcc    600
ttttattgaa acatcagcaa agacaagaca gagagtggag gatgcttttt atacattggt    660
gagggagatc cgacaataca gattgaaaaa aatcagcaaa gaagaaaaga ctcctggctg    720
tgtgaaaatt aaaaaaatgca ttataatgta atctgggtgt tgatgatgcc ttctatacat    780
tagttcgaga aattcgaaaa cataaagaaa agatgagcaa agatggtaaa aagaagaaaa    840
agaagtcaaa gacaaagtgt gtaattatgt aaatacaatt tgtactttttt tcttaaggca   900
```

```
tactagtaca agtggtaatt tttgtacatt acactaaatt attagcattt gttttagcat    960
tacctaattt ttttcctgct ccatgcagac tgttagcttt taccttaaat gcttatttta   1020
aaatgacagt ggaagttttt ttttcctcta agtgccagta ttcccagagt tttggttttt   1080
gaactagcaa tgcctgtgaa aaagaaactg aatacctaag atttctgtct tggggttttt   1140
ggtgcatgca gttgattact tcttattttt cttaccaatt gtgaatgttg gtgtgaaaca   1200
aattaatgaa gcttttgaat catccctatt ctgtgtttta tctagtcaca taaatggatt   1260
aattactaat ttcagttgag accttctaat tggttttttac tgaaacattg agggaacaca   1320
aatttatggg cttcctgatg atgattcttc taggcatcat gtcctatagt ttgtcatccc   1380
tgatgaatgt aaagttacac tgttcacaaa ggttttgtct cctttccact gctattagtc   1440
atggtcactc tccccaaaat attatatttt ttctataaaa agaaaaaaat ggaaaaaaat   1500
tacaaggcaa tggaaactat tataaggcca tttccttttc acattagata aattactata   1560
aagactccta atagcttttc ctgttaaggc agacccagta tgaaatgggg attattatag   1620
caaccatttt ggggctatat ttacatgcta ctaaattttt ataataattg aaaagatttt   1680
aacaagtata aaaaattctc ataggaatta aatgtagtct ccctgtgtca gactgctctt   1740
tcatagtata actttaaatc ttttcttcaa cttgagtctt tgaagatagt tttaattctg   1800
cttgtgacat taaagatta  tttgggccag ttatagctta ttaggtgttg aagagaccaa   1860
ggttgcaagg ccaggccctg tgtgaacctt tgagctttca tagagagttt cacagcatgg   1920
actgtgtccc cacggtcatc cagtgttgtc atgcattggt tagtcaaaat ggggagggac   1980
tagggcagtt tggatagctc aacaagatac aatctcactc tgtggtggtc ctgctgacaa   2040
atcaagagca ttgcttttgt ttcttaagaa aacaaactct tttttaaaaa ttacttttaa   2100
atattaactc aaaagttgag attttggggt ggtggtgtgc caagacatta attttttttt   2160
taaacaatga agtgaaaaag ttttacaatc tctaggtttg gctagttctc ttaacactgg   2220
ttaaattaac attgcataaa cacttttcaa gtctgatcca tatttaataa tgctttaaaa   2280
taaaaataaa aacaatcctt ttgataaatt taaaatgtta cttattttaa aataaatgaa   2340
gtgagatggc atggtgaggt gaaagtatca ctggactagg aagaaggtga cttaggttct   2400
agataggtgt cttttaggac tctgattttg aggacatcac ttactatcca tttcttcatg   2460
ttaaagaag  tcatctcaaa ctcttagttt ttttttttta caactatgta atttatattc   2520
catttacata aggatacact tatttgtcaa gctcagcaca atctgtaaat ttttaaccta   2580
tgttacacca tcttcagtgc cagtcttggg caaaattgtg caagaggtga agtttatatt   2640
tgaatatcca ttctcgtttt aggactcttc ttccatatta gtgtcatctt gcctccctac   2700
cttccacatg ccccatgact tgatgcagtt ttaatacttg taattcccct aaccataaga   2760
tttactgctg ctgtggatat ctccatgaag ttttcccact gagtcacatc agaaatgccc   2820
tacatcttat ttcctcaggg ctcaagagaa tctgacagat accataaagg gatttgacct   2880
aatcactaat tttcaggtgg tggctgatgc tttgaacatc tctttgctgc ccaatccatt   2940
agcgacagta ggattttca  aacctggtat gaatagacag aaccctatcc agtggaagga   3000
gaatttaata aagatagtgc tgaaagaatt ccttaggtaa tctataacta ggactactcc   3060
tggtaacagt aatacattcc attgttttag taaccagaaa tcttcatgca atgaaaaata   3120
ctttaattca tgaagcttac ttttttttttt tggtgtcaga gtctcgctct tgtcacccag   3180
gctggaatgc agtggcgcca tctcagctca ctgcaacctc catctcccag gttcaagcga   3240
ttctcgtgcc tcggcctcct gagtagctgg gattacaggc gtgtgccact acactcaact   3300
```

```
aattttttgta ttttttaggag agacggggtt tcaccctgtt ggccaggctg gtctcgaact    3360
cctgacctca agtgatgcac ccaccttggc ctcataaacc tgttttgcag aactcattta    3420
ttcagcaaat atttattgag tgcctaccag atgccagtca ccgcacaagg cactgggtat    3480
atggtatccc caaacaagag acataatccc ggtccttagg tagtgctagt gtggtctgta    3540
atatcttact aaggcctttg gtatacgacc cagagataac acgatgcgta ttttagtttt    3600
gcaaagaagg ggtttggtct ctgtgccagc tctataattg ttttgctacg attccactga    3660
aactcttcga tcaagctact ttatgtaaat cacttcattg ttttaaagga ataaacttga    3720
ttatattgtt ttttttatttg gcataactgt gattcttttta ggacaattac tgtacacatt    3780
aaggtgtatg tcagatattc atattgaccc aaatgtgtaa tattccagtt ttctctgcat    3840
aagtaattaa aatatactta aaaattaata gttttatctg ggtacaaata aacaggtgcc    3900
tgaactagtt cacagacaag gaaacttcta tgtaaaaatc actatgattt ctgaattgct    3960
atgtgaaact acagatcttt ggaacactgt ttaggtaggg tgttaagact tacacagtac    4020
ctcgtttcta cacagagaaa gaaatggcca tacttcagga actgcagtgc ttatgagggg    4080
atatttaggc ctcttgaatt tttgatgtag atgggcattt ttttaaggta gtggttaatt    4140
acctttatgt gaactttgaa tggtttaaca aaagatttgt ttttgtagag attttaaagg    4200
gggagaattc tagaaataaa tgttacctaa ttattacagc cttaaagaca aaaatccttg    4260
ttgaagtttt tttaaaaaaa gctaaattac atagacttag gcattaacat gtttgtggaa    4320
gaatatagca gacgtatatt gtatcatttg agtgaatgtt cccaagtagg cattctaggc    4380
tctatttaac tgagtcacac tgcataggaa tttagaacct aacttttata ggttatcaaa    4440
actgttgtca ccattgcaca attttgtcct aatatataca tagaaacttt gtggggcatg    4500
ttaagttaca gtttgcacaa gttcatctca tttgtattcc attgattttt ttttttcttct    4560 aaacatttt tcttcaaaca gtatataact tttttttaggg gatttttttt tagacagcaa    4620
aaactatctg aagatttcca tttgtcaaaa agtaatgatt tcttgataat tgtgtagtaa    4680 tgtttttttag aacccagcag ttaccttaaa gctgaatttta tatttagtaa cttctgtgtt    4740
aatactggat agcatgaatt ctgcattgag aaactgaata gctgtcataa aatgaaactt    4800
tctttctaaa gaaagatact cacatgagtt cttgaagaat agtcataact agattaagat    4860
ctgtgtttta gtttaatagt ttgaagtgcc tgtttgggat aatgataggt aatttagatg    4920
aatttagggg aaaaaaaagt tatctgcaga tatgttgagg gcccatctct ccccccacac    4980
ccccacagag ctaactgggt tacagtgttt tatccgaaag tttccaattc cactgtcttg    5040
tgttttcatg ttgaaaatac ttttgcattt ttccttgag tgccaatttc ttactagtac    5100
tatttcttaa tgtaacatgt ttacctgaa tgtattttaa ctattttgt atagtgtaaa    5160 ctgaaacatg cacattttgt acattgtgct ttcttttgtg ggacatatgc agtgtgatcc    5220
agttgttttc catcatttgg ttgcgctgac ctaggaatgt tggtcatatc aaacattaaa    5280
aatgaccact cttttaattg aaattaactt ttaaatgttt ataggagtat gtgctgtgaa    5340
gtgatctaaa atttgtaata tttttgtcat gaactgtact actcctaatt attgtaatgt    5400
aataaaaata gttacagtga caaaaaaaaa aaaaaa                               5436
```

<210> SEQ ID NO 27
<211> LENGTH: 5312
<212> TYPE: DNA
<213> ORGANISM: Homo sapiens
<400> SEQUENCE: 27

-continued

```
ggccgcggcg gcggaggcag cagcggcggc ggcagtggcg gcggcgaagg tggcggcggc      60
tcggccagta ctcccggccc ccgccatttc ggactgggag cgagcgcggc gcaggcactg     120
aaggcggcgg cggggccaga ggctcagcgg ctcccaggtg cgggagagag gcctgctgaa     180
aatgactgaa tataaacttg tggtagttgg agctggtggc gtaggcaaga gtgccttgac     240
gatacagcta attcagaatc attttgtgga cgaatatgat ccaacaatag aggattccta     300
caggaagcaa gtagtaattg atggagaaac ctgtctcttg gatattctcg acacagcagg     360
tcaagaggag tacagtgcaa tgagggacca gtacatgagg actggggagg gctttctttg     420
tgtatttgcc ataaataata ctaaatcatt tgaagatatt caccattata gagaacaaat     480
taaaagagtt aaggactctg aagatgtacc tatggtccta gtaggaaata atgtgatttt     540
gccttctaga acagtagaca caaacaggc tcaggactta gcaagaagtt atggaattcc     600
ttttattgaa acatcagcaa agacaagaca gggtgttgat gatgccttct atacattagt     660
tcgagaaatt cgaaaacata agaaaagat gagcaaagat ggtaaaaaga agaaaaagaa     720
gtcaaagaca aagtgtgtaa ttatgtaaat acaatttgta cttttttctt aaggcatact     780
agtacaagtg gtaattttg tacattacac taaattatta gcatttgttt tagcattacc     840 taatttttt cctgctccat gcagactgtt agcttttacc ttaaatgctt attttaaaat     900
gacagtggaa gttttttttt cctctaagtg ccagtattcc cagagttttg gttttgaac    960 tagcaatgcc tgtgaaaaag aaactgaata cctaagattt ctgtcttggg gttttggtg    1020 catgcagttg attacttctt attttttta ccaattgtga atgttggtgt gaaacaaatt    1080
aatgaagctt ttgaatcatc cctattctgt gttttatcta gtcacataaa tggattaatt    1140
actaatttca gttgagacct tctaattggt ttttactgaa acattgaggg aacacaaatt    1200
tatgggcttc ctgatgatga ttcttctagg catcatgtcc tatagtttgt catccctgat    1260
gaatgtaaag ttacactgtt cacaaaggtt ttgtctcctt tccactgcta ttagtcatgg    1320
tcactctccc caaaatatta tattttttct ataaaaagaa aaaatggaa aaaaattaca    1380 aggcaatgga aactattata aggccatttc cttttcacat tagataaatt actataaaga    1440
ctcctaatag cttttcctgt taaggcagac ccagtatgaa atgggattga ttatagcaac    1500
cattttgggg ctatatttac atgctactaa attttataa taattgaaaa gatttttaaca    1560 agtataaaaa attctcatag gaattaaatg tagtctccct gtgtcagact gctctttcat    1620
agtataactt taaatctttt cttcaacttg agtctttgaa gatagtttta attctgcttg    1680
tgacattaaa agattatttg ggccagttat agcttattag gtgttgaaga gaccaaggtt    1740
gcaaggccag gcctgtgtg aacctttgag cttcataga gagtttcaca gcatggactg     1800
tgtccccacg gtcatccagt gttgtcatgc attggttagt caaaatgggg agggactagg    1860
gcagtttgga tagctcaaca agatacaatc tcactctgtg gtggtcctgc tgacaaatca    1920
agagcattgc ttttgtttct taagaaaaca aactctttt taaaattac ttttaaatat     1980 taactcaaaa gttgagattt tggggtggtg gtgtgccaag acattaattt ttttttaaa    2040 caatgaagtg aaaagttttt acaatctcta ggtttggcta gttctcttaa cactggttaa    2100
attaacattg cataaacact tttcaagtct gatccatatt taataatgct ttaaaataaa    2160
aataaaaaca atccttttga taaatttaaa atgttactta ttttaaaata aatgaagtga    2220
gatggcatgg tgaggtgaaa gtatcactgg actaggaaga aggtgactta ggttctagat    2280
aggtgtcttt taggactctg attttgagga catcacttac tatccatttc ttcatgttaa    2340
aagaagtcat ctcaaactct tagttttttt tttttacaac tatgtaattt atattccatt    2400
```

| | |
|---|---|
| tacataagga tacacttatt tgtcaagctc agcacaatct gtaaatttt aacctatgtt | 2460 |
| acaccatctt cagtgccagt cttgggcaaa attgtgcaag aggtgaagtt tatatttgaa | 2520 |
| tatccattct cgttttagga ctcttcttcc atattagtgt catcttgcct ccctaccttc | 2580 |
| cacatgcccc atgacttgat gcagttttaa tacttgtaat tccctaacc ataagattta | 2640 |
| ctgctgctgt ggatatctcc atgaagtttt cccactgagt cacatcagaa atgccctaca | 2700 |
| tcttatttcc tcagggctca agagaatctg acagatacca taaagggatt tgacctaatc | 2760 |
| actaattttc aggtggtggc tgatgctttg aacatctctt tgctgcccaa tccattagcg | 2820 |
| acagtaggat ttttcaaacc tggtatgaat agacagaacc ctatccagtg aaggagaat | 2880 |
| ttaataaaga tagtgctgaa agaattcctt aggtaatcta aactaggac tactcctggt | 2940 |
| aacagtaata cattccattg ttttagtaac cagaaatctt catgcaatga aaaatacttt | 3000 |
| aattcatgaa gcttactttt ttttttggt gtcagagtct cgctcttgtc acccaggctg | 3060 |
| gaatgcagtg gcgccatctc agctcactgc aacctccatc tcccaggttc aagcgattct | 3120 |
| cgtgcctcgg cctcctgagt agctgggatt acaggcgtgt gccactacac tcaactaatt | 3180 |
| tttgtatttt taggagagac ggggtttcac cctgttggcc aggctggtct cgaactcctg | 3240 |
| acctcaagtg atgcacccac cttggcctca taaacctgtt ttgcagaact catttattca | 3300 |
| gcaaatattt attgagtgcc taccagatgc cagtcaccgc acaaggcact gggtatatgg | 3360 |
| tatccccaaa caagagacat aatcccggtc cttaggtagt gctagtgtgg tctgtaatat | 3420 |
| cttactaagg cctttggtat acgacccaga gataacacga tgcgtatttt agttttgcaa | 3480 |
| agaaggggtt tggtctctgt gccagctcta taattgtttt gctacgattc cactgaaact | 3540 |
| cttcgatcaa gctactttat gtaaatcact tcattgtttt aaaggaataa acttgattat | 3600 |
| attgtttttt tatttggcat aactgtgatt cttttaggac aattactgta cacattaagg | 3660 |
| tgtatgtcag atattcatat tgacccaaat gtgtaatatt ccagttttct ctgcataagt | 3720 |
| aattaaaata tacttaaaaa ttaatagttt tatctgggta caaataaaca ggtgcctgaa | 3780 |
| ctagttcaca gacaaggaaa cttctatgta aaaatcacta tgatttctga attgctatgt | 3840 |
| gaaactacag atctttggaa cactgtttag gtagggtgtt aagacttaca cagtacctcg | 3900 |
| tttctacaca gagaaagaaa tggccatact tcaggaactg cagtgcttat gagggatat | 3960 |
| ttaggcctct tgaattttg atgtagatgg gcatttttt aaggtagtgg ttaattacct | 4020 |
| ttatgtgaac tttgaatggt ttaacaaaag atttgttttt gtagagattt taaaggggga | 4080 |
| gaattctaga aataaatgtt acctaattat tacagcctta aagacaaaaa tccttgttga | 4140 |
| agtttttta aaaaagcta aattacatag acttaggcat taacatgttt gtggaagaat | 4200 |
| atagcagacg tatattgtat catttgagtg aatgttccca agtaggcatt ctaggctcta | 4260 |
| tttaactgag tcacactgca taggaattta gaacctaact tttataggtt atcaaaactg | 4320 |
| ttgtcaccat tgcacaattt tgtcctaata tatacataga aactttgtgg ggcatgttaa | 4380 |
| gttacagttt gcacaagttc atctcatttg tattccattg attttttttt tcttctaaac | 4440 |
| attttttctt caaacagtat ataactttt ttaggggatt ttttttaga cagcaaaaac | 4500 |
| tatctgaaga tttccatttg tcaaaaagta atgatttctt gataattgtg tagtaatgtt | 4560 |
| ttttagaacc cagcagttac cttaaagctg aatttatatt tagtaacttc tgtgttaata | 4620 |
| ctggatagca tgaattctgc attgagaaac tgaatagctg tcataaaatg aaactttctt | 4680 |
| tctaaagaaa gatactcaca tgagttcttg aagaatagtc ataactagat taagatctgt | 4740 |
| gttttagttt aatagtttga agtgcctgtt tgggataatg ataggtaatt tagatgaatt | 4800 |

-continued

| | |
|---|---|
| taggggaaaa aaaagttatc tgcagatatg ttgagggccc atctctcccc ccacaccccc | 4860 |
| acagagctaa ctgggttaca gtgttttatc cgaaagtttc caattccact gtcttgtgtt | 4920 |
| ttcatgttga aaatactttt gcattttttcc tttgagtgcc aatttcttac tagtactatt | 4980 |
| tcttaatgta acatgtttac ctggaatgta ttttaactat ttttgtatag tgtaaactga | 5040 |
| aacatgcaca ttttgtacat tgtgctttct tttgtgggac atatgcagtg tgatccagtt | 5100 |
| gttttccatc atttggttgc gctgacctag gaatgttggt catatcaaac attaaaaatg | 5160 |
| accactcttt taattgaaat taacttttaa atgtttatag gagtatgtgc tgtgaagtga | 5220 |
| tctaaaattt gtaatatttt tgtcatgaac tgtactactc ctaattattg taatgtaata | 5280 |
| aaaatagtta cagtgacaaa aaaaaaaaaa aa | 5312 |

<210> SEQ ID NO 28
<211> LENGTH: 1963
<212> TYPE: DNA
<213> ORGANISM: Homo sapiens

<400> SEQUENCE: 28

| | |
|---|---|
| gaaacgtccc gtgtgggagg ggcgggtctg ggtgcggctg ccgcatgact cgtggttcgg | 60 |
| aggcccacgt ggccggggcg gggactcagg cgcctggcag ccgactgatt acgtagcggg | 120 |
| cggggccgga agtgccgctc cttggtgggg gctgttcatg gcggttccgg ggtctccaac | 180 |
| attttttcccg gtctgtggtc ctaaatctgt ccaaagcaga ggcagtggag cttgaggttc | 240 |
| ttgctggtgt gaaatgactg agtacaaact ggtggtggtt ggagcaggtg gtgttgggaa | 300 |
| aagcgcactg acaatccagc taatccagaa ccactttgta gatgaatatg atcccaccat | 360 |
| agaggattct tacagaaaac aagtggttat agatggtgaa acctgtttgt tggacatact | 420 |
| ggatacagct ggacaagaag agtacagtgc catgagagac caatacatga ggacaggcga | 480 |
| aggcttcctc tgtgtatttg ccatcaataa tagcaagtca tttgcggata ttaacctcta | 540 |
| cagggagcag attaagcgag taaaagactc ggatgatgta cctatggtgc tagtgggaaa | 600 |
| caagtgtgat ttgccaacaa ggacagttga tacaaaacaa gcccacgaac tggccaagag | 660 |
| ttacgggatt ccattcattg aaacctcagc caagaccaga caggggtgttg aagatgcttt | 720 |
| ttacacactg gtaagagaaa tacgccagta ccgaatgaaa aaactcaaca gcagtgatga | 780 |
| tgggactcag ggttgtatgg gattgccatg tgtggtgatg taacaagata ctttttaaagt | 840 |
| tttgtcagaa aagagccact tcaagctgc actgacaccc tggtcctgac ttcctggagg | 900 |
| agaagtattc ctgttgctgt cttcagtctc acagagaagc cctgctact tccccagctc | 960 |
| tcagtagttt agtacaataa tctctatttg agaagttctc agaataacta cctcctcact | 1020 |
| tggctgtctg accagagaat gcacctcttg ttactccctg ttattttcct gccctgggtt | 1080 |
| cttccacagc acaaacacac ctcaacacac ctctgccacc ccaggttttt catctgaaaa | 1140 |
| gcagttcatg tctgaaacag agaaccaaac cgcaaacgtg aaattctatt gaaacagtg | 1200 |
| tcttgagctc taaagtagca actgctggtg attttttttt tcttttttact gttgaactta | 1260 |
| gaactatgcc taatttttgg agaaatgtca taaattactg ttttgccaag aatatagtta | 1320 |
| ttattgctgt ttggtttgtt tataatgtta tcggctctat tctctaaact ggcatctgct | 1380 |
| ctagattcat aaaatacaaaa atgaatactg aattttgagt ctatcctagt cttcacaact | 1440 |
| ttgacgtaat taaatccaac ttttcacagt gaagtgcctt tttcctagaa gtggtttgta | 1500 |
| gactcctttta taatatttca gtggaataga tgtctcaaaa atccttatgc atgaaatgaa | 1560 |
| tgtctgagat acgtctgtga cttatctacc attgaaggaa agctatatct atttgagagc | 1620 |

-continued

| | |
|---|---|
| agatgccatt ttgtacatgt atgaaattgg ttttccagag gcctgttttg gggctttccc | 1680 |
| aggagaaaga tgaaactgaa agcatatgaa taatttcact taataatttt tacctaatct | 1740 |
| ccactttttt cataggttac tacctataca atgtatgtaa tttgtttccc ctagcttact | 1800 |
| gataaaccta atattcaatg aacttccatt tgtattcaaa tttgtgtcat accagaaagc | 1860 |
| tctacatttg cagatgttca aatattgtaa aactttggtg cattgttatt taatagctgt | 1920 |
| gatcagtgat tttcaaacct caaatatagt atattaacaa att | 1963 |

<210> SEQ ID NO 29
<211> LENGTH: 40
<212> TYPE: DNA
<213> ORGANISM: Artificial Sequence
<220> FEATURE:
<223> OTHER INFORMATION: Primer Sequence

<400> SEQUENCE: 29

| | |
|---|---|
| ctagctagca tacaatttgt acttttttct taaggcatac | 40 |

<210> SEQ ID NO 30
<211> LENGTH: 24
<212> TYPE: DNA
<213> ORGANISM: Artificial Sequence
<220> FEATURE:
<223> OTHER INFORMATION: Primer Sequence

<400> SEQUENCE: 30

| | |
|---|---|
| ggcacaccac caccccaaaa tctc | 24 |

<210> SEQ ID NO 31
<211> LENGTH: 23
<212> TYPE: DNA
<213> ORGANISM: Artificial Sequence
<220> FEATURE:
<223> OTHER INFORMATION: Primer Sequence

<400> SEQUENCE: 31

| | |
|---|---|
| ccatcttcag tgccagtctt ggg | 23 |

<210> SEQ ID NO 32
<211> LENGTH: 23
<212> TYPE: DNA
<213> ORGANISM: Artificial Sequence
<220> FEATURE:
<223> OTHER INFORMATION: Primer Sequence

<400> SEQUENCE: 32

| | |
|---|---|
| gggtcgtata ccaaaggcct tag | 23 |

<210> SEQ ID NO 33
<211> LENGTH: 25
<212> TYPE: DNA
<213> ORGANISM: Artificial Sequence
<220> FEATURE:
<223> OTHER INFORMATION: Primer Sequence

<400> SEQUENCE: 33

| | |
|---|---|
| gcctgaacta gttcacagac aaggg | 25 |

<210> SEQ ID NO 34
<211> LENGTH: 34
<212> TYPE: DNA
<213> ORGANISM: Artificial Sequence
<220> FEATURE:
<223> OTHER INFORMATION: Primer Sequence

<400> SEQUENCE: 34
ctagctagct caatgcagaa ttcatgctat ccag                          34

<210> SEQ ID NO 35
<211> LENGTH: 20
<212> TYPE: DNA
<213> ORGANISM: Artificial Sequence
<220> FEATURE:
<223> OTHER INFORMATION: Primer Sequence

<400> SEQUENCE: 35
ggtgtcagag tctcgctctt                                          20

<210> SEQ ID NO 36
<211> LENGTH: 23
<212> TYPE: DNA
<213> ORGANISM: Artificial Sequence
<220> FEATURE:
<223> OTHER INFORMATION: Primer Sequence

<400> SEQUENCE: 36
gggtcgtata ccaaaggcct tag                                      23

<210> SEQ ID NO 37
<211> LENGTH: 20
<212> TYPE: DNA
<213> ORGANISM: Artificial Sequence
<220> FEATURE:
<223> OTHER INFORMATION: Primer Sequence

<400> SEQUENCE: 37
cctgagtagc tgggattaca                                          20

<210> SEQ ID NO 38
<211> LENGTH: 23
<212> TYPE: DNA
<213> ORGANISM: Artificial Sequence
<220> FEATURE:
<223> OTHER INFORMATION: Primer Sequence

<400> SEQUENCE: 38
ggataccata tacccagtgc ctt                                      23

<210> SEQ ID NO 39
<211> LENGTH: 23
<212> TYPE: DNA
<213> ORGANISM: Artificial Sequence
<220> FEATURE:
<223> OTHER INFORMATION: Primer Sequence

<400> SEQUENCE: 39
ccactttcaa gctgcactga cac                                      23

<210> SEQ ID NO 40
<211> LENGTH: 27
<212> TYPE: DNA
<213> ORGANISM: Artificial Sequence
<220> FEATURE:
<223> OTHER INFORMATION: Primer Sequence

<400> SEQUENCE: 40
ctagctggag ttactggtgc aatgagc                                  27

<210> SEQ ID NO 41
<211> LENGTH: 23
<212> TYPE: DNA

-continued

```
<213> ORGANISM: Artificial Sequence
<220> FEATURE:
<223> OTHER INFORMATION: Primer Sequence

<400> SEQUENCE: 41
gatacctatg aggatttgga ggc                                              23

<210> SEQ ID NO 42
<211> LENGTH: 23
<212> TYPE: DNA
<213> ORGANISM: Artificial Sequence
<220> FEATURE:
<223> OTHER INFORMATION: Primer Sequence

<400> SEQUENCE: 42
gcatggtagc cttcagacag aac                                              23

<210> SEQ ID NO 43
<211> LENGTH: 24
<212> TYPE: DNA
<213> ORGANISM: Artificial Sequence
<220> FEATURE:
<223> OTHER INFORMATION: Primer Sequence

<400> SEQUENCE: 43
ctgcttcttg taattcatct ctgc                                             24

<210> SEQ ID NO 44
<211> LENGTH: 23
<212> TYPE: DNA
<213> ORGANISM: Artificial Sequence
<220> FEATURE:
<223> OTHER INFORMATION: Primer Sequence

<400> SEQUENCE: 44
caacttaaaa tatcggccct tcc                                              23

<210> SEQ ID NO 45
<211> LENGTH: 33
<212> TYPE: DNA
<213> ORGANISM: Artificial Sequence
<220> FEATURE:
<223> OTHER INFORMATION: Primer Sequence

<400> SEQUENCE: 45
cgaactcctg acctcaagtg atgcacccac ctt                                   33

<210> SEQ ID NO 46
<211> LENGTH: 32
<212> TYPE: DNA
<213> ORGANISM: Artificial Sequence
<220> FEATURE:
<223> OTHER INFORMATION: Primer Sequence

<400> SEQUENCE: 46
atcacttgag gtcaggagtt cgagaccagc ct                                    32

<210> SEQ ID NO 47
<211> LENGTH: 26
<212> TYPE: RNA
<213> ORGANISM: Caenorhabditis elegans

<400> SEQUENCE: 47
acuuguaguc gaucuccuuc cgccuc                                           26

<210> SEQ ID NO 48
```

```
<211> LENGTH: 22
<212> TYPE: RNA
<213> ORGANISM: Caenorhabditis elegans

<400> SEQUENCE: 48
auguuauaau guaugaugga gu                                            22

<210> SEQ ID NO 49
<211> LENGTH: 25
<212> TYPE: RNA
<213> ORGANISM: Caenorhabditis elegans

<400> SEQUENCE: 49
ugcaucgauu gaacuuguuc ucucg                                         25

<210> SEQ ID NO 50
<211> LENGTH: 20
<212> TYPE: RNA
<213> ORGANISM: Caenorhabditis elegans

<400> SEQUENCE: 50
uccuucauuc uaauuccuca                                               20

<210> SEQ ID NO 51
<211> LENGTH: 24
<212> TYPE: RNA
<213> ORGANISM: Caenorhabditis elegans

<400> SEQUENCE: 51
acuagcaucc gaaccccuc cucg                                           24

<210> SEQ ID NO 52
<211> LENGTH: 21
<212> TYPE: RNA
<213> ORGANISM: Caenorhabditis elegans

<400> SEQUENCE: 52
uguuauaaug uaugauggag u                                             21

<210> SEQ ID NO 53
<211> LENGTH: 20
<212> TYPE: RNA
<213> ORGANISM: Caenorhabditis elegans

<400> SEQUENCE: 53
ugcuuuauuc cccuuccucg                                               20

<210> SEQ ID NO 54
<211> LENGTH: 22
<212> TYPE: RNA
<213> ORGANISM: Caenorhabditis elegans

<400> SEQUENCE: 54
uucauacaaa uuauuggccu ca                                            22

<210> SEQ ID NO 55
<211> LENGTH: 23
<212> TYPE: RNA
<213> ORGANISM: Caenorhabditis elegans

<400> SEQUENCE: 55
auucgaaagu uuuugcuccc ucg                                           23

<210> SEQ ID NO 56
```

-continued

```
<211> LENGTH: 19
<212> TYPE: RNA
<213> ORGANISM: Caenorhabditis elegans

<400> SEQUENCE: 56 ucuauuuuc cuauuccuc                                            19

<210> SEQ ID NO 57
<211> LENGTH: 22
<212> TYPE: RNA
<213> ORGANISM: Homo sapiens

<400> SEQUENCE: 57
uugauauguu ggaugaugga gu                                       22

<210> SEQ ID NO 58
<211> LENGTH: 22
<212> TYPE: DNA
<213> ORGANISM: Artificial Sequence
<220> FEATURE:
<223> OTHER INFORMATION: Consensus sequence

<400> SEQUENCE: 58
tgaggtagta ggttgtatag tt                                       22

<210> SEQ ID NO 59
<211> LENGTH: 18
<212> TYPE: DNA
<213> ORGANISM: Homo sapiens

<400> SEQUENCE: 59
tgaggtagta gtttgtgc                                            18

<210> SEQ ID NO 60
<211> LENGTH: 22
<212> TYPE: DNA
<213> ORGANISM: Homo sapiens

<400> SEQUENCE: 60
tgaggtagta gtgtgtacag tt                                       22

<210> SEQ ID NO 61
<211> LENGTH: 22
<212> TYPE: DNA
<213> ORGANISM: Homo sapiens

<400> SEQUENCE: 61
tgaggtagta gtttgtacag ta                                       22

<210> SEQ ID NO 62
<211> LENGTH: 21
<212> TYPE: DNA
<213> ORGANISM: Homo sapiens

<400> SEQUENCE: 62
agaggtagta gtttgcatag t                                        21

<210> SEQ ID NO 63
<211> LENGTH: 21
<212> TYPE: DNA
<213> ORGANISM: Homo sapiens

<400> SEQUENCE: 63
agaggtagta ggttgcatag t                                        21
```

```
<210> SEQ ID NO 64
<211> LENGTH: 22
<212> TYPE: DNA
<213> ORGANISM: Homo sapiens

<400> SEQUENCE: 64
tgaggtagta gattgtatag tt                                              22

<210> SEQ ID NO 65
<211> LENGTH: 22
<212> TYPE: DNA
<213> ORGANISM: Homo sapiens

<400> SEQUENCE: 65
tgaggtagta ggttgtatag tt                                              22

<210> SEQ ID NO 66
<211> LENGTH: 21
<212> TYPE: DNA
<213> ORGANISM: Homo sapiens

<400> SEQUENCE: 66
tgaggtagga ggttgtatag t                                               21

<210> SEQ ID NO 67
<211> LENGTH: 22
<212> TYPE: DNA
<213> ORGANISM: Homo sapiens

<400> SEQUENCE: 67
tgaggtagta ggttgtatgg tt                                              22

<210> SEQ ID NO 68
<211> LENGTH: 22
<212> TYPE: DNA
<213> ORGANISM: Homo sapiens

<400> SEQUENCE: 68
tgaggtagta ggttgtgtgg tt                                              22

<210> SEQ ID NO 69
<211> LENGTH: 22
<212> TYPE: DNA
<213> ORGANISM: Homo sapiens

<400> SEQUENCE: 69
tgaggtagta agttgtattg tt                                              22

<210> SEQ ID NO 70
<211> LENGTH: 22
<212> TYPE: DNA
<213> ORGANISM: Homo sapiens

<400> SEQUENCE: 70
tgaggtagta tgtaatattg ta                                              22

<210> SEQ ID NO 71
<211> LENGTH: 20
<212> TYPE: DNA
<213> ORGANISM: Artificial Sequence
<220> FEATURE:
<223> OTHER INFORMATION: Consensus sequence

<400> SEQUENCE: 71
```

```
tgaggtaggt gcgagaaatg                                               20

<210> SEQ ID NO 72
<211> LENGTH: 23
<212> TYPE: DNA
<213> ORGANISM: Homo sapiens

<400> SEQUENCE: 72
tgaggtaggc tcagtagatg cga                                           23

<210> SEQ ID NO 73
<211> LENGTH: 65
<212> TYPE: RNA
<213> ORGANISM: Caenorhabditis elegans

<400> SEQUENCE: 73
ugagguagua gguuguauag uuuggaauau uaccaccggu gaacuaugca auuucuacc    60 uuacc                                                               65

<210> SEQ ID NO 74
<211> LENGTH: 61
<212> TYPE: RNA
<213> ORGANISM: Drosophila melanogaster

<400> SEQUENCE: 74
ugagguagua gguuguauag uaguaauuac acaucauacu auacaaugug cuagcuuucu   60
u                                                                   61

<210> SEQ ID NO 75
<211> LENGTH: 70
<212> TYPE: RNA
<213> ORGANISM: Homo sapiens

<400> SEQUENCE: 75
ugagguagua gguuguauag uuuggggcuc ugcccugcua ugggauaacu auacaaucua   60
cugucuuucc                                                          70

<210> SEQ ID NO 76
<211> LENGTH: 22
<212> TYPE: RNA
<213> ORGANISM: Homo sapiens

<400> SEQUENCE: 76
ugagguagua gguuguauag uu                                            22

<210> SEQ ID NO 77
<211> LENGTH: 22
<212> TYPE: RNA
<213> ORGANISM: Homo sapiens

<400> SEQUENCE: 77
ugagguagua gguugugugg uu                                            22

<210> SEQ ID NO 78
<211> LENGTH: 22
<212> TYPE: RNA
<213> ORGANISM: Homo sapiens

<400> SEQUENCE: 78
ugagguagua gguuguaugg uu                                            22

<210> SEQ ID NO 79
```

```
<211> LENGTH: 21
<212> TYPE: RNA
<213> ORGANISM: Homo sapiens

<400> SEQUENCE: 79
agagguagua gguugcauag u                                              21

<210> SEQ ID NO 80
<211> LENGTH: 20
<212> TYPE: RNA
<213> ORGANISM: Homo sapiens

<400> SEQUENCE: 80
ugagguagga gguuguauau                                                20

<210> SEQ ID NO 81
<211> LENGTH: 22
<212> TYPE: RNA
<213> ORGANISM: Homo sapiens

<400> SEQUENCE: 81
ugagguagua gauuguauag uu                                             22

<210> SEQ ID NO 82
<211> LENGTH: 20
<212> TYPE: RNA
<213> ORGANISM: Homo sapiens

<400> SEQUENCE: 82
ugagguagua guuuguacag                                                20

<210> SEQ ID NO 83
<211> LENGTH: 21
<212> TYPE: RNA
<213> ORGANISM: Homo sapiens

<400> SEQUENCE: 83
ugagguaguu guuuguggug u                                              21

<210> SEQ ID NO 84
<211> LENGTH: 61
<212> TYPE: RNA
<213> ORGANISM: Caenorhabditis elegans

<400> SEQUENCE: 84
uucccugaga ccucaagugu gaguguacua uguaugcuuc acaccgggc ucuccgggua     60
c                                                                    61

<210> SEQ ID NO 85
<211> LENGTH: 73
<212> TYPE: RNA
<213> ORGANISM: Caenorhabditis elegans

<400> SEQUENCE: 85
uccggugagg uaguagguug uauaguuugg aauauuacca ccggugaacu augcaauuuu    60
cuaccuuacc gga                                                       73

<210> SEQ ID NO 86
<211> LENGTH: 18
<212> TYPE: RNA
<213> ORGANISM: Caenorhabditis elegans

<400> SEQUENCE: 86
```

-continued

| | |
|---|---|
| cucacacaac ucaggaau | 18 |

<210> SEQ ID NO 87
<211> LENGTH: 23
<212> TYPE: RNA
<213> ORGANISM: Caenorhabditis elegans

<400> SEQUENCE: 87

| | |
|---|---|
| gagugugacu ccagaguccc uug | 23 |

<210> SEQ ID NO 88
<211> LENGTH: 23
<212> TYPE: RNA
<213> ORGANISM: Caenorhabditis elegans

<400> SEQUENCE: 88

| | |
|---|---|
| uuauacaacc cruucuacac uca | 23 |

<210> SEQ ID NO 89
<211> LENGTH: 21
<212> TYPE: RNA
<213> ORGANISM: Caenorhabditis elegans

<400> SEQUENCE: 89

| | |
|---|---|
| ugauauguug gaugauggag u | 21 |

<210> SEQ ID NO 90
<211> LENGTH: 21
<212> TYPE: DNA
<213> ORGANISM: Homo sapiens

<400> SEQUENCE: 90

| | |
|---|---|
| gatkcaccca ccttggcctc a | 21 |

<210> SEQ ID NO 91
<211> LENGTH: 21
<212> TYPE: DNA
<213> ORGANISM: Homo sapiens

<400> SEQUENCE: 91

| | |
|---|---|
| gattcaccca ccttggcctc a | 21 |

<210> SEQ ID NO 92
<211> LENGTH: 21
<212> TYPE: DNA
<213> ORGANISM: Homo sapiens

<400> SEQUENCE: 92

| | |
|---|---|
| gatgcaccca ccttggcctc a | 21 |

<210> SEQ ID NO 93
<211> LENGTH: 21
<212> TYPE: DNA
<213> ORGANISM: Homo sapiens

<400> SEQUENCE: 93

| | |
|---|---|
| gattcaccca ccttggcctc a | 21 |

<210> SEQ ID NO 94
<211> LENGTH: 21
<212> TYPE: DNA
<213> ORGANISM: Homo sapiens
<220> FEATURE:
<221> NAME/KEY: misc_feature
<222> LOCATION: (4)..(4)

```
<223> OTHER INFORMATION: n is a, c, g, t or u

<400> SEQUENCE: 94
gatncaccca ccttggcctc a                                              21
```

GENETIC LESION ASSOCIATED WITH CANCER

RELATED APPLICATIONS

This application is a continuation application of U.S. Ser. No. 12/600,013, which is a national stage application, filed under 35 U.S.C. §371, of International Application No. PCT/US2008/065302, filed on May 30, 2008, which claims the benefit of U.S. Ser. No. 60/932,575 filed May 31, 2007, U.S. Ser. No. 61/001,965 filed Nov. 5, 2007, U.S. Ser. No. 61/065,745 filed Feb. 14, 2008 and U.S. Ser. No. 61/124,610 filed Apr. 18, 2008, the contents of which are each herein incorporated by reference in their entirety.

FIELD OF THE INVENTION

This invention relates generally to the fields of cancer and molecular biology. The invention provides compositions and methods for predicting increased risk of developing cell proliferative diseases, such as cancer.

BACKGROUND OF THE INVENTION

Even though there has been progress in the field of cancer detection, there still remains a need in the art for the identification of new genetic markers for a variety of cancers that can be easily used in clinical applications. To date, there are relatively few options available for predicting the risk of developing cancer.

A test for predicting the risk of developing lung cancer would be particularly useful. Lung cancer is an enormous public health problem, with smoking as the number one risk factor, with 44.5 million people in the United States (20.9% of the population), and over 1.3 billion people in the world currently smoking. Unfortunately, smoking cessation does not eliminate a person's risk for developing lung cancer. Compared to never smokers, former smokers have a 6.6-fold increase in relative lung cancer risk for up to 30 years after smoking cessation (95% Confidence Interval=5.0-8.7). Screening programs have been initiated in these populations: The Early Lung Cancer Action Project (ELCAP) found that a chest computed tomography (C T) scan is three times more sensitive in detecting early-stage lung cancer than a chest X-ray in "high-risk" populations (2.4% versus 0.7%), and may improve survival rates. There remains considerable controversy over the use of lung CT scans as a global screening approach for lung cancer however, due to the expense (estimated cost 2 billion dollars yearly in the US alone) and the very low yield of yearly cancer detection (1.2%). A genetic marker capable of determining a smoker's risk of developing lung cancer would be a particularly useful test that could be used in conjunction with screening programs to diagnose lung cancer at an earlier stage, and thus reduce mortality of this devastating disease.

Accordingly, the identification of genetic markers for cancer is particularly relevant to improving prognosis, diagnosis, and treatment of the disease. As such, there is need in the art to identify alternative genetic markers that can be quickly, easily, and safely detected. Such markers may be used to identify those individuals who would benefit from screening or intervention.

SUMMARY OF THE INVENTION

The invention provides compositions and methods for identifying one or more genetic markers within let-7 family miRNA binding sites that are predictive of the onset, development and prognosis of a variety of disorders, such as, for example, all varieties of lung cancer, ovarian cancer, breast cancer, uterine cancer, head and neck cancer, pancreatic cancer, and colon cancer. In a specific embodiment, the genetic marker of the invention is a single nucleotide polymorphism (SNP). In another specific embodiment of the invention, the presence of a SNP within a let-7 family miRNA binding site is predictive of the onset, development and prognosis of cancer. Subjects carrying a particular SNP, referred to herein as the LCS6 SNP, have a significantly increased risk of developing cancer. Smokers who carry the LCS6 SNP are far more likely to develop non-small cell lung cancer (NSCLC) and ovarian cancer. Moreover, the occurrence of the LCS6 SNP is associated with earlier onset of cancer, increased occurrence of secondary cancers (including multiple secondary cancers), and increased occurrence of particularly aggressive or high risk forms of cancer. Carriers of the LCS6 SNP are particularly prone to developing all varieties of lung cancer, ovarian cancer, breast cancer, uterine cancer, head and neck cancer, pancreatic cancer, and colon cancer.

In one aspect, the invention provides an isolated polynucleotide molecule comprising of between 10-50 bases of which at least 10 contiguous bases including a polymorphic site are from SEQ ID NO: 21 in which the nucleotide at position 4 of SEQ ID NO: 21 is not a uracil (U) or thymine (T). Furthermore, the invention encompasses this isolated polynucleotide molecule wherein the nucleotide at position 4 of SEQ ID NO: 21 is a guanine (G). Compositions of the invention also include an isolated polynucleotide molecule that is complementary to the this isolated polynucleotide molecule.

In another aspect, the invention provides an isolated polynucleotide molecule comprising a 3' untranslated region (UTR) of KRAS, wherein the polynucleotide contains a single nucleotide polymorphism (SNP) within a Let-7 Complementary Site (LCS) that modulates the binding efficacy of a let-7 family miRNA molecule. Furthermore, the invention comprises this isolated polynucleotide molecule of wherein the SNP occurs at position 4 of LCS6 (SEQ ID NO: 21) and wherein the nucleotide at position 4 of SEQ ID NO: 21 is a guanine (G). Compositions of the invention also include an isolated polynucleotide molecule that is complementary to this isolated polynucleotide.

The invention further provides an isolated and purified polynucleotide comprising a sequence of at least 20 nucleotides of a KRAS allele, wherein the polynucleotide contains at least one mutation relative to KRAS shown in SEQ ID NO: 24, the mutation comprising a uracil (U) or thymine (T) to guanine (G) transition at nucleotide 3377 as shown in SEQ ID NO: 24. Alternatively, or in addition, the invention comprises, an isolated and purified polynucleotide comprising a sequence of at least 20 nucleotides of a KRAS allele, wherein the polynucleotide contains at least one mutation relative to KRAS shown in SEQ ID NO: 25, the mutation comprising a uracil (U) or thymine (T) to guanine (G) transition at nucleotide 3253 as shown in SEQ ID NO: 25.

Compositions of the invention provide an isolated polynucleotide including a nucleotide sequence of SEQ ID NO: 21; a fragment of this nucleotide sequence, provided that the fragment includes a polymorphic site in the polymorphic sequence; a complimentary nucleotide sequence comprising a sequence complementary to SEQ ID NO: 21; and a fragment of the complementary nucleotide sequence, provided that the fragment includes a polymorphic site in the polymorphic sequence.

Compositions of the invention provide an isolated polynucleotide including a nucleotide sequence of SEQ ID NO:

26; a fragment of this nucleotide sequence, provided that the fragment includes a polymorphic site in the polymorphic sequence; a complimentary nucleotide sequence comprising a sequence complementary to SEQ ID NO: 26; and a fragment of the complementary nucleotide sequence, provided that the fragment includes a polymorphic site in the polymorphic sequence.

Compositions of the invention provide an isolated polynucleotide including a nucleotide sequence of SEQ ID NO: 27; a fragment of this nucleotide sequence, provided that the fragment includes a polymorphic site in the polymorphic sequence; a complimentary nucleotide sequence comprising a sequence complementary to SEQ ID NO: 27; and a fragment of the complementary nucleotide sequence, provided that the fragment includes a polymorphic site in the polymorphic sequence.

The invention further encompasses a method of detecting the LCS6 SNP. The identity of the polymorphism can be determined by amplifying a target region containing the polymorphic site directly from one or both copies of the KRAS gene, or a fragment thereof. The sequence of the amplified region can be determined by conventional methods. The polymorphism may be identified directly, known as positive-type identification, or by inference, referred to as negative-type identification.

The target region(s) may be amplified using any oligonucleotide-directed amplification method, including but not limited to polymerase chain reaction (PCR), ligase chain reaction (LCR), and oligonucleotide ligation assay (OLA). Other known nucleic acid amplification procedures may be used to amplify the target region including transcription-based amplification systems and isothermal methods.

In a specific embodiment, the invention provides a method of detecting the LCS6 SNP in a KRAS polynucleotide by obtaining a sample of KRAS polynucleotide; amplifying the KRAS polynucleotide sample by polymerase chain reaction (PCR); digesting the PCR product with one or more restriction enzyme(s); separating these fragments by gel electrophoresis; and comparing the pattern of fragment migration of the polynucleotide sample to a control sample, wherein any change from the control pattern indicates the presence of a SNP in the polynucleotide. In specific embodiments, the control sample contains SEQ ID NO: 15.

The invention provides a method of identifying a mutation within a let-7 Complementary Site (LCS) of a test polynucleotide by contacting the test polynucleotide to a let-7 family miRNA molecule; assessing the binding efficacy of the let-7 family miRNA molecule to the test polynucleotide; and comparing the binding efficacy of the let-7 family miRNA molecule to the test polynucleotide to the binding efficacy of the let-7 family miRNA molecule to a control polynucleotide. An alternation in the binding efficacy to the test polynucleotide compared to the control polynucleotide indicates the presence of a mutation in the test polynucleotide.

The invention provides methods for identifying subjects at risk for developing cell proliferative diseases by identifying genetic mutations in miRNA binding sites that predispose an individual to such disorders. Moreover, the invention provides methods of predicting the onset of cell proliferative diseases in subjects carrying these genetic mutations.

Methods of the invention are used to identify a single nucleotide polymorphism (SNP) in a let-7 miRNA binding site in the KRAS 3'UTR that is implicated in a variety of disorders. In a specific embodiment of the invention, the presence of the SNP is predictive for development of cell proliferative disorders, such as cancer. In another embodiment of the invention, the presence of the SNP is indicative of an increased risk of cancer.

Additionally, the invention provides methods for the identification of additional mutations in miRNA binding sites located in the 3' UTR of target genes, in particular oncogenes and proto-oncogenes, that are associated with a cell proliferative disorder, such as cancer, and methods of using identified mutations within screening programs to assess risk of developing a cell proliferative disorder.

Specifically, the invention provides a method of identifying subjects at increased risk for developing a cell proliferative disorder. The method comprises obtaining a nucleic acid sample from a subject; detecting the presence of a mutation in a miRNA binding site in the 3' UTR of RAS. The presence of the mutation is indicative of an increased risk of developing a cell proliferative disorder.

The invention also provides a method of predicting the onset of developing cancer in a subject at risk for developing a cell proliferative disorder. The method includes obtaining a nucleic acid sample from a subject and detecting the presence of a mutation in a miRNA binding site in the 3' UTR of RAS. The presence of a mutation indicates an earlier onset of developing a cell proliferative disorder Mutations of the invention include single nucleotide polymorphisms (SNPs). Furthermore, exemplary mutations include, but are not limited to, deletions, insertions, inversions, substitutions, frameshifts, and recombinations. In one aspect, the mutation occurs within one or more let-7 complementary sites (LCSs). In one embodiment, the LCS is LCS6. In another embodiment, the mutation is a SNP at position 4 of LCS6 (SEQ ID NOs: 15 or 21). In a preferred embodiment, the mutation is a SNP where the guanosine triphosphate resides at position 4 of LCS6 (SEQ ID NO: 21). Furthermore, mutations occur within methylated genomic sequences. Alternatively, or in addition, mutations of the invention occur within an unmethylated genomic sequence.

Mutations of the invention modulate the binding efficacy of at least one miRNA. In a preferred embodiment, the mutation occurs in an oncogene or a proto-oncogene. In one example, the mutation results in increased binding of at least one miRNA.

Cell proliferative disorders of the invention include cancer, for example, such as all varieties of lung cancer (e.g., non-small cell lung (NSCLC) cancer and small cell lung cancer), ovarian cancer, breast cancer, uterine cancer, head and neck cancer, pancreatic cancer and colon cancer.

RAS genes of the invention include HRAS, KRAS, and NRAS.

In certain preferred embodiments, miRNA molecules of the invention belong to the let-7 family of miRNA molecules.

Moreover, the invention provides a method of identifying a subject at risk for developing a cell proliferative disease by obtaining a DNA sample from the subject; amplifying one or more polynucleotides from a subject comprising proto-oncogenes or oncogenes; sequencing the polynucleotides; comparing the polynucleotide sequences of the subject to one or more control sequences; and identifying mutations in the polynucleotide sequence of a subject that modulate the binding efficacy of at least one miRNA. Optimum control sequences contain polynucleotide sequences to which at least one miRNA binds, thereby silencing translation of the control sequences.

Furthermore, the invention provides a method of predicting the occurrence of a cell proliferative disease in a subject by obtaining a DNA sample from a subject; amplifying one or more polynucleotides from the subject comprising proto-oncogenes or oncogenes; sequencing the polynucleotides; comparing the polynucleotide sequences of the subject to one or more control sequences; and identifying mutations in the polynucleotide sequence of the subject that diminish the binding efficacy of at least one miRNA. The control sequences contain polynucleotide sequences to which at least one miRNA binds. The number of identified mutations correlates with an increased probability of developing a cell proliferative disorder.

The invention comprises subjects that are human and animal. Subjects are healthy individuals without any family history of cancer. Alternatively, or in addition, subjects have developed at least one cancer. Subjects have a family history of cancer. Subjects encompassed by the invention are screened for a wide range of cancers by the instant methods.

The invention comprises amplification of polynucleotide sequences. In a preferred embodiment, the amplification step is accomplished by polymerase chain reaction (PCR). However, all known amplification methods are contemplated and encompassed by the invention.

The invention includes all known endogenous miRNAs, their sequences, their targets, and the sequences of their complementary binding sites. As used herein, the term "complementary binding site" is meant to encompass the sequence within a target mRNA which is complementary to the miRNA, e.g. the mRNA sequence sufficient or required for binding the miRNA. In a preferred embodiment, the endogenous miRNA and/or complimentary binding site belongs to the let-7 family of miRNA molecules.

The invention comprises mutations within miRNA complimentary binding sites. Exemplary mutations include, but are not limited to, deletions, insertions, inversions, substitutions, frameshifts, or recombinations. In a preferred embodiment, the mutation is a single nucleotide polymorphism (SNP). Alternatively, or in addition, the mutation occurs within a let-7 complementary site (LCS). In a preferred embodiment, the LCS is LCS6. For example, the mutation is a SNP at position 4 of LCS6 (SEQ ID NOs: 15 or 21).

Mutations occur within a sequence encoding a 3' untranslated region (UTR). Alternatively, or in addition, mutations occur within a sequence encoding any portion of a mRNA transcript. Mutations of the invention also occur within areas of DNA modification. For instance, mutations occur within a methylated genomic sequence. Alternatively, or in addition, mutations occur within an unmethylated genomic sequence.

BRIEF DESCRIPTION OF THE DRAWINGS

FIG. 7 shows photographs of gel electrophoresis showing DNA expression levels (left panel) and mutant *C. elegans* (middle and right panels). Photographs show that overexpression of a let-7 gene (mir-84, left and right) silences an activating mutation in RAS that causes bursting from the pseudovulva (middle).

FIG. 11 is a table showing exemplary let-7 family miRNAs located in "fragile regions" of chromosomes often associated with various cancers.

FIG. 13 provides sequence comparisons within the LCS6 region showing how SNP mutations can alter miRNA alignment and binding efficacy. LCS6 is drawn 5' to 3'. let-7s are drawn 3' to 5'. The left column depicts the predicted binding of let-7 with the normal LCS6 (GAUUCACCCACCUUG-GCCUCA (SEQ ID NO: 15)). The right column depicts the predicted binding of let-7 with the variant LCS6 (GAUG-CACCCACCUUGGCCUCA (SEQ ID NO: 21, SNP bolded for emphasis)). The following sequences of let-7 family members are depicted in an alignment with either the normal or variant LCS6 (sequences provided 5' to 3'): UGAG-GUAGUAGGUUGUAUAGUU (SEQ ID NO: 76, let-7a), UGAGGUAGUAGGUUGUGUGGUU (SEQ ID NO: 77, let-7b), UGAGGUAGUAGGUUGUAUGGUU (SEQ ID NO: 78, let-7c), AGAGGUAGUAGGUUGCAUAGU (SEQ ID NO: 79, let-7d), UGAGGUAGGAGGUUGUAUAU (SEQ ID NO: 80, let-7e), UGAGGUAGUAGAUU-GUAUAGUU (SEQ ID NO: 81, let-7f), UGAG-GUAGUAGUUUGUACAG (SEQ ID NO: 82, let-7g), UGAGGUAGUUGUUUGUGGUGU (SEQ ID NO: 83, let-7i).

FIG. 24 shows the effect of the variant allele on proposed let-7 binding to LCS6. Table comparing the predicted binding energies of the different human let-7s and the wild type and alternative LCS6. These values were generated using RNAhybrid. Δ mfe represents the change in binding energy if let-7 binds to the variant LCS6 rather than the reference LCS6. mfe=minimum free energy. The duplexes predicted by RNAhybrid, corresponding these mfe values are shown in FIG. 16.

DETAILED DESCRIPTION

Figure 1:
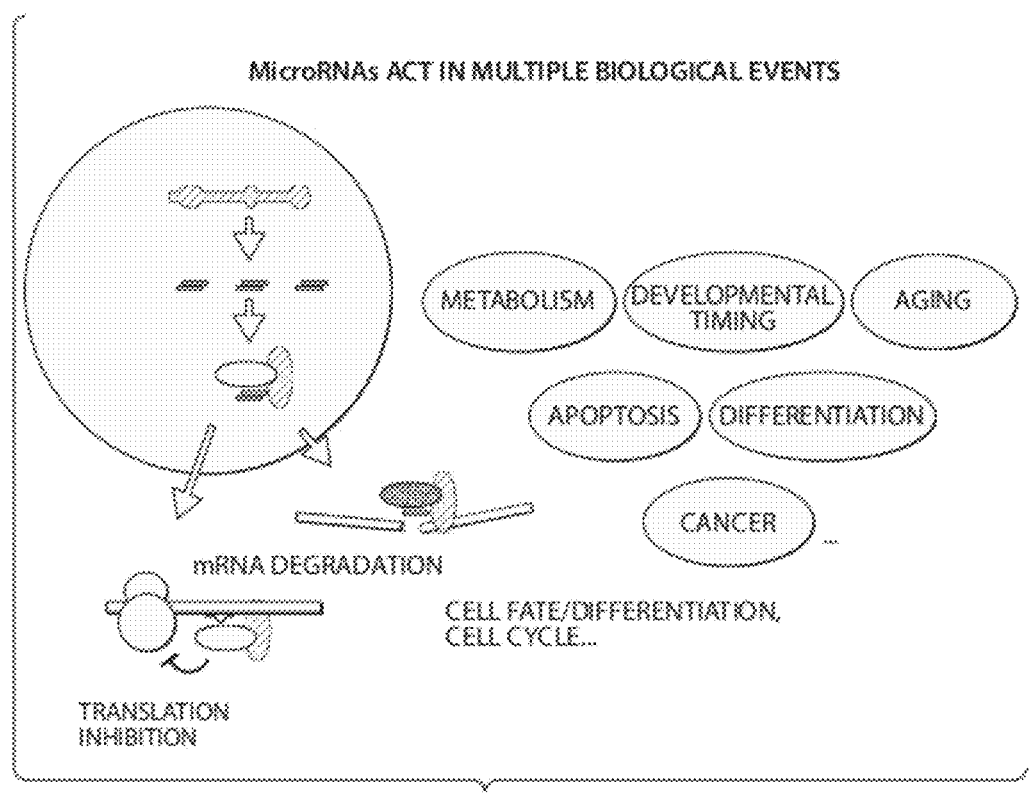
FIG. 1 is a schematic drawing showing microRNA (miRNA) processing and functions.

The invention is based upon the unexpected discovery of a novel SNP in the 3' untranslated region (UTR) of KRAS. More specifically, the invention is based upon the discovery that the presence of this novel SNP, referred to herein as the "LCS6 SNP," is predictive of the onset, severity, type and/or subtype, and in certain individuals, the occurrence of additional, or secondary, cancers that will develop. It was determined that the presence of the LCS6 SNP is associated with increased risk of developing cancer, such as, but not limited to smoking-induced non-small cell lung cancer (NSCLC) and ovarian cancer.

The invention provides a method of identifying mutations within mRNA transcripts targeted by tumor suppressor microRNAs that modulate endogenous miRNA binding efficacy. Specifically, methods of the invention have been used to identify a novel SNP, the LCS6 SNP, in a let-7 complementary site within the KRAS 3'UTR that leads to altered KRAS expression.

The LCS6 SNP was found in 20.3% of single institution collected lung cancer cases and in 5.8% of the world populations. The let-7 family-of-microRNAs (miRNAs) are global genetic regulators important in controlling lung cancer oncogene expression by binding to the 3'UTRs (untranslated regions) of their target messenger RNAs (mRNAs).

SNPs, including the LCS6 SNP, identified using the methods of the invention can be used to screen individuals at increased risk of developing cancer. There are 100 million current or ex-smokers in the United States alone and 1.3 billion smokers worldwide that would benefit from screening for the LCS6 SNP, as well as other SNPs identified using methods of the invention, to help identify those that would benefit from high-level screening for lung cancer development, to allow identification of early tumors and increased chance for cure for these patients. Additionally, some identified cancers could be totally prevented in SNP carriers, especially those carrying the LCS6 SNP, by minimally invasive surgeries, such as ovarian cancer. Patients with a cancer diagnosis should also be tested to help identify those at high risk for developing additional cancers, as well as to identify families that should be tested for the LCS6 SNP.

Currently only 3% of cancers can be attributed to a genetic cause. The invention comprises methods of identifying SNPs within mRNA transcripts of oncogenes that inhibit or diminish binding efficacy of tumor suppressor miRNAs that silence translation of these transcripts. In one preferred embodiment, method of the invention are used to identify SNPs that disrupt a miRNA binding site and are associated with increased risk to numerous cancers. Because miRNAs are recently discovered global gene regulators, and their binding region (the 3'UTR) was previously discarded as junk DNA, the paradigm of miRNA binding site disruption and disease is a novel and unexplored direction of study.

MiRNAs are recently identified gene regulators that are at abnormal levels and implicated in virtually all cancer subtypes studied (Esquela-Kerscher A. and Slack, F. 2006.

Nature Reviews Cancer 6:259-69). MiRNAs bind to the 3' untranslated regions (3'UTRs) of their target genes, regions which are evolutionarily highly conserved, suggesting an important role for these regions in natural selection. Because miRNAs each regulate hundreds of mRNAs simultaneously, the potential of cellular transformation resulting from single miRNA disturbance is high. In particular, the let-7 family of miRNAs is linked to lung cancer: let-7 miRNAs are poorly expressed in non-small cell lung cancer (NSCLC) (Johnson S. M. et al. Cell. 2005; 120(5):635-47; and Calin, G. A. et al. PNAS USA 2004; 101(9): 2999-3004); let-7 miRNAs regulate multiple lung cancer oncogenes, including RAS (Johnson C. et al. Cancer Research. 2007; 67:7713-22); and let-7 miRNAs inhibit growth of lung cancer cell lines in vitro (Takamizawa J. et al. Cancer Res 2004; 64(11): 3753-6). The role of let-7 disturbance in the initiation of cancer has been previously undefined.

The role of miRNA single nucleotide polymorphisms (SNPs) as they relate to predisposition to disease is just being defined. Recent evidence has shown that a point mutation identified in Tourette's syndrome patients in the 3'UTR of SLITRK1 disrupts the binding of miR-189 (Abelson J. F. Science 2005; 310: 317-20). In addition, SNPs in miRNAs that are important in cancer have been identified; mir-125a, which is known to be at altered levels in breast cancer (Iorio, M. V. et al. Cancer Res 2005; 65(16):7065-70; Scott, G. K. et al. J. Biol Chem 2007; 282(2): 1479-86), has a variant allele at a SNP in its coding sequence that decreases its expression (Duan, R. et al. Hum Mol Genet 2007; 16:1124-31). Furthermore, there are SNPs in miRNA target sites in human cancer genes with allele frequencies that vary between cancerous and normal tissues (Landi, D. et al. DNA and Cell Biology 2007; 0:1-9). Supporting the potential importance of SNPs in miRNA binding sites in cancer predisposition was the identification of SNPs in miRNA binding sites of miRNAs upregulated in papillary thyroid cancer in the KIT oncogene (He, H. et al. PNAS 2005; 102:19075-80). Importantly, SNPs in miRNA binding sites that predispose an individual to a specific cancer type and act as a genetic marker of cancer risk have not previously been identified.

To identify SNPs of the invention, the 3' UTRs of known lung cancer oncogenes were sequenced to evaluate miRNA binding site abnormalities in lung cancer. The LCS6 SNP was subsequently identified that is capable of disrupting a miRNA binding site in 20% of lung cancer patients in one of these genes. Experimental data proves in a case control design that the presence of the LCS6 SNP increased the carrier's risk of developing non-small cell lung cancer (OR=2.3, 95% Confidence Interval, 1.1-4.6, p<0.02). Moreover, the methods of the invention have been used to show that the LCS6 SNP is very prevalent in numerous other cancer types, including ovarian, breast, head and neck, uterine and pancreas, demonstrating that the LCS6 SNP is a biomarker of increased cancer risk for its carriers. Because the LCS6 SNP alters miRNA binding, it is a target for therapy in its carriers. Further, miRNA binding site SNPs are used to predict disease risk.

Specifically, the LCS6 SNP, which comprises a variant allele in a let-7 complementary site in the KRAS 3'UTR, leads to altered KRAS expression. The discovery that the LCS6 SNP disrupts miRNA regulation of a known oncogene, and the ability of the LCS6 SNP to affect cancer predisposition, creates a new paradigm. The present invention provides methods for identification of similar SNPs in all cancer types. This variant allele adds to our knowledge of genetic markers of increased smoking-induced lung cancer risk, which enriches screening programs. The invention comprises methods of screening for increased cancer risk. Furthermore, because the LCS6 SNP, as all other mutations encompassed by the invention, is genetically inherited, families with cancer histories should be screened to evaluate their genetic risk of developing cancer. Specifically, individuals with the LCS6 SNP having families with smoking-induced cancer histories should be screened to evaluate their genetic risk of developing lung cancer.

Single Nucleotide Polymorphisms (SNPs)

A single nucleotide polymorphism (SNP) is a DNA sequence variation occurring when a single nucleotide in the genome (or other shared sequence) differs between members of a species (or between paired chromosomes in an individual). SNPs may fall within coding sequences of genes, non-coding regions of genes, or in the intergenic regions between genes. SNPs within a coding sequence will not necessarily change the amino acid sequence of the protein that is produced, due to degeneracy of the genetic code. A SNP mutation that results in a new DNA sequence that encodes the same polypeptide sequence is termed synonymous (also referred to as a silent mutation). Conversely, a SNP mutation that results in a new DNA sequence that encodes a different polypeptide sequence is termed non-synonymous. SNPs that are not in protein-coding regions may still have consequences for gene splicing, transcription factor binding, or the sequence of non-coding RNA.

For the methods of the invention, SNPs occurring within non-coding RNA regions are particularly important because those regions contain regulatory sequences which are complementary to miRNA molecules and required for interaction with other regulatory factors. SNPs occurring within genomic sequences are transcibed into mRNA transcripts which are targeted by miRNA molecules for degradation or translational silencing. SNPs occurring within the 3' untranslated region (UTR) of the genomic sequence or mRNA of a gene are of particular importance to the methods of the invention.

MicroRNAs

Figure 2:
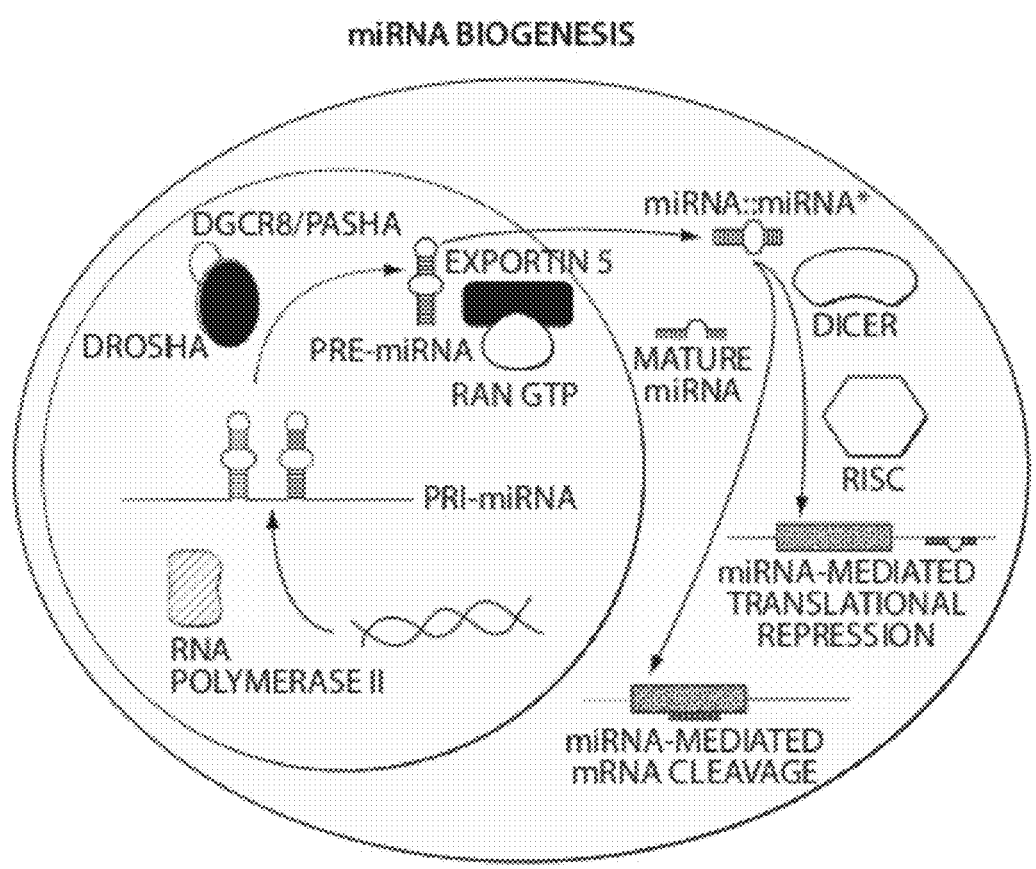
FIG. 2 is a schematic drawing showing transcription and processing of endogenous miRNA genes and precursor molecules.
Figure 4:
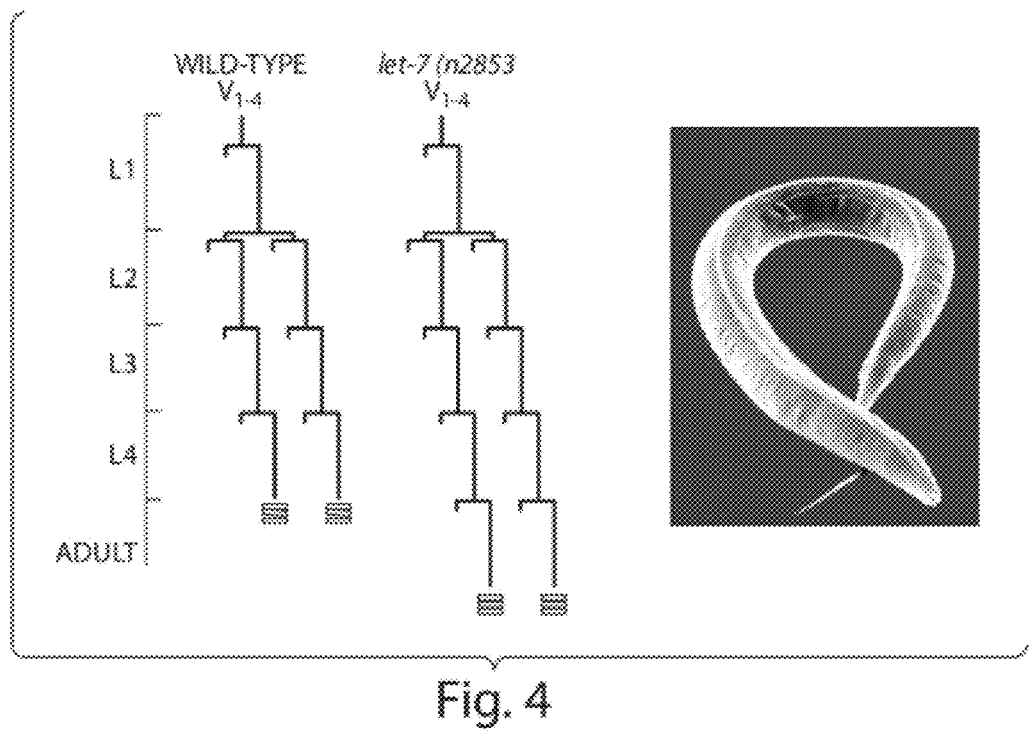
FIG. 4 is a schematic representation of let-7 miRNA function in cell cycle regulation showing a wild type and let-7 loss-of-function mutant C. elegans.
Figures 1, 8:
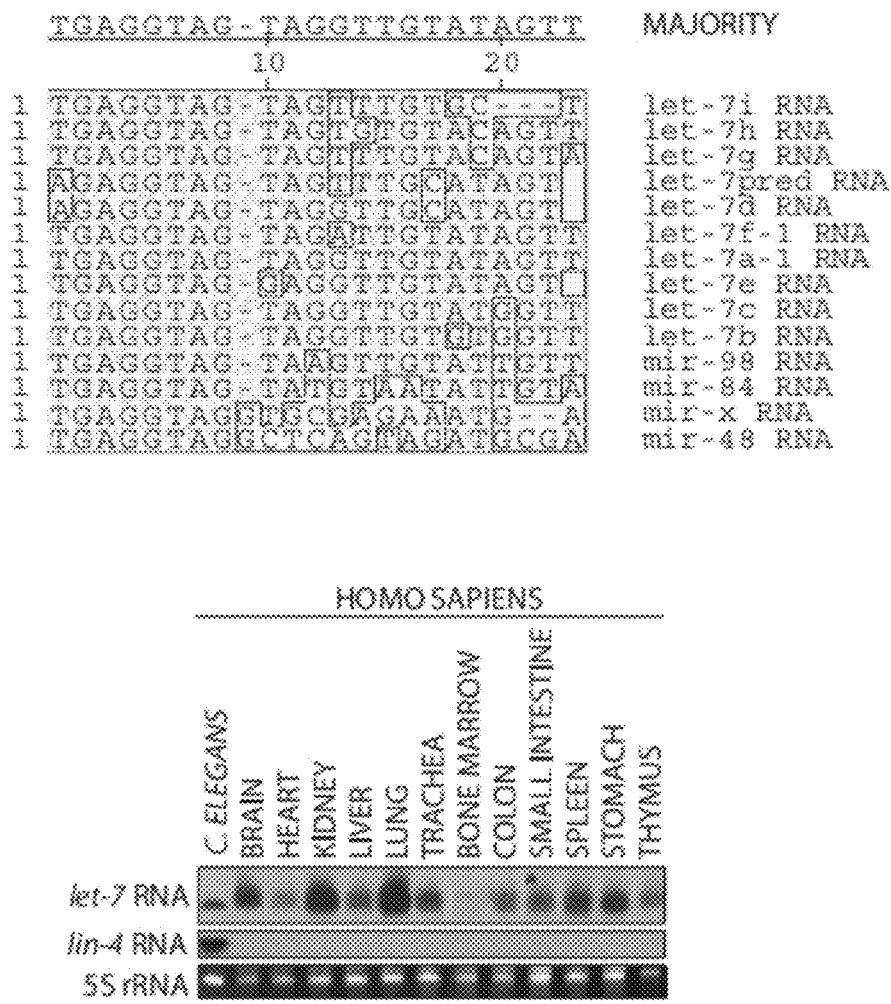
FIG. 8 provides sequence, structure, and expression pattern comparisons among members of the let-7 family of miRNAs in *C. elegans, D. melanogaster*, and *H. sapiens*. 8-1 provides the following let-7 family miRNA sequences: TGAGGTAG-TAGGTTGTATAGTT (SEQ ID NO: 58, MAJORITY), TGAGGTAGTAGTTTGTGC (SEQ ID NO: 59, let-7i), TGAGGTAGTAGTGTGTACAGTT (SEQ ID NO: 60, let-7h), TGAGGTAGTAGTTTGTACAGTA (SEQ ID NO: 61, let-7g), AGAGGTAGTAGTTTGCATAGT (SEQ ID NO: 62, let-7pred), AGAGGTAGTAGGTTGCATAGT (SEQ ID NO: 63, let-7d), TGAGGTAGTAGATTGTATAGTT (SEQ ID NO: 64, let-7f-1), TGAGGTAGTAGGTTGTATAGTT (SEQ ID NO: 65, let-7a-1), TGAGGTAGGAGGTTGTATAGT (SEQ ID NO: 66, let-7e), TGAGGTAGTAGGTTGTATG-GTT (SEQ ID NO: 67, let-7c), TGAGGTAGTAGGTTGT-GTGGTT (SEQ ID NO: 68, let-7b), TGAGGTAGTAAGT-TGTATTGTT (SEQ ID NO: 69, mir-98), TGAGGTAGTATGTAATATTGTA (SEQ ID NO: 70, mir-84), TGAGGTAGGTGCGAGAAATG (SEQ ID NO: 71, mir-x), TGAGGTAGGCTCAGTAGATGCGA (SEQ ID NO: 72, mir-48). 8.2 provides the following let-7 miRNA sequences: UGAGGUAGUAGGUUGUAUAGUUUG-GAAUAUUACCACCGGUGAACUAUGCAAU-UUUCUACCUUACC (SEQ ID NO: 73, *C. ELEGANS*), UGAGGUAGUAGGUUGUAUAGUAGUAA-UUACACAUCAUACUAUACAAUGUGC-UAGCUUUCUU (SEQ ID NO: 74, *D. MELANOGASTER*), UGAGGUAGUAGGUUGUAUAGU-UUGGGGCUCUGCCCUGCUAUGGGAUAAC-UAUACAAUCUACUGUCUUUCC (SEQ ID NO: 75, *H. SAPIENS* chr. 22).
Figures 2, 8:
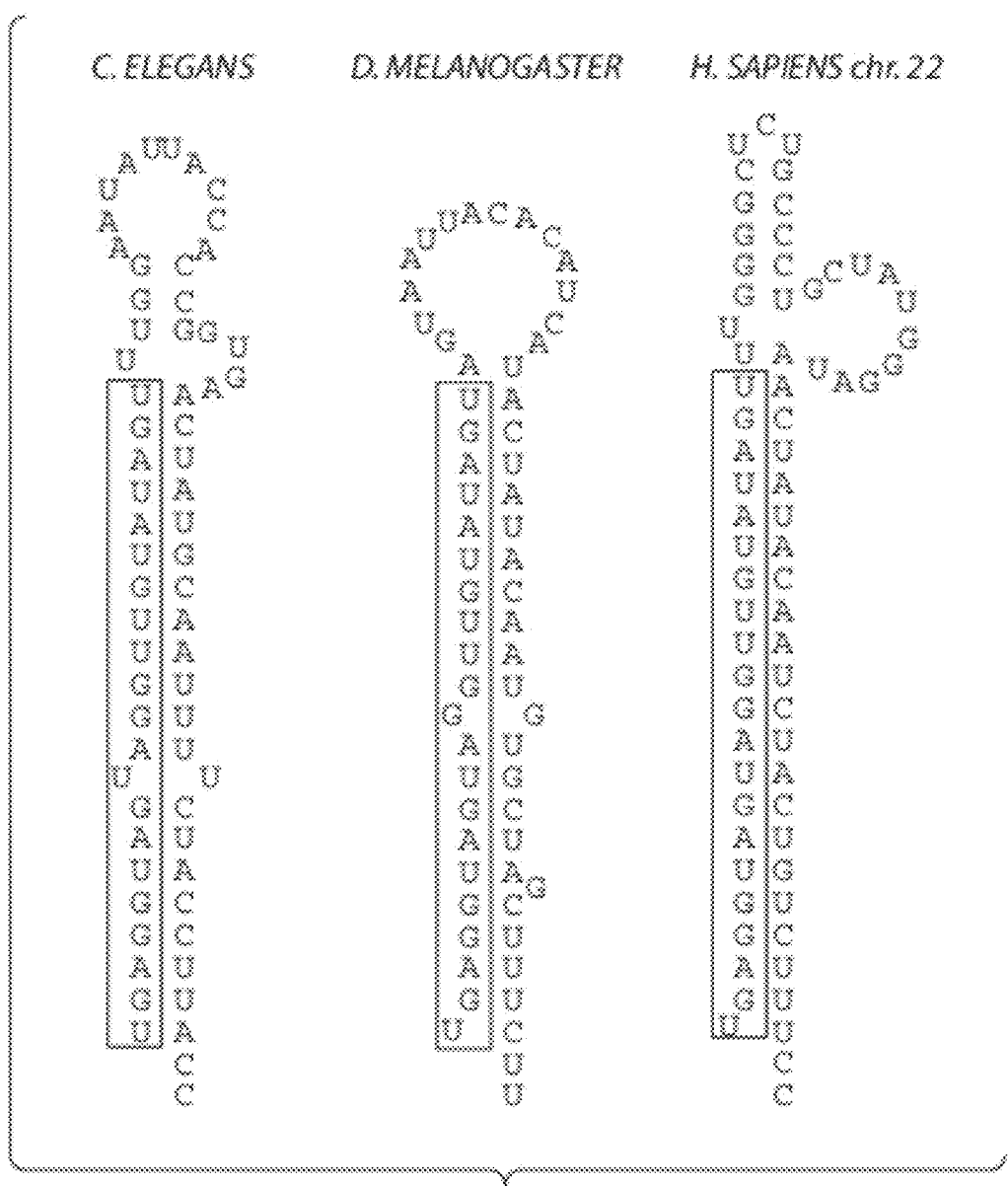
Figure 19A:
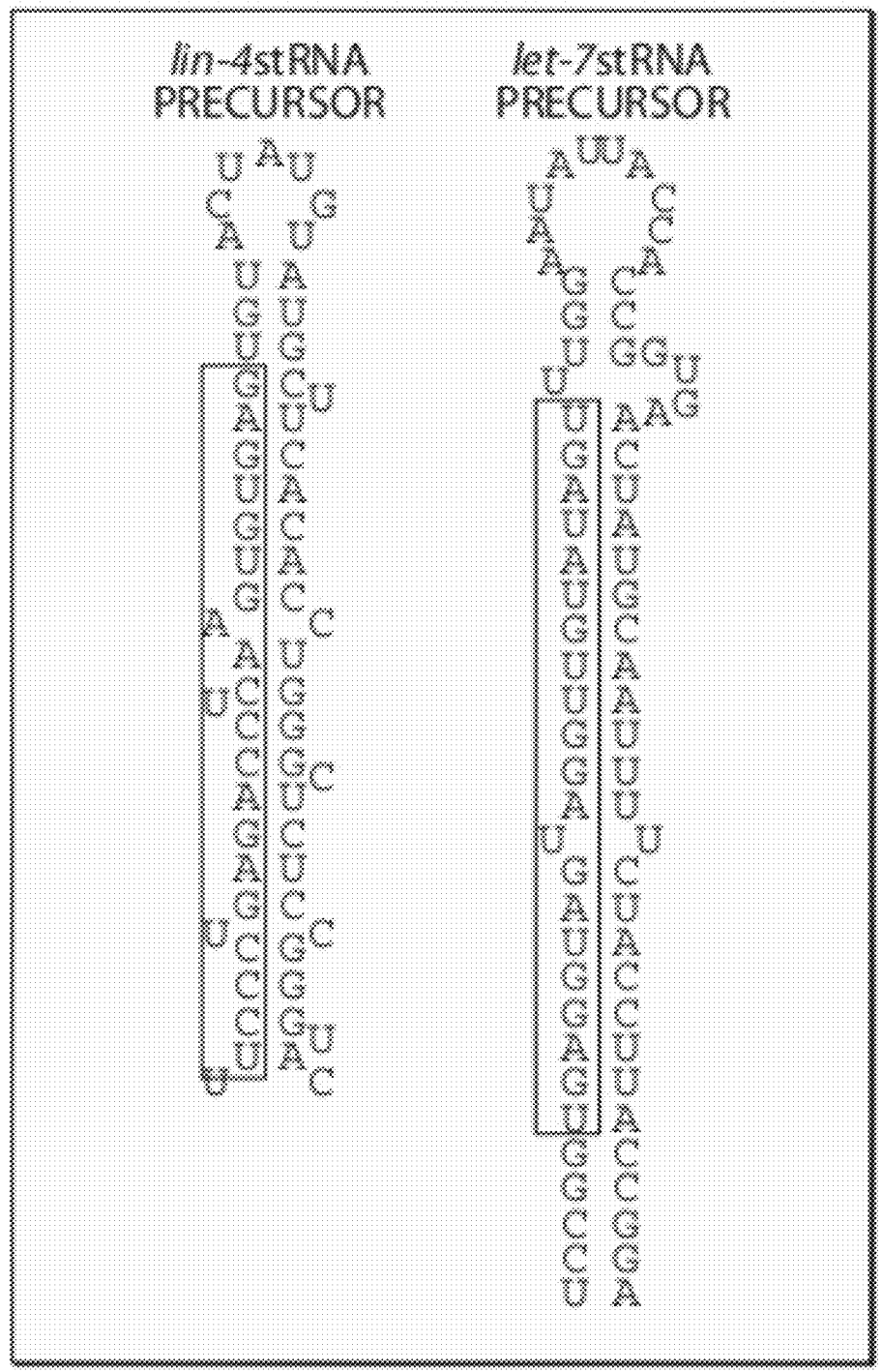
FIG. 19 provides schematic representations of let-7 and lin-4 miRNA sequences, target sequences, and functions. A. The following sequences are provided: UUCCCUGAGAC-CUCAAGUGUGAGUGUACUAUGUAUGCU-UCACACCUGGGCUCUCCGGGUAC (SEQ ID NO: 84, lin-4 stRNA PRECURSOR) and UCCGGUGAG-GUAGUAGGUUGUAUAGUUUGGAAUA-UUACCACCGGUGAACUAUGCAAUUUUC-UACCUUACCGGA (SEQ ID NO: 85, let-7 stRNA PRECURSOR). B. The following sequences are provided: CUCACACAACUCAGGAAU (SEQ ID NO: 86, lin-14), GAGUGUGACUCCAGAGUCCCUUG (SEQ ID NO: 87, LIN-4), UUAUACAACCCRUUCUACACUCA (SEQ ID NO: 88, lin-41), UGAUAUGUUGGAUGAUGGAGU (SEQ ID NO: 89, LET-7).
Figure 19B:
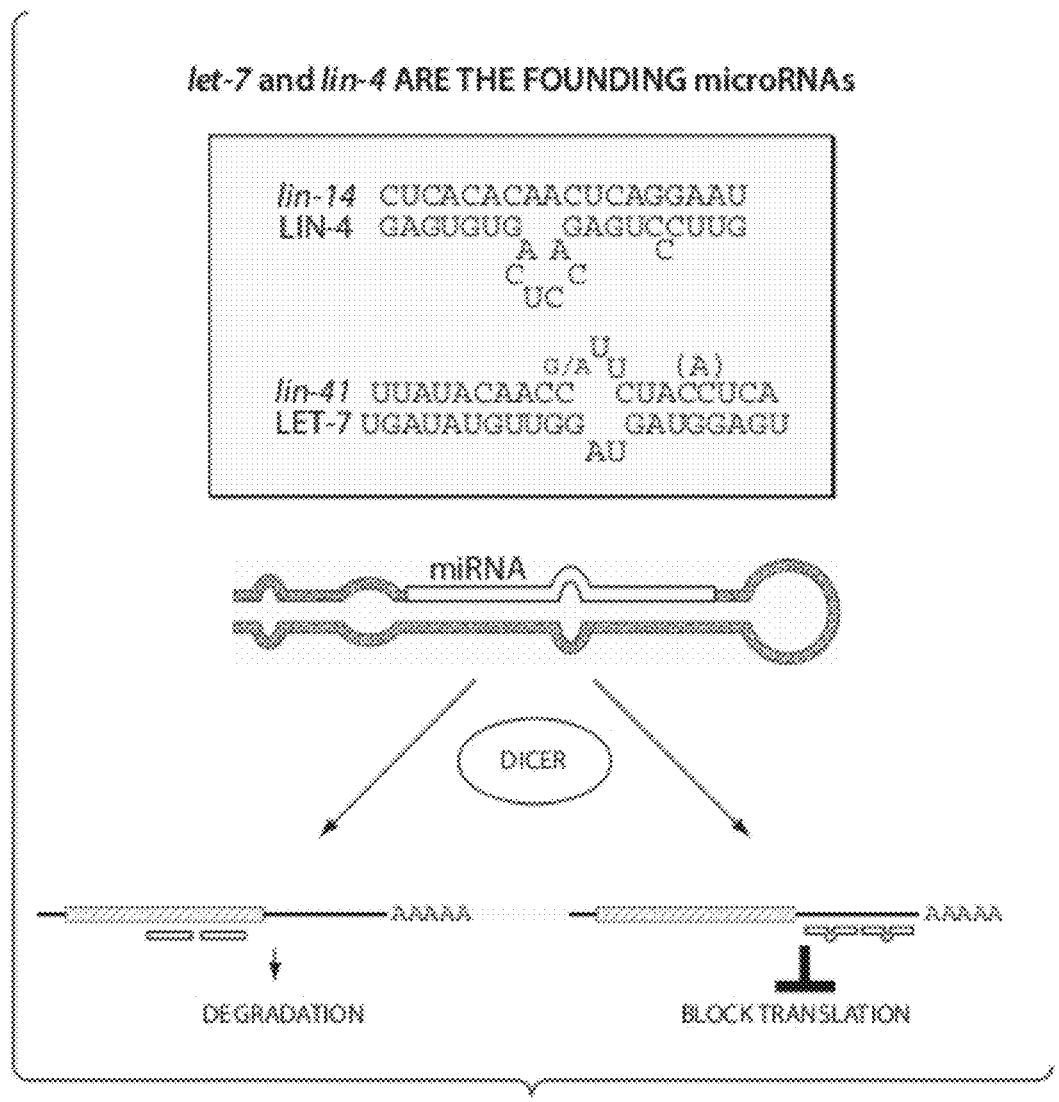

MicroRNAs (miRNAs) are small, non-coding RNAs, recently identified genetic regulators that control cell metabolism, development, cell cycle, cell differentiation and cell death (FIGS. 1 and 2). In addition, miRNAs have been found to be important in cancer, aging, and other disease states, likely due to their ability to regulate hundreds of genes targets. One of the first miRNAs to be identified was let-7 in *Caenorhabditis elegans* (*C. elegans*) (FIG. 19). In let-7 mutants, stem cells fail to exit the cell cycle and the animals burst through an organ known as the vulva (FIGS. 4 and 7). let-7 is highly conserved, even in humans (FIG. 8).

MiRNAs act by inhibiting translation of messenger RNA (mRNA) into protein by binding to the 3' untranslated region (UTR) of their target mRNAs. It has been found that these microRNA binding sites in 3'UTRs are very highly conserved regions in humans, suggesting an important role in these regions in natural selection. The high degree of conservation of the 3'UTR supports the hypothesis that a disruption of this region would lead to disease. While not bound by theory, miRNAs inhibit mRNA translation by either causing mRNA degradation or inhibiting translation itself (FIG. 1).

MiRNAs are single-stranded RNA molecules of about 21-23 nucleotides in length. MiRNAs are encoded by endogenous and exogenous genes that are transcribed from DNA by RNA polymerase II, however, miRNA are never translated into polypeptide sequences (FIG. 2). As such, miRNA are considered in the art as "non-coding RNA." The term "endogenous" gene as used herein is meant to encompass all genes that naturally occur within the genome of an individual. The term "exogenous" gene as used herein is meant to encompass all genes that do not naturally occur within the genome of an individual. For example, a miRNA could be introduced exogenously by a virus.

While not limited by theory, the present invention includes and is based in part on the understanding that miRNA biogenesis occurs by the following mechanism. MiRNA are processed from primary mRNA transcipts, called "primiRNA" by the nuclease Drosha and the double-stranded RNA binding protein DGCR8/Pasha. Once processed, these transcipts form stem-loop structures referred to as "premiRNA" (FIG. 2). Pre-miRNA are processed one step further by the endonuclease Dicer, which transforms the double-stranded pre-miRNA molecules into the single-stranded mature miRNA and initiates formation of the RNA-induced silencing complex (RISC). One of the two resulting single-stranded complementary miRNA strands, the guide strand, is selected by the argonaute protein of the RISC and incorporated into the RISC, while the other strand, the anti-guide or passenger strand, is degraded. Following integration into the RISC, miRNAs bind target mRNAs and subsequently inhibit translation.

MiRNAs are complementary to a part of one or more mRNAs. Moreover, miRNAs do not require absolute sequence complementarity to bind an mRNA, enabling them to regulate a wide range of target transcripts. In particular, miRNAs are frequently complementary to the 3' UTR of the mRNA transcript. Alternatively, or in addition, miRNAs also target methylation genomic sites which may correspond to genes encoding targeted mRNAs. The methylation state of genomic DNA in part determines the accessibility of that DNA to transcription factors. As such, DNA methylation and de-methylation regulate gene silencing and expression, respectively.

Oncogenic and Tumor Suppressor MiRNAs

MiRNAs that silence expression of tumor suppressor genes are oncogenes. Alternatively, miRNAs are tumor suppressor genes, which silence the translation of mRNAs transcripts of oncogenes. The term "oncogene" as used herein is meant to encompass any gene that, when expressed, directly or indirectly, causes a cell to inappropriately enter the cell cycle. Exemplary oncogenes include, but are not limited to, growth factors, transcription factors, regulatory proteins, e.g. GTPases and receptors, and cell cycle proteins. The term "proto-oncogene" as used herein is meant to encompass any gene, that if modified, directly or indirectly, causes a cell to inappropriately enter the cell cycle. Examples of proto-oncogenes include, but are not limited to, RAS, WNT, MYC, ERK and TRK. The term "tumor supressor gene" as used herein encompasses any gene that repressed or silenced, leads deregulated cell division and/or overexpression of a proto-oncogene or oncogene. Exemplary tumor suppressor genes include, but are not limited to, retinoblastoma (encoding the Rb protein), TP53 (encoding the p53 protein), PTEN, APC, and CD95. Tumor supressor gene products repress genes that are essential for the continuing of the cell cycle. Effectively, if these genes are expressed, the cell cycle will not continue, effectively inhibiting cell division. Tumor suppressor gene products couple the cell cycle to DNA damage. Thus, these gene products activate cell cycle checkpoints and DNA repair mechanisms that stall or prevent cell division. If the damage cannot be repaired, the cell initiate apoptosis, or programmed cell death. Some tumor supressor gene products are involved in cell adhesion, and thus, prevent tumor cells from dispersing, block loss of contact inhibition, and inhibit metastasis. These proteins are also known as metastasis suppressors.

Figure 3:
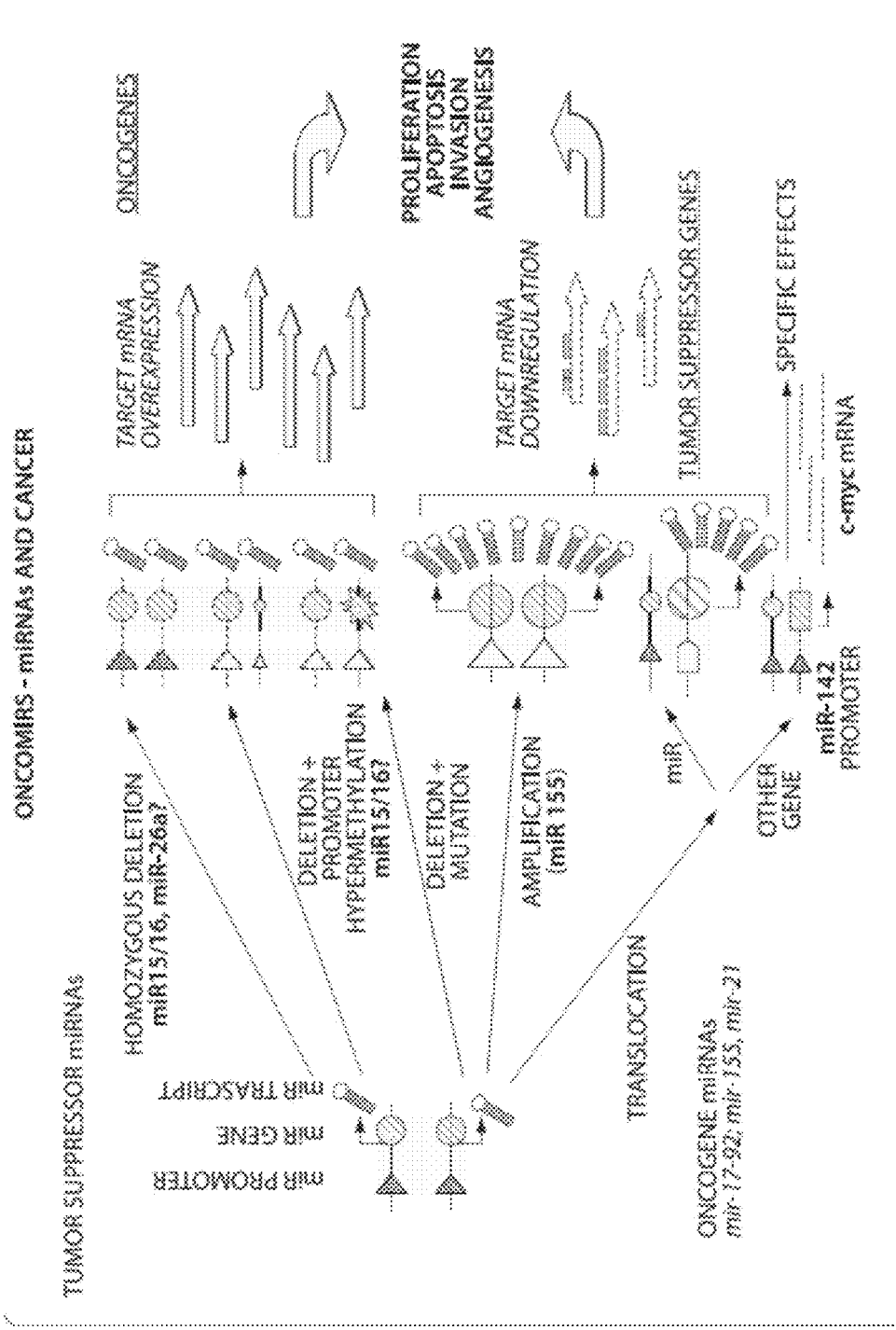
FIG. 3 is a schematic representation of role of miRNA molecules as oncogenes and tumor suppressor genes.

SNPs within the binding site of a tumor suppressing miRNA that decrease binding efficacy, and therefore oncogene silencing, lead to an increased risk, susceptibility or probability of presenting one or more symptoms of a cell proliferative disease (FIG. 3). Similarly, SNPs within the binding site of an oncogenic miRNA that increase binding, and therefore increase gene repression, lead to an increased risk, susceptibility or probability of presenting one or more symptoms of a cell proliferative disease (FIG. 3).

The invention comprises methods of screening for mutations within miRNA binding sites that lead to the development of a cell proliferative disorder. Therefore, methods of the invention comprise all known tumor suppressor and oncogenic miRNAs. Moreover, all endogenous human miRNAs are encompassed by the invention, the names, sequences, and targets of which are provided at the following database: The Wellcome Trust Sanger Institute MicroRNA Listing for *Homo sapiens*, the entirety of which is herein incorporated by reference.

RAS Gene Superfamily

The RAS gene encodes for a protein belongs to a larger superfamily of small GTPases that include the Ras, Rho, Arf, Rab, and Ran families. Functionally, GTPase proteins are molecular switches for a wide variety of signal transduction pathways that control practically every function within a cell. Exemplary functions regulated by GTPase proteins are cytoskeletal integrity, cell proliferation, cell adhesion, apoptosis, and cell migration. Thus, Ras protein deregulated within a cell often leads to increased cell invasion, metastasis, and decreased apoptosis. Importantly, Ras protein is attached to the cell membrane by prenylation and couples growth factor receptors to downstream mitogenic effectors involved in cell proliferation or differentiation.

There are three human RAS genes comprising HRAS, KRAS, and NRAS. Each gene comprises multiple miRNA complementary sites in the 3'UTR of their mRNA transcripts. Specifically, each human RAS gene comprises multiple let-7 complementary sites (LCSs).

Importantly, KRAS is capable of acting as either a tumor suppressor gene, a proto-oncogene, or an oncogene. SNPs in the 3'UTR of KRAS may lead to either increased or decreased binding efficacy of miRNAs. In one embodiment, KRAS acts as a proto-oncogene or oncogene, the SNP decreases the binding efficacy of at least one miRNA, causing expressing of the oncogene to be augmented, and the SNP is a marker of cell proliferative disease. In another embodiment, KRAS acts as a tumor suppressor gene, the SNP increases the binding efficacy of at least one miRNA, causing expression of the tumor suppressor gene to be repressed, and the SNP is a marker of cell proliferative disease. In either scenario, subjects who carry this marker are identified as having a greater risk of developing a cell proliferative disorder. Alternatively, or in addition, the occurrence of this SNP is predictive of the occurrence of a cell proliferative disorder.

The present invention comprises SNPs within any region of a human RAS family gene. In a preferred embodiment, SNPs occur within the 3' UTR of a RAS family gene. In another preferred embodiment, SNPs occur within the 3'UTR of KRAS. Exemplary human RAS sequences are included below, however, all known human RAS sequences are encompassed by the invention.

Human HRAS, transcript variant 1, is encoded by the following mRNA sequence (NCBI Accession No. NM_005343 and SEQ ID NO: 22) (untranslated regions are bolded):

```
   1 tgccctgcgc cgcaacccg agccgcaccc gccgcggacg gagcccatgc gcggggcgaa
  61 ccgcgcgccc ccgccccgc cccgccccgg cctcggcccc ggccctggcc ccggggcag
 121 tcgcgcctgt gaacggtggg gcaggagacc ctgtaggagg accccgggcc gcaggcccct
 181 gaggagcgat gacggaatat aagctggtgg tggtgggcgc cggcggtgtg ggcaagagtg
 241 cgctgaccat ccagctgatc cagaaccatt ttgtggacga atacgacccc actatagagg
 301 attcctaccg gaagcaggtg gtcattgatg gggagacgtg cctgttggac atcctggata
 361 ccgccggcca ggaggagtac agcgccatgc gggaccagta catgcgcacc ggggagggct
 421 tcctgtgtgt gtttgccatc aacaacacca agtcttttga ggacatccac cagtacaggg
 481 agcagatcaa acgggtgaag gactcggatg acgtgcccat ggtgctggtg gggaacaagt
 541 gtgacctggc tgcacgcact gtggaatctc ggcaggctca ggacctcgcc cgaagctacg
 601 gcatccccta catcgagacc tcggccaaga cccggcaggg agtggaggat gccttctaca
 661 cgttggtgcg tgagatccgg cagcacaagc tgcggaagct gaaccctcct gatgagagtg
 721 gccccggctc atgagctgc aagtgtgtgc tctcctgacg cagcacaagc tcaggacatg
 781 gaggtgccgg atgcaggaag gaggtgcaga cggaaggagg aggaaggaag gacggaagca
 841 aggaaggaag gaagggctgc tggagcccag tcaccccggg accgtgggcc gaggtgactg
 901 cagaccctcc cagggaggct gtgcacagac tgtcttgaac atcccaaatg ccaccggaac
 961 cccagccctt agctccctc ccaggcctct gtgggccctt gtcgggcaca gatgggatca
1021 cagtaaatta ttggatggtc ttgaaaaaaa aaaaaaaaa a
```

Human HRAS, transcript variant 2, is encoded by the following mRNA sequence (NCBI Accession No. NM_176795 and SEQ ID NO: 23) (untranslated regions are bolded):

```
   1 tgccctgcgc ccgcaacccg agccgcaccc gccgcggacg gagcccatgc gcggggcgaa
  61 ccgcgcgccc ccgccccgc cccgccccgg cctcggcccc ggccctggcc ccggggcag
 121 tcgcgcctgt gaacggtggg gcaggagacc ctgtaggagg accccgggcc gcaggcccct
 181 gaggagcgat gacggaatat aagctggtgg tggtgggcgc cggcggtgtg ggcaagagtg
 241 cgctgaccat ccagctgatc cagaaccatt ttgtggacga atacgacccc actatagagg
 301 attcctaccg gaagcaggtg gtcattgatg gggagacgtg cctgttggac atcctggata
 361 ccgccggcca ggaggagtac agcgccatgc gggaccagta catgcgcacc ggggagggct
 421 tcctgtgtgt gtttgccatc aacaacacca agtcttttga ggacatccac cagtacaggg
 481 agcagatcaa acgggtgaag gactcggatg acgtgcccat ggtgctggtg gggaacaagt
 541 gtgacctggc tgcacgcact gtggaatctc ggcaggctca ggacctcgcc cgaagctacg
 601 gcatccccta catcgagacc tcggccaaga cccggcaggg cagccgctct ggctctagct
 661 ccagctccgg gaccctctgg gaccccccgg gacccatgtg acccagcggc ccctcgcgct
 721 ggagtggagg atgccttcta cacgttggtg cgtgagatcc ggcagcacaa gctgcggaag
 781 ctgaaccctc ctgatgagag tggccccggc tgcatgagct gcaagtgtgt gctctcctga
 841 cgcagcacaa gctcaggaca tggaggtgcc ggatgcagga aggaggtgca gacggaagga
 901 ggaggaagga aggacggaag caaggaagga aggaagggct gctggagccc agtcaccccg
 961 ggaccgtggg ccgaggtgac tgcagaccct cccaggagg ctgtgcacag actgtcttga
1021 acatcccaaa tgccaccgga accccagccc ttagctcccc tcccaggcct ctgtgggccc
```

```
1081 ttgtcgggca cagatgggat cacagtaaat tattggatgg tcttgaaaaa aaaaaaaaaa 1141 aaa
```

Human KRAS, transcript variant a, is encoded by the following mRNA sequence (NCBI Accession No. NM_033360 and SEQ ID NO: 24) (untranslated regions are bolded, LCS6 is underlined):

```
   1 ggccgcggcg gcggaggcag cagcggcggc ggcagtggcg gcggcgaagg tggcggcggc
  61 tcggccagta ctcccggccc ccgccatttc ggactgggag cgagcgcggc gcaggcactg
 121 aaggcggcgg cggggccaga ggctcagcgg ctcccaggtg cgggagagag gcctgctgaa
 181 aatgactgaa tataaacttg tggtagttgg agctggtggc gtaggcaaga gtgccttgac
 241 gatacagcta attcagaatc attttgtgga cgaatatgat ccaacaatag aggattccta
 301 caggaagcaa gtagtaattg atggagaaac ctgtctcttg gatattctcg acacagcagg
 361 tcaagaggag tacagtgcaa tgagggacca gtacatgagg actggggagg gctttctttg
 421 tgtatttgcc ataaataata ctaaatcatt tgaagatatt caccattata gagaacaaat
 481 taaaagagtt aaggactctg aagatgtacc tatggtccta gtaggaaata atgtgatttg
 541 gccttctaga acagtagaca caaaacaggc tcaggactta gcaagaagtt atggaattcc
 601 ttttattgaa acatcagcaa agacaagaca gagagtggag gatgctttt atacattggt
 661 gagggagatc cgacaataca gattgaaaaa aatcagcaaa gaagaaaaga ctcctggctg
 721 tgtgaaaatt aaaaaatgca ttataatgta atctgggtgt tgatgatgcc ttctatacat
 781 tagttcgaga aattcgaaaa cataaagaaa agatgagcaa agatggtaaa agaagaaaa
 841 agaagtcaaa gacaaagtgt gtaattatgt aaatacaatt tgtactttt tcttaaggca
 901 tactagtaca agtggtaatt tttgtacatt acactaaatt attagcattt gttttagcat
 961 tacctaattt ttttcctgct ccatgcagac tgttagcttt taccttaaat gcttatttta
1021 aaatgacagt ggaagttttt ttttcctcta agtgccagta ttcccagagt tttggttttt
1081 gaactagcaa tgcctgtgaa aaagaaactg aatacctaag atttctgtct tggggttttt
1141 ggtgcatgca gttgattact tcttattttt cttaccaatt gtgaatgttg gtgtgaaaca
1201 aattaatgaa gcttttgaat catccctatt ctgtgtttta tctagtcaca taaatggatt
1261 aattactaat ttcagttgag accttctaat tggttttttac tgaaacattg agggaacaca
1321 aatttatggg cttcctgatg atgattcttc taggcatcat gtcctatagt ttgtcatccc
1381 tgatgaatgt aaagttacac tgttcacaaa ggttttgtct cctttccact gctattagtc
1441 atggtcactc tccccaaaat attatatttt ttctataaaa agaaaaaat ggaaaaaat
1501 tacaaggcaa tggaaactat tataaggcca tttccttttc acattagata aattactata
1561 aagactccta atagcttttc ctgttaaggc agacccagta tgaaatgggg attattatag
1621 caaccatttt ggggctatat ttacatgcta ctaaatttt ataataattg aaaagatttt
1681 aacaagtata aaaaattctc ataggaatta aatgtagtct ccctgtgtca gactgctctt
1741 tcatagtata actttaaatc ttttcttcaa cttgagtctt tgaagatagt tttaattctg
1801 cttgtgacat taaaagatta tttgggccag ttatagctta ttaggtgttg aagagaccaa
1861 ggttgcaagg ccaggccctg tgtgaaccttt tgagctttca tagagagttt cacagcatgg
1921 actgtgtccc cacggtcatc cagtgttgtc atgcattggt tagtcaaaat ggggagggac
1981 tagggcagtt tggatagctc aacaagatac aatctcactc tgtggtggtc ctgctgacaa
2041 atcaagagca ttgcttttgt ttcttaagaa aacaaactct ttttaaaaa ttacttttaa
2101 atattaactc aaaagttgag attttggggt ggtggtgtgc caagacatta attttttttt
```

```
-continued
2161 taaacaatga agtgaaaaag ttttacaatc tctaggtttg gctagttctc ttaacactgg
2221 ttaaattaac attgcataaa cacttttcaa gtctgatcca tatttaataa tgctttaaaa
2281 taaaaataaa aacaatcctt ttgataaatt taaaatgtta cttattttaa aataaatgaa
2341 gtgagatggc atggtgaggt gaaagtatca ctggactagg aagaaggtga cttaggttct
2401 agataggtgt cttttaggac tctgattttg aggacatcac ttactatcca tttcttcatg
2461 ttaaagaag tcatctcaaa ctcttagttt tttttttta caactatgta atttatattc
2521 catttacata aggatacact tatttgtcaa gctcagcaca atctgtaaat ttttaaccta
2581 tgttacacca tcttcagtgc cagtcttggg caaaattgtg caagaggtga agtttatatt
2641 tgaatatcca ttctcgtttt aggactcttc ttccatatta gtgtcatctt gcctccctac
2701 cttccacatg ccccatgact tgatgcagtt ttaatacttg taattcccct aaccataaga
2761 tttactgctg ctgtggatat ctccatgaag ttttcccact gagtcacatc agaaatgccc
2821 tacatcttat ttcctcaggg ctcaagaaaa tctgacagat accataaagg gatttgacct
2881 aatcactaat tttcaggtgg tggctgatgc tttgaacatc tctttgctgc ccaatccatt
2941 agcgacagta ggattttca aacctggtat gaatagacag aaccctatcc agtggaagga
3001 gaatttaata aagatagtgc tgaaagaatt ccttaggtaa tctataacta ggactactcc
3061 tggtaacagt aatacattcc attgttttag taaccagaaa tcttcatgca atgaaaaata
3121 ctttaattca tgaagcttac ttttttttt tggtgtcaga gtctcgctct tgtcacccag
3181 gctggaatgc agtggcgcca tctcagctca ctgcaacctc catctcccag gttcaagcga
3241 ttctcgtgcc tcggcctcct gagtagctgg gattacaggc gtgtgccact acactcaact
3301 aattttttgta tttttaggag agacgggggtt tcaccctgtt ggccaggctg gtctcgaact
3361 cctgacctca agt gattcac ccaccttggc ctcataaacc tgttttgcag aactcattta
3421 ttcagcaaat atttattgag tgcctaccag atgccagtca ccgcacaagg cactgggtat
3481 atggtatccc caaacaagag acataatccc ggtccttagg tagtgctagt gtggtctgta
3541 atatcttact aaggcctttg gtatacgacc cagagataac acgatgcgta tttttagtttt
3601 gcaaagaagg ggtttggtct ctgtgccagc tctataattg ttttgctacg attccactga
3661 aactcttcga tcaagctact ttatgtaaat cacttcattg ttttaaagga ataaacttga
3721 ttatattgtt tttttattg gcataactgt gattctttta ggacaattac tgtacacatt
3781 aaggtgtatg tcagatattc atattgaccc aaatgtgtaa tattccagtt ttctctgcat
3841 aagtaattaa aatatactta aaaattaata gttttatctg ggtacaaata aacaggtgcc
3901 tgaactagtt cacagacaag gaaacttcta tgtaaaaatc actatgattt ctgaattgct
3961 atgtgaaact acagatcttt ggaacactgt ttaggtaggg tgttaagact tacacagtac
4021 ctcgtttcta cacagagaaa gaaatggcca tacttcagga actgcagtgc ttatgagggg
4081 atatttaggc ctcttgaatt tttgatgtag atgggcattt ttttaaggta gtggttaatt
4141 acctttatgt gaactttgaa tggtttaaca aaagatttgt ttttgtagag attttaaagg
4201 gggagaattc tagaaataaa tgttacctaa ttattacagc cttaaagaca aaaatccttg
4261 ttgaagtttt tttaaaaaaa gctaaattac atagacttag gcattaacat gtttgtggaa
4321 gaatatagca gacgtatatt gtatcatttg agtgaatgtt cccaagtagg cattctaggc
4381 tctatttaac tgagtcacac tgcataggaa tttagaacct aactttata ggttatcaaa
4441 actgttgtca ccattgcaca atttttgtcct aatatataca tagaaacttt gtggggcatg
4501 ttaagttaca gtttgcacaa gttcatctca tttgtattcc attgatttt tttttcttct
```

```
-continued
4561 aaacattttt tcttcaaaca gtatataact ttttttaggg gatttttttt tagacagcaa 4621 aaactatctg aagatttcca tttgtcaaaa agtaatgatt tcttgataat tgtgtagtaa 4681 tgtttttag  aacccagcag ttaccttaaa gctgaattta tatttagtaa cttctgtgtt 4741 aatactggat agcatgaatt ctgcattgag aaactgaata gctgtcataa aatgaaactt 4801 tctttctaaa gaaagatact cacatgagtt cttgaagaat agtcataact agattaagat 4861 ctgtgtttta gtttaatagt ttgaagtgcc tgtttgggat aatgataggt aatttagatg 4921 aatttagggg aaaaaaaagt tatctgcaga tatgttgagg gcccatctct cccccacac 4981 cccacagag  ctaactgggt tacagtgttt tatccgaaag tttccaattc cactgtcttg 5041 tgttttcatg ttgaaaatac ttttgcattt ttcctttgag tgccaatttc ttactagtac 5101 tatttcttaa tgtaacatgt ttacctggaa tgtattttaa ctattttgt  atagtgtaaa 5161 ctgaaacatg cacattttgt acattgtgct ttcttttgtg ggacatatgc agtgtgatcc 5221 agttgttttc catcatttgg ttgcgctgac ctaggaatgt tggtcatatc aaacattaaa 5281 aatgaccact cttttaattg aaattaactt ttaaatgttt ataggagtat gtgctgtgaa 5341 gtgatctaaa atttgtaata tttttgtcat gaactgtact actcctaatt attgtaatgt 5401 aataaaaata gttacagtga caaaaaaaaa aaaaaa
```

Human KRAS, transcript variant b, is encoded by the following mRNA sequence (NCBI Accession No. NM_004985 and SEQ ID NO: 25) (untranslated regions are bolded, LCS6 is underlined):

```
   1 ggccgcggcg gcggaggcag cagcggcggc ggcagtggcg gcggcgaagg tggcggcggc 61 tcggccagta ctcccggccc ccgccatttc ggactgggag cgagcgcggc gcaggcactg 121 aaggcggcgg cggggccaga ggctcagcgg ctcccaggtg cgggagagag gcctgctgaa 181 aatgactgaa tataaacttg tggtagttgg agctggtggc gtaggcaaga gtgccttgac 241 gatacagcta attcagaatc attttgtgga cgaatatgat ccaacaatag aggattccta 301 caggaagcaa gtagtaattg atggagaaac ctgtctcttg gatattctcg acacagcagg 361 tcaagaggag tacagtgcaa tgagggacca gtacatgagg actggggagg gctttctttg 421 tgtatttgcc ataaataata ctaaatcatt tgaagatatt caccattata gagaacaaat 481 taaaagagtt aaggactctg aagatgtacc tatggtccta gtaggaaata atgtgatttt 541 gccttctaga acagtagaca caaaacaggc tcaggactta gcaagaagtt atggaattcc 601 ttttattgaa acatcagcaa agacaagaca gggtgttgat gatgccttct atacattagt 661 tcgagaaatt cgaaaacata agaaaagat  gagcaaagat ggtaaaaaga agaaaaagaa 721 gtcaaagaca aagtgtgtaa ttatgtaaat acaatttgta cttttttctt aaggcatact 781 agtacaagtg gtaattttg  tacattacac taaattatta gcatttgttt tagcattacc 841 taattttttt cctgctccat gcagactgtt agcttttacc ttaaatgctt atttaaaat 901 gacagtggaa gttttttttt cctctaagtg ccagtattcc cagagttttg gttttgaac 961 tagcaatgcc tgtgaaaaag aaactgaata cctaagattt ctgtcttggg gttttggtg 1021 catgcagttg attacttctt attttctta  ccaattgtga atgttggtgt gaaacaaatt 1081 aatgaagctt tgaatcatc  cctattctgt gttttatcta gtcacataaa tggattaatt 1141 actaatttca gttgagacct tctaattggt ttttactgaa acattgaggg aacacaaatt 1201 tatgggcttc ctgatgatga ttcttctagg catcatgtcc tatagtttgt catccctgat 1261 gaatgtaaag ttacactgtt cacaaaggtt ttgtctcctt tccactgcta ttagtcatgg 1321 tcactctccc caaaatatta tattttttct ataaaaagaa aaaaatggaa aaaaattaca
```

-continued

```
1381 aggcaatgga aactattata aggccatttc cttttcacat tagataaatt actataaaga 1441 ctcctaatag cttttcctgt taaggcagac ccagtatgaa atggggatta ttatagcaac 1501 cattttgggg ctatatttac atgctactaa attttttataa taattgaaaa gattttaaca 1561 agtataaaaa attctcatag gaattaaatg tagtctccct gtgtcagact gctctttcat 1621 agtataactt taaatctttt cttcaacttg agtctttgaa gatagtttta attctgcttg 1681 tgacattaaa agattatttg ggccagttat agcttattag gtgttgaaga gaccaaggtt 1741 gcaaggccag gccctgtgtg aacctttgag ctttcataga gagtttcaca gcatggactg 1801 tgtccccacg gtcatccagt gttgtcatgc attggttagt caaaatgggg agggactagg 1861 gcagtttgga tagctcaaca agatacaatc tcactctgtg gtggtcctgc tgacaaatca 1921 agagcattgc ttttgtttct taagaaaaca aactcttttt taaaaattac ttttaaatat 1981 taactcaaaa gttgagattt tggggtggtg gtgtgccaag acattaattt tttttttaaa 2041 caatgaagtg aaaaagtttt acaatctcta ggtttggcta gttctcttaa cactggttaa 2101 attaacattg cataaacact tttcaagtct gatccatatt taataatgct ttaaaataaa 2161 aataaaaaca atccttttga taaatttaaa atgttactta ttttaaaata aatgaagtga 2221 gatggcatgg tgaggtgaaa gtatcactgg actaggaaga aggtgactta ggttctagat 2281 aggtgtctttt taggactctg attttgagga catcacttac tatccatttc ttcatgttaa 2341 aagaagtcat ctcaaactct tagttttttt tttttacaac tatgtaattt atattccatt 2401 tacataagga tacacttatt tgtcaagctc agcacaatct gtaaatttt aacctatgtt 2461 acaccatctt cagtgccagt cttgggcaaa attgtgcaag aggtgaagtt tatatttgaa 2521 tatccattct cgttttagga ctcttcttcc atattagtgt catcttgcct ccctaccttc 2581 cacatgcccc atgacttgat gcagttttaa tacttgtaat tcccctaacc ataagattta 2641 ctgctgctgt ggatatctcc atgaagtttt cccactgagt cacatcagaa atgccctaca 2701 tcttatttcc tcagggctca agagaatctg acagatacca taaagggatt tgacctaatc 2761 actaattttc aggtggtggc tgatgctttg aacatctctt tgctgcccaa tccattagcg 2821 acagtaggat ttttcaaacc tggtatgaat agacagaacc ctatccagtg gaaggagaat 2881 ttaataaaga tagtgctgaa agaattcctt aggtaatcta taactaggac tactcctggt 2941 aacagtaata cattccattg ttttagtaac cagaaatctt catgcaatga aaatacttt 3001 aattcatgaa gcttactttt tttttttggt gtcagagtct cgctcttgtc acccaggctg 3061 gaatgcagtg gcgccatctc agctcactgc aacctccatc tcccaggttc aagcgattct 3121 cgtgcctcgg cctcctgagt agctgggatt acaggcgtgt gccactacac tcaactaatt 3181 tttgtatttt taggagagac ggggtttcac cctgttggcc aggctggtct cgaactcctg 3241 acctcaagtg attcacccac cttggcctca taaacctgtt ttgcagaact catttattca 3301 gcaaatattt attgagtgcc taccagatgc cagtcaccgc acaaggcact gggtatatgg 3361 tatccccaaa caagagacat aatcccggtc cttaggtagt gctagtgtgg tctgtaatat 3421 cttactaagg cctttggtat acgacccaga gataacacga tgcgtatttt agttttgcaa 3481 agaaggggtt tggtctctgt gccagctcta taattgtttt gctacgattc cactgaaact 3541 cttcgatcaa gctactttat gtaaatcact tcattgtttt aaaggaataa acttgattat 3601 attgtttttt tatttggcat aactgtgatt cttttaggac aattactgta cacattaagg 3661 tgtatgtcag atattcatat tgacccaaat gtgtaatatt ccagtttttct ctgcataagt 3721 aattaaaata tacttaaaaa ttaatagttt tatctgggta caaataaaca ggtgcctgaa
```

-continued

```
3781 ctagttcaca gacaaggaaa cttctatgta aaaatcacta tgatttctga attgctatgt 3841 gaaactacag atctttggaa cactgtttag gtagggtgtt aagacttaca cagtacctcg 3901 tttctacaca gagaaagaaa tggccatact tcaggaactg cagtgcttat gagggatat 3961 ttaggcctct tgaattttg atgtagatgg gcattttttt aaggtagtgg ttaattacct 4021 ttatgtgaac tttgaatggt ttaacaaaag atttgttttt gtagagattt taaagggga 4081 gaattctaga aataaatgtt acctaattat tacagcctta aagacaaaaa tccttgttga 4141 agtttttta aaaaagcta aattacatag acttaggcat taacatgttt gtggaagaat 4201 atagcagacg tatattgtat catttgagtg aatgttccca agtaggcatt ctaggctcta 4261 tttaactgag tcacactgca taggaatta gaacctaact tttataggtt atcaaaactg 4321 ttgtcaccat tgcacaattt tgtcctaata tatacataga aactttgtgg ggcatgttaa 4381 gttacagttt gcacaagttc atctcatttg tattccattg attttttttt tcttctaaac 4441 attttttctt caaacagtat ataacttttt ttaggggatt tttttttaga cagcaaaac 4501 tatctgaaga tttccatttg tcaaaagta atgatttctt gataattgtg tagtaatgtt 4561 ttttagaacc cagcagttac cttaaagctg aatttatatt tagtaacttc tgtgttaata 4621 ctggatagca tgaattctgc attgagaaac tgaatagctg tcataaatg aaactttctt 4681 tctaaagaaa gatactcaca tgagttcttg aagaatagtc ataactagat taagatctgt 4741 gttttagttt aatagttga agtgcctgtt tgggataatg ataggtaatt tagatgaatt 4801 taggggaaaa aaaagttatc tgcagatatg ttgagggccc atctctcccc ccacaccccc 4861 acagagctaa ctgggttaca gtgttttatc cgaaagtttc caattccact gtcttgtgtt 4921 ttcatgttga aaatactttt gcattttcc tttgagtgcc aatttcttac tagtactatt 4981 tcttaatgta acatgttac ctggaatgta ttttaactat ttttgtatag tgtaaactga 5041 aacatgcaca ttttgtacat tgtgctttct tttgtgggac atatgcagtg tgatccagtt 5101 gttttccatc atttggttgc gctgacctag gaatgttggt catatcaaac attaaaaatg 5161 accactcttt taattgaaat taacttttaa atgtttatag gagtatgtgc tgtgaagtga 5221 tctaaaattt gtaatatttt tgtcatgaac tgtactactc ctaattattg taatgtaata 5281 aaaatagtta cagtgacaaa aaaaaaaaaa aa
```

Human KRAS, transcript variant a, comprising the LCS6 SNP, is encoded by the following mRNA sequence (SEQ ID NO: 26) (untranslated regions are bolded, LCS6 is underlined, SNP is capitalized):

```
  1 ggccgcggcg gcggaggcag cagcggcggc ggcagtggcg gcggcgaagg tggcggcggc 61 tcggccagta ctcccggccc ccgccatttc ggactgggag cgagcgcggc gcaggcactg 121 aaggcggcgg cggggccaga ggctcagcgg ctcccaggtg cgggagagag gcctgctgaa 181 aatgactgaa tataaacttg tggtagttgg agctggtggc gtaggcaaga gtgccttgac 241 gatacagcta attcagaatc attttgtgga cgaatatgat ccaacaatag aggattccta 301 caggaagcaa gtagtaattg atggagaaac ctgtctcttg gatattctcg acacagcagg 361 tcaagaggag tacagtgcaa tgagggacca gtacatgagg actggggagg gctttctttg 421 tgtatttgcc ataaataata ctaaatcatt tgaagatatt caccattata gagaacaaat 481 taaaagagtt aaggactctg aagatgtacc tatggtccta gtaggaaata atgtgatttt 541 gccttctaga acagtagaca caaaacaggc tcaggactta gcaagaagtt atggaattcc 601 ttttattgaa acatcagcaa agacaagaca gagagtggag gatgcttttt atacattggt 661 gagggagatc cgacaataca gattgaaaaa aatcagcaaa gaagaaaaga ctcctggctg
```

```
721  tgtgaaaatt aaaaaatgca ttataatgta atctgggtgt tgatgatgcc ttctatacat
781  tagttcgaga aattcgaaaa cataaagaaa agatgagcaa agatggtaaa aagaagaaaa
841  agaagtcaaa gacaaagtgt gtaattatgt aaatacaatt tgtacttttt tcttaaggca
901  tactagtaca agtggtaatt tttgtacatt acactaaatt attagcattt gtttagcat
961  tacctaattt ttttcctgct ccatgcagac tgttagcttt taccttaaat gcttatttta
1021 aaatgacagt ggaagttttt ttttcctcta agtgccagta ttcccagagt tttggttttt
1081 gaactagcaa tgcctgtgaa aaagaaactg aatacctaag atttctgtct tggggttttt
1141 ggtgcatgca gttgattact tcttattttt cttaccaatt gtgaatgttg gtgtgaaaca
1201 aattaatgaa gcttttgaat catccctatt ctgtgtttta tctagtcaca taaatggatt
1261 aattactaat ttcagttgag accttctaat tggttttttac tgaaacattg agggaacaca
1321 aatttatggg cttcctgatg atgattcttc taggcatcat gtcctatagt ttgtcatccc
1381 tgatgaatgt aaagttacac tgttcacaaa ggttttgtct cctttccact gctattagtc
1441 atggtcactc tccccaaaat attatatttt ttctataaaa agaaaaaaat ggaaaaaaat
1501 tacaaggcaa tggaaactat tataaggcca tttccttttc acattagata aattactata
1561 aagactccta atagcttttc ctgttaaggc agacccagta tgaaatgggg attattatag
1621 caaccatttt ggggctatat ttacatgcta ctaaatttt ataataattg aaaagatttt
1681 aacaagtata aaaaattctc ataggaatta aatgtagtct ccctgtgtca gactgctctt
1741 tcatagtata actttaaatc ttttcttcaa cttgagtctt tgaagatagt tttaattctg
1801 cttgtgacat taaaagatta tttgggccag ttatagctta ttaggtgttg aagagaccaa
1861 ggttgcaagg ccaggccctg tgtgaacctt tgagctttca tagagagttt cacagcatgg
1921 actgtgtccc cacggtcatc cagtgttgtc atgcattggt tagtcaaaat ggggagggac
1981 tagggcagtt tggatagctc aacaagatac aatctcactc tgtggtggtc ctgctgacaa
2041 atcaagagca ttgcttttgt ttcttaagaa acaaactct tttttaaaaa ttactttaa
2101 atattaactc aaaagttgag attttggggt ggtggtgtgc caagacatta attttttttt
2161 taaacaatga agtgaaaaag ttttacaatc tctaggtttg gctagttctc ttaacactgg
2221 ttaaattaac attgcataaa cacttttcaa gtctgatcca tatttaataa tgctttaaaa
2281 taaaaataaa aacaatcctt ttgataaatt taaaatgtta cttattttaa aataaatgaa
2341 gtgagatggc atggtgaggt gaaagtatca ctggactagg aagaaggtga cttaggttct
2401 agataggtgt cttttaggac tctgattttg aggacatcac ttactatcca tttcttcatg
2461 ttaaaagaag tcatctcaaa ctcttagttt ttttttttta caactatgta atttatattc
2521 catttacata aggatacact tatttgtcaa gctcagcaca atctgtaaat ttttaaccta
2581 tgttacacca tcttcagtgc cagtcttggg caaaattgtg caagaggtga agtttatatt
2641 tgaatatcca ttctcgtttt aggactcttc ttccatatta gtgtcatctt gcctccctac
2701 cttccacatg ccccatgact tgatgcagtt ttaatacttg taattcccct aaccataaga
2761 tttactgctg ctgtggatat ctccatgaag ttttcccact gagtcacatc agaaatgccc
2821 tacatcttat ttcctcaggg ctcaagagaa tctgacagat accataaagg gatttgacct
2881 aatcactaat tttcaggtgg tggctgatgc tttgaacatc tctttgctgc ccaatccatt
2941 agcgacagta ggatttttca aacctggtat gaatagacag aaccctatcc agtggaagga
3001 gaatttaata aagatagtgc tgaaagaatt cctaggtaa tctataacta ggactactcc
3061 tggtaacagt aatacattcc attgttttag taaccagaaa tcttcatgca atgaaaaata
```

```
3121 ctttaattca tgaagcttac ttttttttt tggtgtcaga gtctcgctct tgtcacccag 3181 gctggaatgc agtggcgcca tctcagctca ctgcaacctc catctcccag gttcaagcga 3241 ttctcgtgcc tcggcctcct gagtagctgg gattacaggc gtgtgccact acactcaact 3301 aattttttgta ttttttaggag agacggggtt tcaccctgtt ggccaggctg gtctcgaact 3361 cctgacctca agtgatGcac ccaccttggc ctcataaacc tgttttgcag aactcattta 3421 ttcagcaaat atttattgag tgcctaccag atgccagtca ccgcacaagg cactgggtat 3481 atggtatccc caaacaagag acataatccc ggtccttagg tagtgctagt gtggtctgta 3541 atatcttact aaggcctttg gtatacgacc cagagataac acgatgcgta ttttagtttt 3601 gcaaagaagg ggtttggtct ctgtgccagc tctataattg ttttgctacg attccactga 3661 aactcttcga tcaagctact ttatgtaaat cacttcattg ttttaaagga ataaacttga 3721 ttatattgtt tttttatttg gcataactgt gattcttta ggacaattac tgtacacatt 3781 aaggtgtatg tcagatattc atattgaccc aaatgtgtaa tattccagtt ttctctgcat 3841 aagtaattaa aatatactta aaaattaata gttttatctg ggtacaaata aacaggtgcc 3901 tgaactagtt cacagacaag gaaacttcta tgtaaaaatc actatgattt ctgaattgct 3961 atgtgaaact acagatcttt ggaacactgt ttaggtaggg tgttaagact tacacagtac 4021 ctcgtttcta cacagagaaa gaaatggcca tacttcagga actgcagtgc ttatgagggg 4081 atatttaggc ctcttgaatt tttgatgtag atgggcattt ttttaaggta gtggttaatt 4141 accttatgt gaactttgaa tggtttaaca aaagatttgt ttttgtagag atttttaaagg 4201 gggagaattc tagaaataaa tgttacctaa ttattacagc cttaaagaca aaaatccttg 4261 ttgaagtttt ttttaaaaaaa gctaaattac atagacttag gcattaacat gtttgtggaa 4321 gaatatagca gacgtatatt gtatcatttg agtgaatgtt cccaagtagg cattctaggc 4381 tctatttaac tgagtcacac tgcataggaa tttagaaccct aacttttata ggttatcaaa 4441 actgttgtca ccattgcaca attttgtcct aatatataca tagaaacttt gtggggcatg 4501 ttaagttaca gtttgcacaa gttcatctca tttgtattcc attgatttt ttttcttct 4561 aaacattttt tcttcaaaca gtatataact tttttttaggg gatttttttt tagacagcaa 4621 aaactatctg aagatttcca tttgtcaaaa agtaatgatt tcttgataat tgtgtagtaa 4681 tgttttttag aacccagcag ttaccttaaa gctgaattta tatttagtaa cttctgtgtt 4741 aatactggat agcatgaatt ctgcattgag aaactgaata gctgtcataa aatgaaactt 4801 tctttctaaa gaaagatact cacatgagtt cttgaagaat agtcataact agattaagat 4861 ctgtgttta gttaatagt ttgaagtgcc tgtttgggat aatgataggt aatttagatg 4921 aatttagggg aaaaaaaagt tatctgcaga tatgttgagg gcccatctct cccccacac 4981 ccccacagag ctaactgggt tacagtgttt tatccgaaag tttccaattc cactgtcttg 5041 tgttttcatg ttgaaaatac ttttgcattt ttcctttgag tgccaatttc ttactagtac 5101 tatttcttaa tgtaacatgt ttacctggaa tgtattttaa ctattttgt atagtgtaaa 5161 ctgaaacatg cacattttgt acattgtgct ttcttttgtg ggacatatgc agtgtgatcc 5221 agttgttttc catcatttgg ttgcgctgac ctaggaatgt tggtcatatc aaacattaaa 5281 aatgaccact ctttaattg aaattaactt ttaaatgttt ataggagtat gtgctgtgaa 5341 gtgatctaaa atttgtaata ttttttgtcat gaactgtact actcctaatt attgtaatgt 5401 aataaaaata gttacagtga caaaaaaaaa aaaaaa
```

Human KRAS, transcript variant b, comprising the LCS6 SNP, is encoded by the following mRNA sequence (SEQ ID NO: 27) (untranslated regions are bolded, LCS6 is underlined, SNP is capitalized):

```
   1 ggccgcggcg gcggaggcag cagcggcggc ggcagtggcg gcggcgaagg tggcggcggc
  61 tcggccagta ctcccggccc ccgccatttc ggactgggag cgagcgcggc gcaggcactg
 121 aaggcggcgg cggggccaga ggctcagcgg ctcccaggtg cgggagagag gcctgctgaa
 181 aatgactgaa tataaacttg tggtagttgg agctggtggc gtaggcaaga gtgccttgac
 241 gatacagcta attcagaatc attttgtgga cgaatatgat ccaacaatag aggattccta
 301 caggaagcaa gtagtaattg atggagaaac ctgtctcttg gatattctcg acacagcagg
 361 tcaagaggag tacagtgcaa tgagggacca gtacatgagg actggggagg gctttctttg
 421 tgtatttgcc ataaataata ctaaatcatt tgaagatatt caccattata gagaacaaat
 481 taaaagagtt aaggactctg aagatgtacc tatggtccta gtaggaaata atgtgattt
 541 gccttctaga acagtagaca caaacaggc tcaggactta gcaagaagtt atggaattcc
 601 ttttattgaa acatcagcaa agacaagaca gggtgttgat gatgccttct atacattagt
 661 tcgagaaatt cgaaaacata agaaaagat gagcaaagat ggtaaaaaga agaaaaagaa
 721 gtcaaagaca aagtgtgtaa ttatgtaaat acaatttgta cttttttctt aaggcatact
 781 agtacaagtg gtaattttg tacattacac taaattatta gcatttgttt tagcattacc
 841 taatttttt cctgctccat gcagactgtt agcttttacc ttaaatgctt attttaaaat
 901 gacagtggaa gttttttttt cctctaagtg ccagtattcc cagagttttg gttttttgaac
 961 tagcaatgcc tgtgaaaaag aaactgaata cctaagattt ctgtcttggg gtttttggtg
1021 catgcagttg attacttctt attttcctta ccaattgtga atgttggtgt gaaacaaatt
1081 aatgaagctt ttgaatcatc cctattctgt gttttatcta gtcacataaa tggattaatt
1141 actaatttca gttgagacct tctaattggt ttttactgaa acattgaggg aacacaaatt
1201 tatgggcttc ctgatgatga ttcttctagg catcatgtcc tatagtttgt catccctgat
1261 gaatgtaaag ttacactgtt cacaaaggtt ttgtctcctt tccactgcta ttagtcatgg
1321 tcactctccc caaaatatta tatttttct ataaaagaa aaaatggaa aaaattaca
1381 aggcaatgga aactattata aggccatttc cttttcacat tagataaatt actataaaga
1441 ctcctaatag cttttcctgt taaggcagac ccagtatgaa atggggatta ttatagcaac
1501 catttgggg ctatatttac atgctactaa attttataa taattgaaaa gatttttaaca
1561 agtataaaaa attctcatag gaattaaatg tagtctccct gtgtcagact gctctttcat
1621 agtataactt taaatctttt cttcaacttg agtctttgaa gatagtttta attctgcttg
1681 tgacattaaa agattatttg ggccagttat agcttattag gtgttgaaga gaccaaggtt
1741 gcaaggccag gccctgtgtg aacctttgag ctttcataga gagtttcaca gcatggactg
1801 tgtccccacg gtcatccagt gttgtcatgc attggttagt caaaatgggg agggactagg
1861 gcagtttgga tagctcaaca agatacaatc tcactctgtg gtggtcctgc tgacaaatca
1921 agagcattgc ttttgtttct taagaaaaca aactctttt taaaaattac ttttaaatat
1981 taactcaaaa gttgagattt tggggtggtg gtgtgccaag acattaattt tttttttaaa
2041 caatgaagtg aaaaagtttt acaatctcta ggtttggcta gttctcttaa cactggttaa
2101 attaacattg cataaacact tttcaagtct gatccatatt taataatgct ttaaaataa
2161 aataaaaaca atcctttga taaatttaaa atgttactta ttttaaaata aatgaagtga
2221 gatggcatgg tgaggtgaaa gtatcactgg actaggaaga aggtgactta ggttctagat
2281 aggtgtcttt taggactctg attttgagga catcacttac tatccatttc ttcatgttaa
```

-continued

```
2341 aagaagtcat ctcaaactct tagtttttt tttttacaac tatgtaattt atattccatt 2401 tacataagga tacacttatt tgtcaagctc agcacaatct gtaaattttt aacctatgtt 2461 acaccatctt cagtgccagt cttgggcaaa attgtgcaag aggtgaagtt tatatttgaa 2521 tatccattct cgttttagga ctcttcttcc atattagtgt catcttgcct ccctaccttc 2581 cacatgcccc atgacttgat gcagttttaa tacttgtaat tcccctaacc ataagattta 2641 ctgctgctgt ggatatctcc atgaagtttt cccactgagt cacatcagaa atgccctaca 2701 tcttatttcc tcagggctca agagaatctg acagatacca taaagggatt tgacctaatc 2761 actaattttc aggtggtggc tgatgctttg aacatctctt tgctgcccaa tccattagcg 2821 acagtaggat ttttcaaacc tggtatgaat agacagaacc ctatccagtg gaaggagaat 2881 ttaataaaga tagtgctgaa agaattcctt aggtaatcta taactaggac tactcctggt 2941 aacagtaata cattccattg ttttagtaac cagaaatctt catgcaatga aaatactttt 3001 aattcatgaa gcttactttt ttttttggt gtcagagtct cgctcttgtc acccaggctg 3061 gaatgcagtg gcgccatctc agctcactgc aacctccatc tcccaggttc aagcgattct 3121 cgtgcctcgg cctcctgagt agctgggatt acaggcgtgt gccactacac tcaactaatt 3181 tttgtatttt taggagagac ggggtttcac cctgttggcc aggctggtct cgaactcctg 3241 acctcaagtg atGcacccac cttggcctca taaacctgtt ttgcagaact catttattca 3301 gcaaatattt attgagtgcc taccagatgc cagtcaccgc acaaggcact gggtatatgg 3361 tatccccaaa caagagacat aatcccggtc cttaggtagt gctagtgtgg tctgtaatat 3421 cttactaagg cctttggtat acgacccaga gataacacga tgcgtatttt agttttgcaa 3481 agaaggggtt tggtctctgt gccagctcta taattgtttt gctacgattc cactgaaact 3541 cttcgatcaa gctactttat gtaaatcact tcattgtttt aaaggaataa acttgattat 3601 attgtttttt tatttggcat aactgtgatt cttttaggac aattactgta cacattaagg 3661 tgtatgtcag atattcatat tgacccaaat gtgtaatatt ccagtttcct ctgcataagt 3721 aattaaaata tacttaaaaa ttaatagttt tatctgggta caaataaaca ggtgcctgaa 3781 ctagttcaca gacaaggaaa cttctatgta aaaatcacta tgatttctga attgctatgt 3841 gaaactacag atctttggaa cactgtttag gtagggtgtt aagacttaca cagtacctcg 3901 tttctacaca gagaaagaaa tggccatact tcaggaactg cagtgcttat gaggggatat 3961 ttaggcctct tgaatttttg atgtagatgg gcatttttt aaggtagtgg ttaattacct 4021 ttatgtgaac tttgaatggt ttaacaaaag atttgttttt gtagagattt taaggggga 4081 gaattctaga aataaatgtt acctaattat tacagcctta aagacaaaaa tccttgttga 4141 agtttttta aaaaagcta aattacatag acttaggcat taacatgttt gtggaagaat 4201 atagcagacg tatattgtat catttgagtg aatgttccca gtaggcatt ctaggctcta 4261 tttaactgag tcacactgca taggaattta gaacctaact tttataggtt atcaaaactg 4321 ttgtcaccat tgcacaattt tgtcctaata tatacataga aactttgtgg ggcatgttaa 4381 gttacagttt gcacaagttc atctcatttg tattccattg attttttttt tcttctaaac 4441 atttttctct caaacagtat ataacttttt ttaggggatt ttttttaga cagcaaaaac 4501 tatctgaaga tttccatttg tcaaaagta atgatttctt gataattgtg tagtaatgtt 4561 ttttagaacc cagcagttac cttaaagctg aatttatatt tagtaacttc tgtgttaata 4621 ctggatagca tgaattctgc attgagaaac tgaatagctg tcataaaatg aaactttctt 4681 tctaaagaaa gatactcaca tgagttcttg aagaatagtc ataactagat taagatctgt 4741 gttttagttt aatagtttga agtgcctgtt tgggataatg ataggtaatt tagatgaatt
```

-continued

```
4801 taggggaaaa aaaagttatc tgcagatatg ttgagggccc atctctcccc ccacacccc
4861 acagagctaa ctgggttaca gtgttttatc cgaaagtttc caattccact gtcttgtgtt
4921 ttcatgttga aaatactttt gcattttcc tttgagtgcc aatttcttac tagtactatt
4981 tcttaatgta acatgtttac ctggaatgta ttttaactat ttttgtatag tgtaaactga
5041 aacatgcaca ttttgtacat tgtgctttct tttgtgggac atatgcagtg tgatccagtt
5101 gttttccatc atttggttgc gctgacctag gaatgttggt catatcaaac attaaaaatg
5161 accactcttt taattgaaat taactttaa atgtttatag gagtatgtgc tgtgaagtga
5221 tctaaaattt gtaatatttt tgtcatgaac tgtactactc ctaattattg taatgtaata
5281 aaaatagtta cagtgacaaa aaaaaaaaaa aa
```

Human NRAS is encoded by the following mRNA sequence (NCBI Accession No. NM_002524 and SEQ ID NO: 28) (untranslated regions are bolded):

```
   1 gaaacgtccc gtgtgggagg ggcgggtctg ggtgcggctg ccgcatgact cgtggttcgg
  61 aggcccacgt ggccggggcg gggactcagg cgcctggcag ccgactgatt acgtagcggg
 121 cggggccgga agtgccgctc cttggtgggg gctgttcatg gcggttccgg ggtctccaac
 181 attttccccg gtctgtggtc ctaaatctgt ccaaagcaga ggcagtggag cttgaggttc
 241 ttgctggtgt gaaatgactg agtacaaact ggtggtggtt ggagcaggtg tgttgggaa
 301 aagcgcactg acaatccagc taatccagaa ccactttgta gatgaatatg atcccaccat
 361 agaggattct tacagaaaac aagtggttat agatggtgaa acctgtttgt tggacatact
 421 ggatacagct ggacaagaag agtacagtgc catgagagac caatacatga ggacaggcga
 481 aggcttcctc tgtgtatttg ccatcaataa tagcaagtca tttgcggata ttaacctcta
 541 cagggagcag attaagcgag taaaagactc ggatgatgta cctatggtgc tagtgggaaa
 601 caagtgtgat ttgccaacaa ggacagttga tacaaaacaa gcccacgaac tggccaagag
 661 ttacgggatt ccattcattg aaacctcagc caagaccaga cagggtgttg aagatgcttt
 721 ttacacactg gtaagagaaa tacgccagta ccgaatgaaa aaactcaaca gcagtgatga
 781 tgggactcag ggttgtatgg gattgccatg tgtggtgatg taacaagata cttttaaagt
 841 tttgtcagaa aagagccact ttcaagctgc actgacaccc tggtcctgac ttcctggagg
 901 agaagtattc ctgttgctgt cttcagtctc acagagaagc tcctgctact tccccagctc
 961 tcagtagttt agtacaataa tctctatttg agaagttctc agaataacta cctcctcact
1021 tggctgtctg accagagaat gcacctcttg ttactccctg ttattttct gccctgggtt
1081 cttccacagc acaaacacac ctcaacacac ctctgccacc ccaggttttt catctgaaaa
1141 gcagttcatg tctgaaacag agaaccaaac cgcaaacgtg aaattctatt gaaaacagtg
1201 tcttgagctc taaagtagca actgctggtg attttttttt tcttttact gttgaactta
1261 gaactatgcc taatttttgg agaaatgtca taaattactg ttttgccaag aatatagtta
1321 ttattgctgt ttggtttgtt tataatgtta tcggctctat tctctaaact ggcatctgct
1381 ctagattcat aaatacaaaa atgaatactg aattttgagt ctatcctagt cttcacaact
1441 ttgacgtaat taaatccaac ttttcacagt gaagtgcctt tttcctagaa gtggtttgta
1501 gactccttta taatatttca gtggaataga tgtctcaaaa atccttatgc atgaaatgaa
1561 tgtctgagat acgtctgtga cttatctacc attgaaggaa agctatatct atttgagagc
1621 agatgccatt ttgtacatgt atgaaattgg ttttccagag gcctgttttg gggctttccc
```

```
1681  aggagaaaga  tgaaactgaa  agcatatgaa  taatttcact  taataatttt  tacctaatct 1741  ccacttttt   cataggttac  tacctataca  atgtatgtaa  tttgtttccc  ctagcttact 1801  gataaaccta  atattcaatg  aacttccatt  tgtattcaaa  tttgtgtcat  accagaaagc 1861  tctacatttg  cagatgttca  aatattgtaa  aactttggtg  cattgttatt  taatagctgt 1921  gatcagtgat  tttcaaacct  caaatatagt  atattaacaa  att
```

Let-7 Complementary Sites (LCS)

As used herein, the term "let-7 complementary site" is meant to describe any region of a gene or gene transcript that binds a member of the let-7 family of miRNAs. Moreover, this term encompasses those sequences within a gene or gene transcript that are complementary to the sequence of a let-7 family miRNA. The term "complementary" as used herein describes a threshold of binding between two sequences wherein a majority of nucleotides in each sequence are capable of binding to a majority of nucleotides within the other sequence in trans.

Figure 6A:
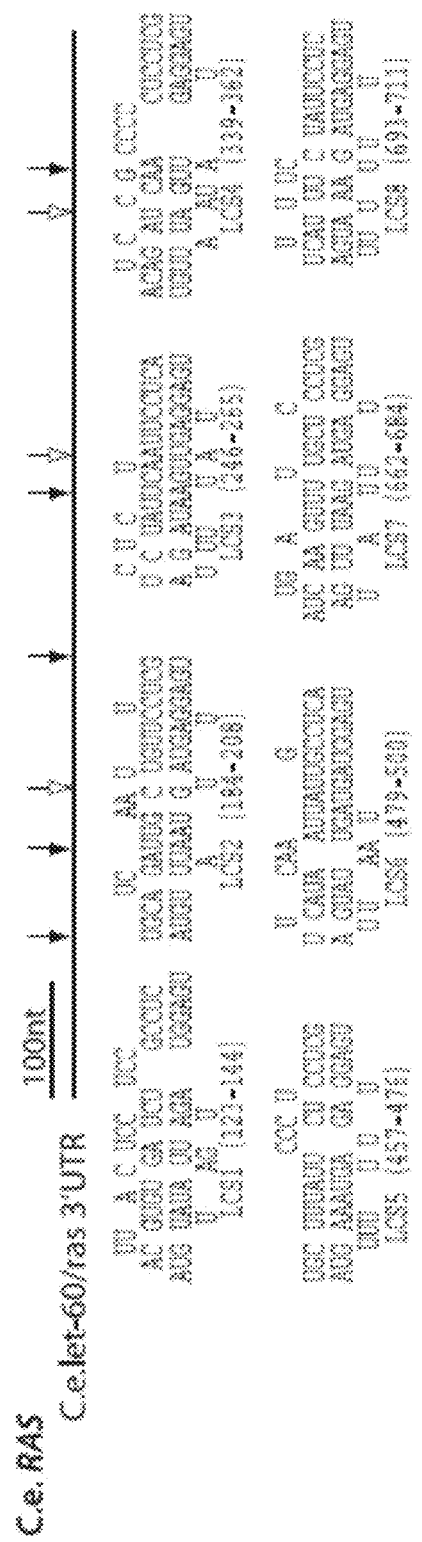
FIG. 6 is a schematic representation showing the let-7 miRNA complementary binding sites in C. elegans and Homo sapiens RAS oncogenes. A. As shown in LCS1, ACUUGUAGUCGAUCUCCUUCCGCCUC (SEQ ID NO: 47, top) is complementary to AUGUUAUAAUGUAUGAUGGAGU (SEQ ID NO: 48, bottom). As shown in LCS2, UGCAUCGAUUGAACUUGUUCUCUCG (SEQ ID NO: 49, top) is complementary to AUGUUAUAAUGUAUGAUGGAGU (SEQ ID NO: 48, bottom). As shown in LCS3, UCCUUCAUUCUAAUUCCUCA (SEQ ID NO: 50, top) is complementary to AUGUUAUAAUGUAUGAUGGAGU (SEQ ID NO: 48, bottom). As shown in LCS4, ACUAGCAUCCGAACCCCUCCUCG (SEQ ID NO: 51, top) is complementary to UGUUAUAAUGUAUGAUGGAGU (SEQ ID NO: 52, bottom). As shown in LCS5, UGCUUUAUUCCCCUUCCUCG (SEQ ID NO: 53, top) is complementary to AUGUUAUAAUGUAUGAUGGAGU (SEQ ID NO: 48, bottom). As shown in LCS6, UUCAUACAAAUUAUUGGCCUCA (SEQ ID NO: 54, top) is complementary to AUGUUAUAAUGUAUGAUGGAGU (SEQ ID NO: 48, bottom). As shown in LCS7, AUUCGAAAGUUUUUGCUCCCUCG (SEQ ID NO: 55, top) is complementary to AUGUUAUAAUGUAUGAUGGAGU (SEQ ID NO: 48, bottom). As shown in LCS8, UCUAUUUUUCCUAUUCCUC (SEQ ID NO: 56, top) is complementary to AUGUUAUAAUGUAUGAUGGAGU (SEQ ID NO: 48, bottom). B. As shown in LCS1, AGUUCUCAGAAUAACUACCUCCUCA (SEQ ID NO: 1, top) is complementary to UUGAUAUGUUGGAUGAUGGAGU (SEQ ID NO: 57, bottom). As shown in LCS2, GGCUGUCUGACCAGAGAAUGCACCUC (SEQ ID NO: 2, top) is complementary to UUGAUAUGUUGGAUGAUGGAGU (SEQ ID NO: 57, bottom). As shown in LCS3, ACAGCACAAACACACCUC (SEQ ID NO: 3, top) is complementary to UUGAUAUGUUGGAUGAUGGAGU (SEQ ID NO: 57, bottom). As shown in LCS4, AGCUGUGAUCAGUGAUUUUCAAACCYCA (SEQ ID NO: 4, top) is complementary to UUGAUAUGUUGGAUGAUGGAGU (SEQ ID NO: 57, bottom). As shown in LCS5, AAUUGCCUUCAAUCCCUUCUCACCCCACCUC (SEQ ID NO: 5, top) is complementary to UUGAUAUGUUGGAUGAUGGAGU (SEQ ID NO: 57, bottom). As shown in LCS6, AUCUAAAUACUUACUGAGGUCCUC (SEQ ID NO: 6, top) is complementary to UUGAUAUGUUGGAUGAUGGAGU (SEQ ID NO: 57, bottom). As shown in LCS7, AAUUUUCCUGAGGCUUAUCACCUCA (SEQ ID NO: 7, top) is complementary to UUGAUAUGUUGGAUGAUGGAGU (SEQ ID NO: 57, bottom). As shown in LCS8, GAUUGCUGAAAAGAAUUCUAGUUUACCUCA (SEQ ID NO: 8, top) is complementary to UUGAUAUGUUGGAUGAUGGAGU (SEQ ID NO: 57, bottom). As shown in LCS9, AACAGGAACUAUUGGCCUC (SEQ ID NO: 9, top) is complementary to UUGAUAUGUUGGAUGAUGGAGU (SEQ ID NO: 57, bottom). C. As shown in LCS1, GACAGUGGAAGUUUUUUUUCCUCG (SEQ ID NO: 10, top) is complementary to UUGAUAUGUUGGAUGAUGGAGU (SEQ ID NO: 57, bottom). As shown in LCS2, AUUAGUGUCAUCUUGCCUC (SEQ ID NO: 11, top) is complementary to UUGAUAUGUUGGAUGAUGGAGU (SEQ ID NO: 57, bottom). As shown in LCS3, AAUGCCUACAUCUUAUUUUCCUCA (SEQ ID NO: 12, top) is complementary to UUGAUAUGUUGGAUGAUGGAGU (SEQ ID NO: 57, bottom). As shown in LCS4, GGUUCAAGCGAUUCUCGUGCCUCG (SEQ ID NO: 13, top) is complementary to UUGAUAUGUUGGAUGAUGGAGU (SEQ ID NO: 57, bottom). As shown in LCS5, GGCUGGUCCGAACUCCUGACCUCA (SEQ ID NO: 14, top) is complementary to UUGAUAUGUUGGAUGAUGGAGU (SEQ ID NO: 57, bottom). As shown in LCS6, GAUUCACCCACCUUGGCCUCA (SEQ ID NO: 15, top) is complementary to UUGAUAUGUUGGAUGAUGGAGU (SEQ ID NO: 57, bottom). As shown in LCS7, GGGUGUUAAGACUUGACACAGUACCUCG (SEQ ID NO: 16, top) is complementary to UUGAUAUG- UUGGAUGAUGGAGU (SEQ ID NO: 57, bottom). As shown in LCS8, AGUGCUUAUGAGGGGAUAUUUAG-GCCUC (SEQ ID NO: 17, top) is complementary to UUGAUAUGUUGGAUGAUGGAGU (SEQ ID NO: 57, bottom). D. As shown in LCS1, GACCGUGGGCCGAG-GUGACUGCAGACCCUC (SEQ ID NO: 18, top) is complementary to UUGAUAUGUUGGAUGAUGGAGU (SEQ ID NO: 57, bottom). As shown in LCS2, GGAACCCCAGC-CCUUAGCUCCCCUC (SEQ ID NO: 19, top) is complementary to UUGAUAUGUUGGAUGAUGGAGU (SEQ ID NO: 57, bottom). As shown in LCS3, AGCCCUUAGCUC-CCCUCCCAGGCCUC (SEQ ID NO: 20, top) is complementary to UUGAUAUGUUGGAUGAUGGAGU (SEQ ID NO: 57, bottom).
Figure 6B:
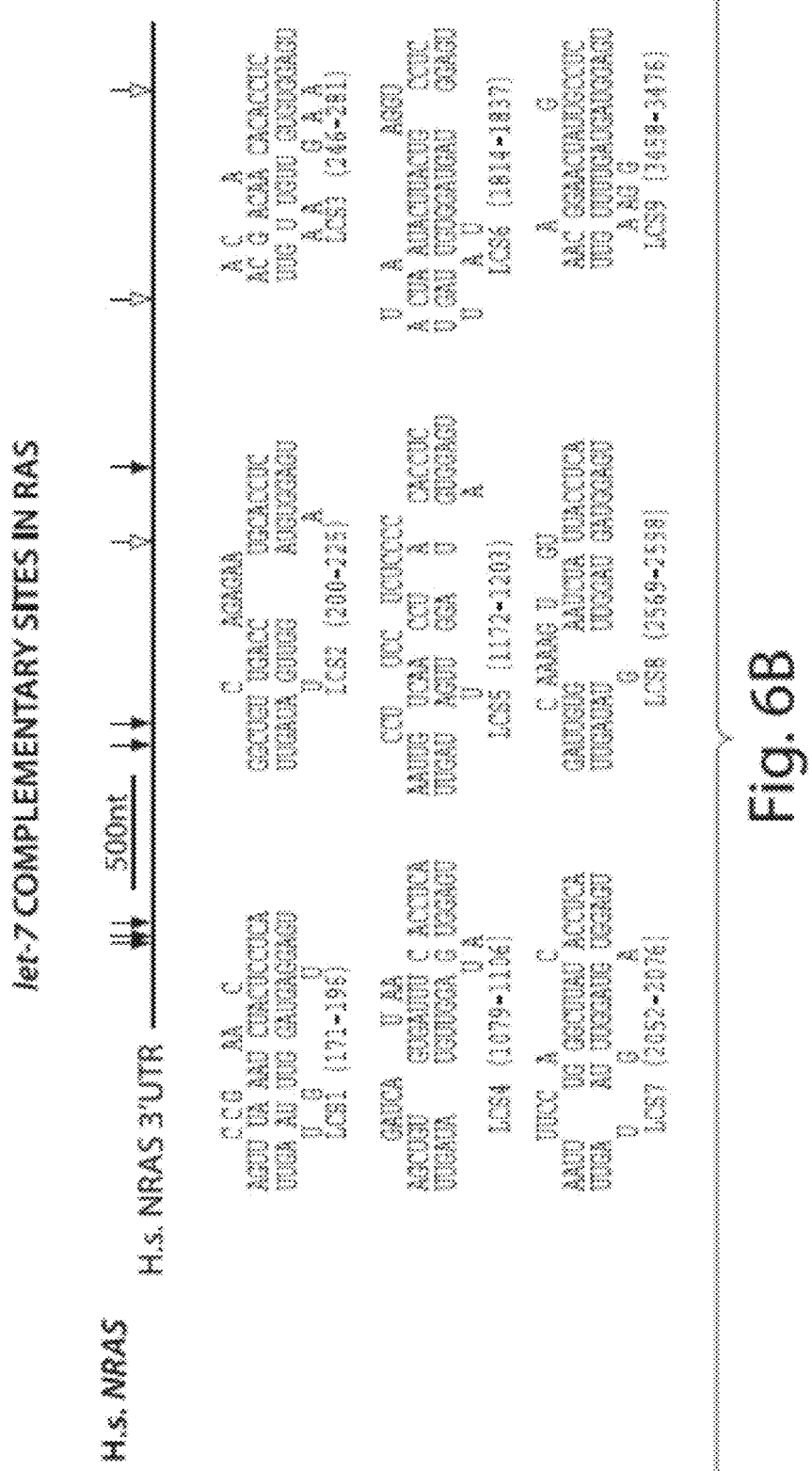

The Human NRAS 3' UTR comprises 9 LCSs named LCS1-LCS9, respectively (see FIG. 6B). For the following sequences, thymine (T) may be substituted for uracil (U). LCS1 comprises the sequence AGUUCUCAGAAUAAC-UACCUCCUCA (SEQ ID NO: 1). LCS2 comprises the sequence GGCUGUCUGACCAGAGAAUGCACCUC (SEQ ID NO: 2). LCS3 comprises the sequence ACAGCA-CAAACACACCUC (SEQ ID NO: 3). LCS4 comprises the sequence AGCUGUGAUCAGUGAUUUUCAAACCYCA (SEQ ID NO: 4). LCS5 comprises the sequence AAUUGC-CUUCAAUCCCUUCUCACCCCACCUC (SEQ ID NO: 5). LCS6 comprises the sequence AUCUAAAUACU-UACUGAGGUCCUC (SEQ ID NO: 6). LCS7 comprises the sequence AAUUUUCCUGAGGCUUAUCACCUCA (SEQ ID NO: 7). LCS8 comprises the sequence GAUUGCUGAAAAGAAUUCUAGUUUACCUCA (SEQ ID NO: 8). LCS9 comprises the sequence AACAGGAAC-UAUUGGCCUC (SEQ ID NO: 9).

Figure 6C:
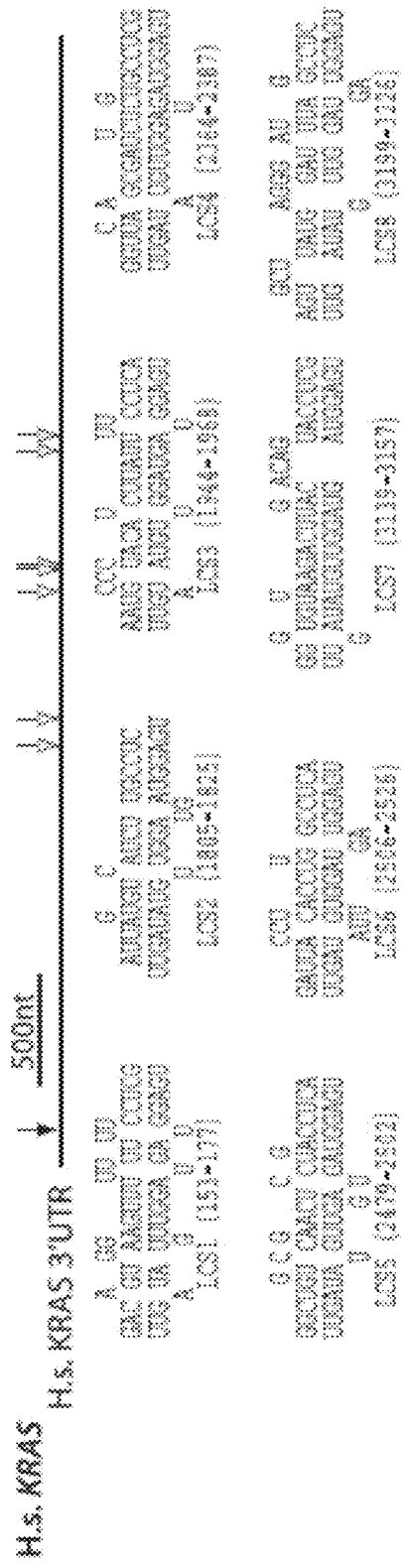

The Human KRAS 3' UTR comprises 8 LCSs named LCS1-LCS8, respectively (see FIG. 6C). For the following sequences, thymine (T) may be substituted for uracil (U). LCS1 comprises the sequence GACAGUGGAAGU-UUUUUUUUCCUCG (SEQ ID NO: 10). LCS2 comprises the sequence AUUAGUGUCAUCUUGCCUC (SEQ ID NO: 11). LCS3 comprises the sequence AAUGCCCUACAUCU-UAUUUCCUCA (SEQ ID NO: 12). LCS4 comprises the sequence GGUUCAAGCGAUUCUCGUGCCUCG (SEQ ID NO: 13). LCS5 comprises the sequence GGCUGGUC-CGAACUCCUGACCUCA (SEQ ID NO: 14). LCS6 comprises the sequence GAUUCACCCACCUUGGCCUCA (SEQ ID NO: 15). LCS7 comprises the sequence GGGUG-UUAAGACUUGACACAGUACCUCG (SEQ ID NO: 16). LCS8 comprises the sequence AGUGCUUAUGAGGG-GAUAUUAGGCCUC (SEQ ID NO: 17).

Figure 6D:
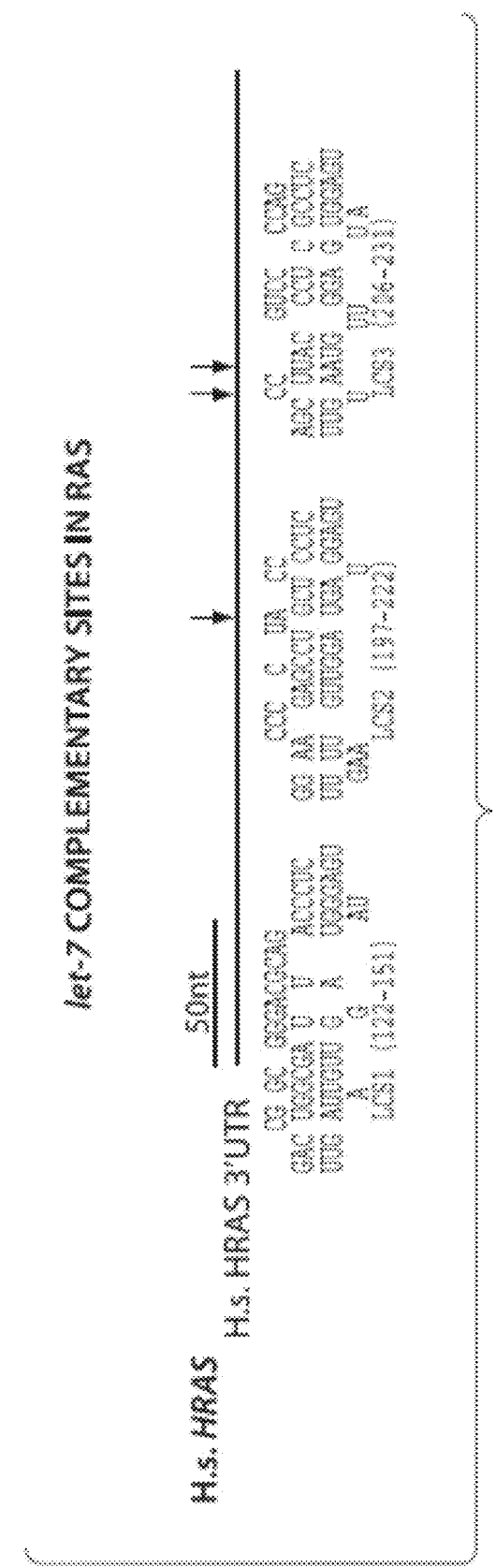

The Human HRAS 3' UTR comprises 3 LCSs named LCS1-LCS3, respectively (see FIG. 6D). For the following sequences, thymine (T) may be substituted for uracil (U). LCS1 comprises the sequence GACCGUGGGCCGAG-GUGACUGCAGACCCUC (SEQ ID NO: 18). LCS2 comprises the sequence GGAACCCCAGCCCUUAGCUC-CCCUC (SEQ ID NO: 19). LCS3 comprises the sequence AGCCCUUAGCUCCCCUCCCAGGCCUC (SEQ ID NO: 20).

The LCS6 SNP

The present invention encompasses a SNP within the 3'UTR of KRAS. Specifically, this SNP is the result of a substitution of a G for a U at position 4 of SEQ ID NO: 21 of LCS6. This LCS6 SNP comprises the sequence GAUGCAC-CCACCUUGGCCUCA (SNP bolded for emphasis) (SEQ ID NO: 21).

let-60, the *C. elegans* homolog of human RAS, is a direct target of let-7. It has multiple putative let-7 complementary sites (LCSs) in its 3' UTR. Human RAS is a well known oncogene that often plays a role in cancer. Knock down of let-60 by RNA interference (RNAi) in let-7(n2853) loss-of-function mutants partially suppresses the lethal, bursting phenotype of let-7(n2853) (FIG. 7). Furthermore, a lacZ reporter containing the let-60 3' UTR was down regulated in the presence of let-7.

Figure 5:
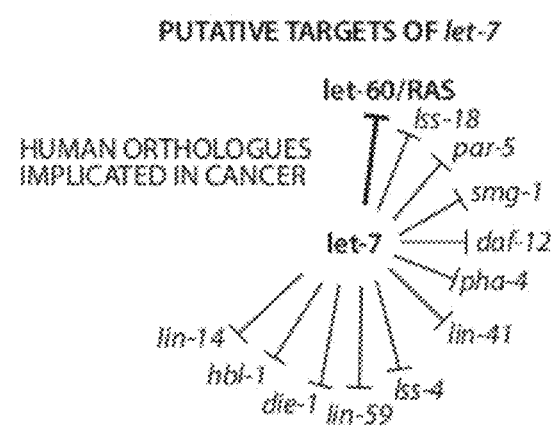
FIG. 5 is a schematic drawing showing putative targets of the let-7 miRNA.
Figure 9:
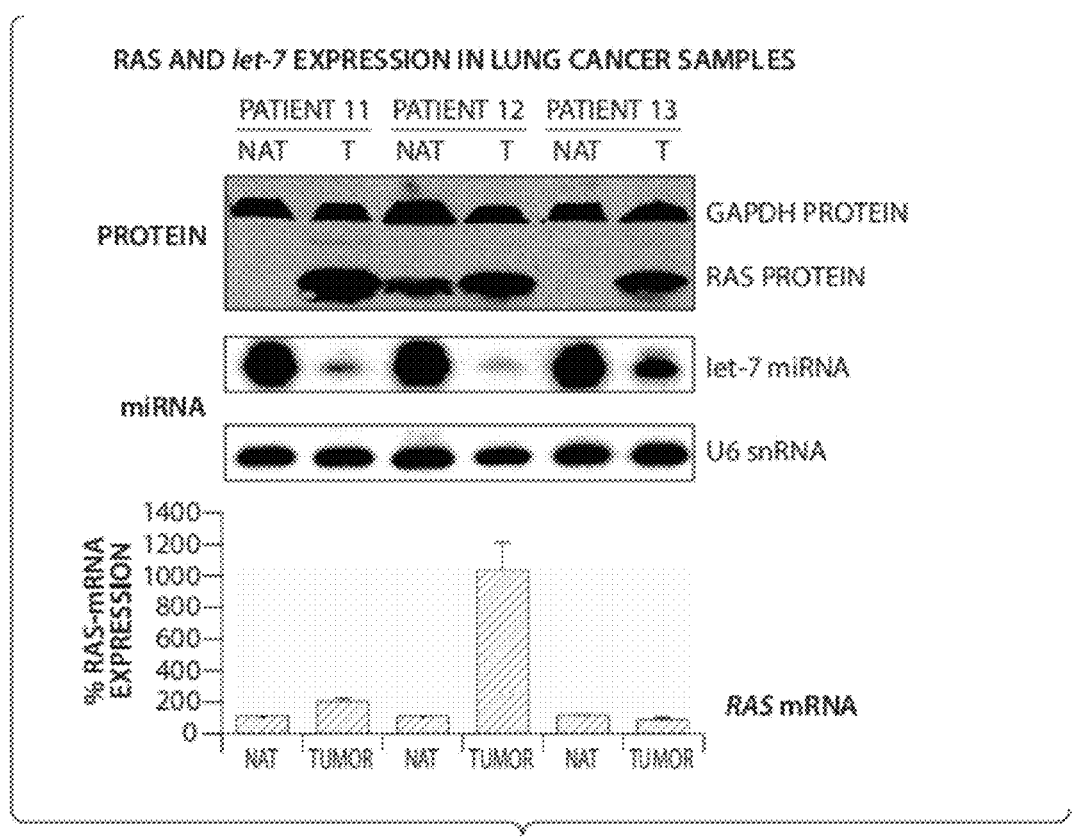
FIG. 9 provides DNA and protein expression data from three lung cancer patients showing that decreases in let-7 miRNA expression lead to increases in RAS protein expression in tumor cells.
Figures 1, 10:
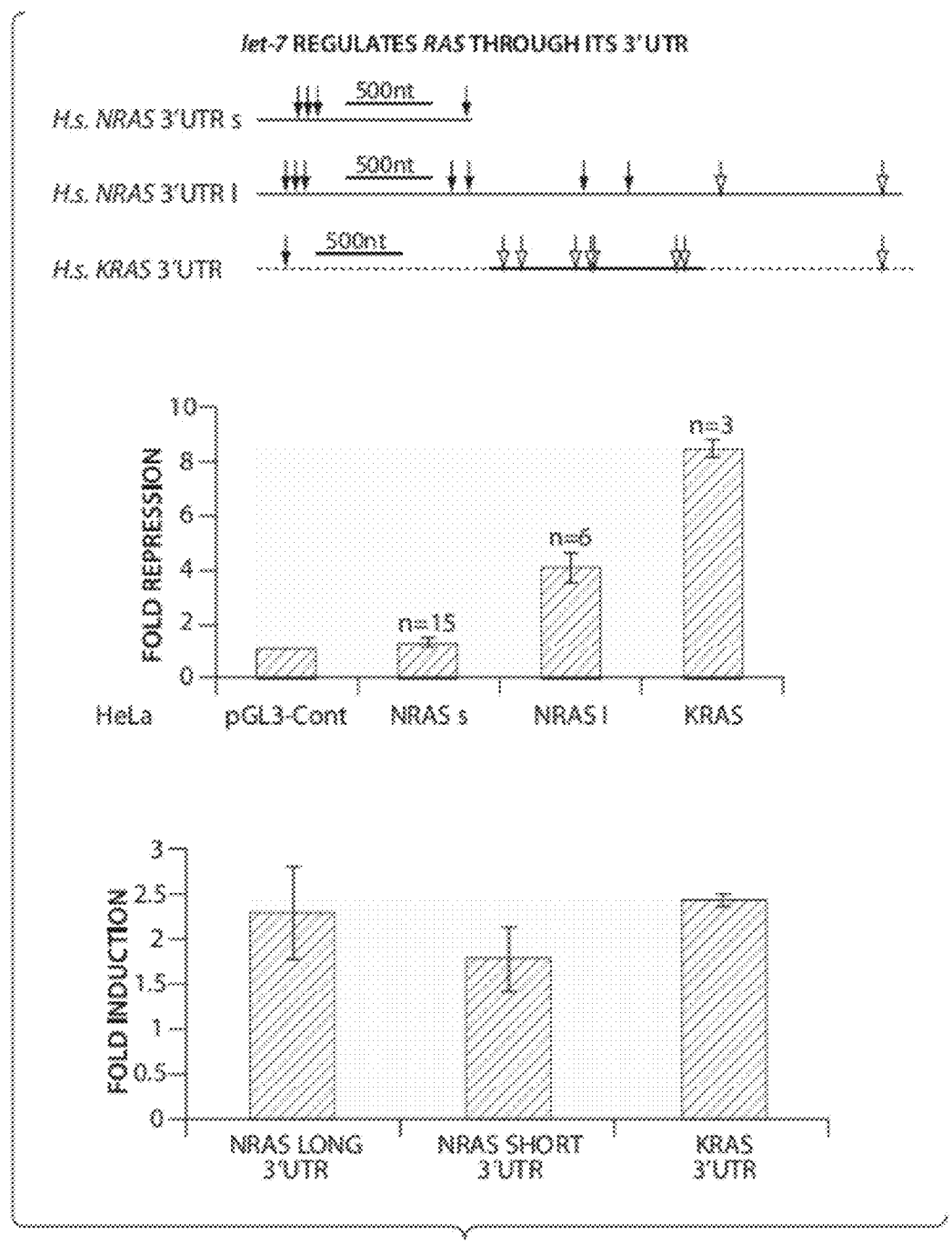
FIG. 10 demonstrates that let-7 regulates RAS through its 3'UTR. Upper left panel shows schematic representation of let-7 complementary sites within the 3'UTRs of *H. sapiens* NRAS and KRAS. Middle and bottom left panels show the fold repression of RAS by let-7 miRNA and the fold induction of RAS by silencing let-7 miRNA by RNAi, both in HeLa cells. The top right panels show fluorescent images of RAS protein expression following treatment of HepG2 cells with the let-7 miRNA or a negative control and the quantification of these images, respectively. Bottom right panels show fluorescent images of RAS protein expression following treatment of HeLa cells with an inhibitor of the let-7 miRNA or a negative control inhibitor and the quantification of these images, respectively.
Figures 2, 10:
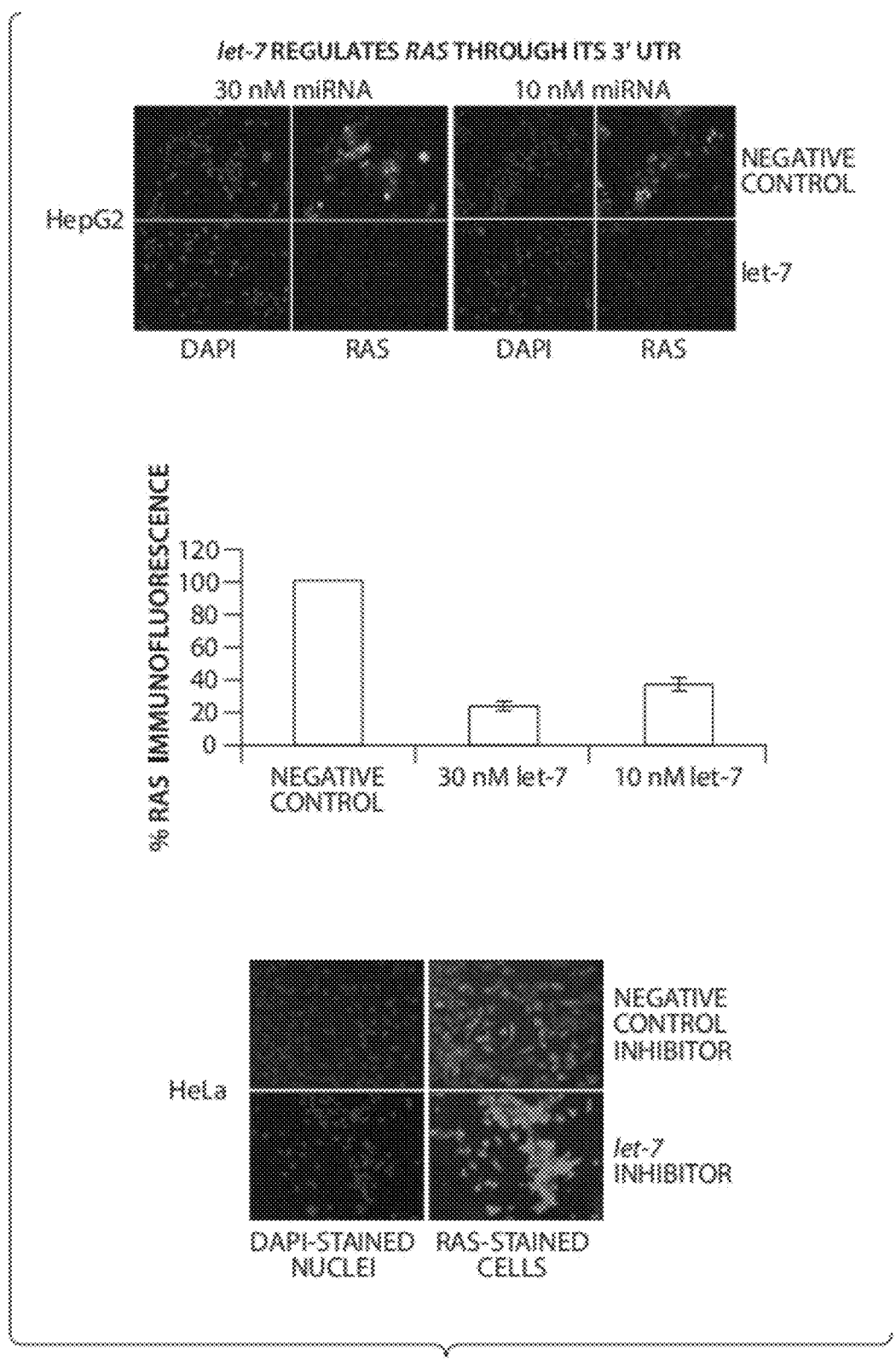
Figures 3, 10:
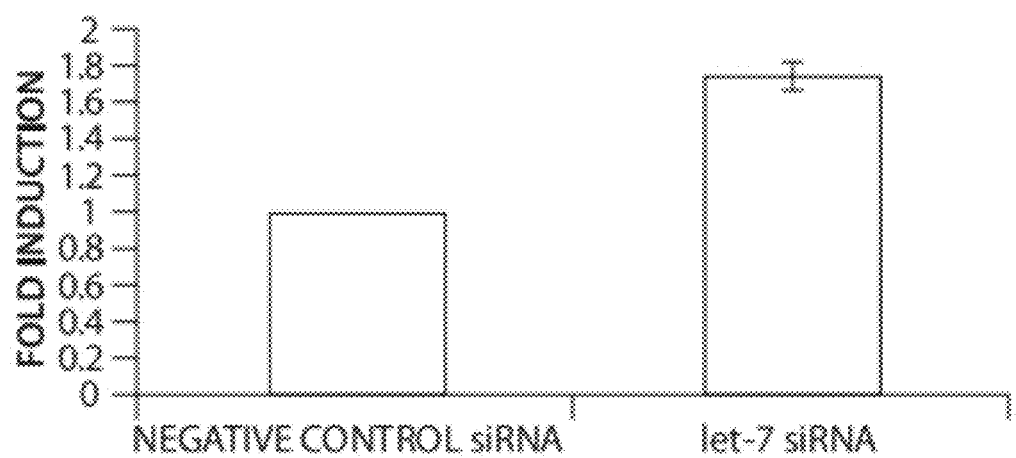
Figure 12:
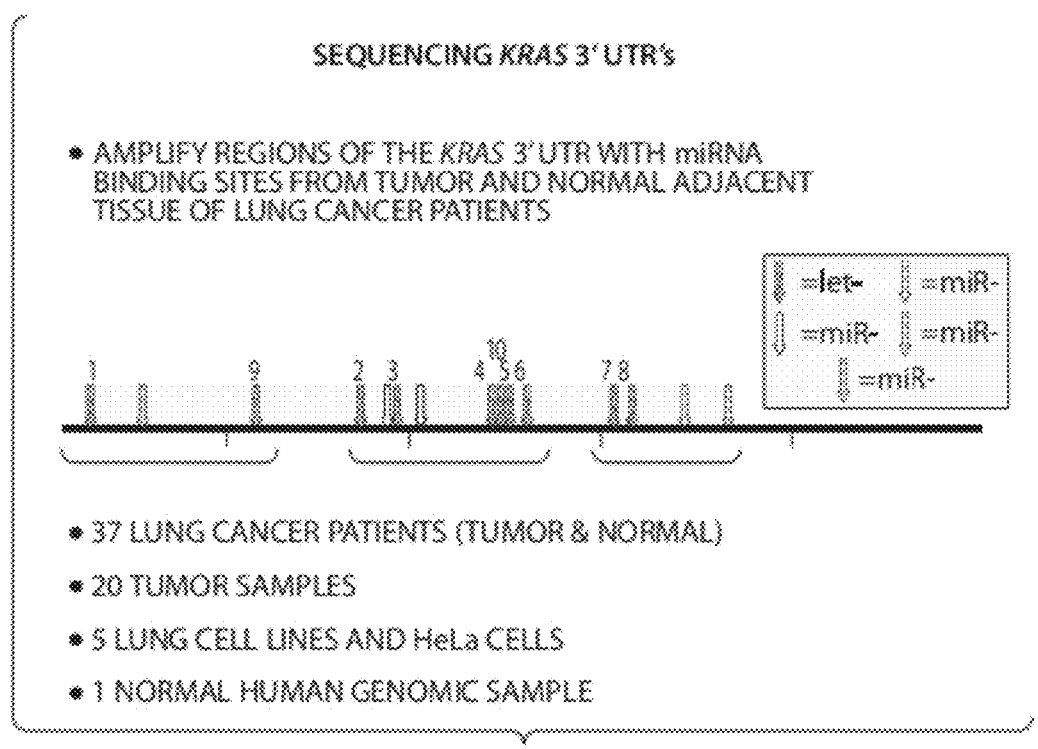
FIG. 12 is a schematic representation and explanation of strategy for sequencing 3' UTRs of KRAS.
Figure 14:
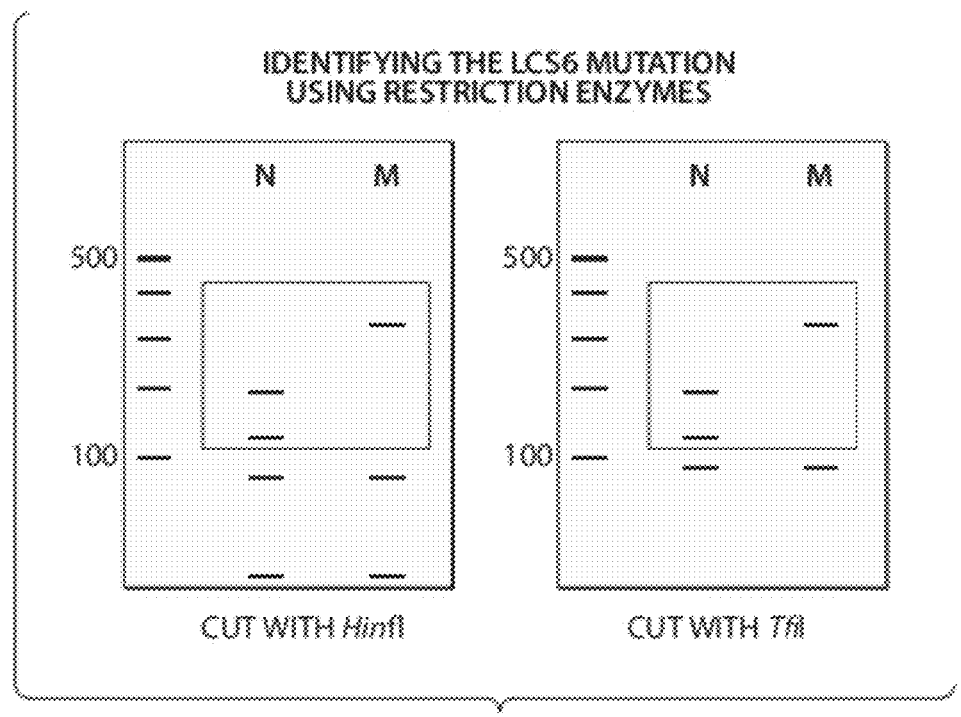
FIG. 14 is a schematic representation of method for rapidly identifying LCS6 mutation in a DNA sample using restriction enzyme analysis.
Figure 15:
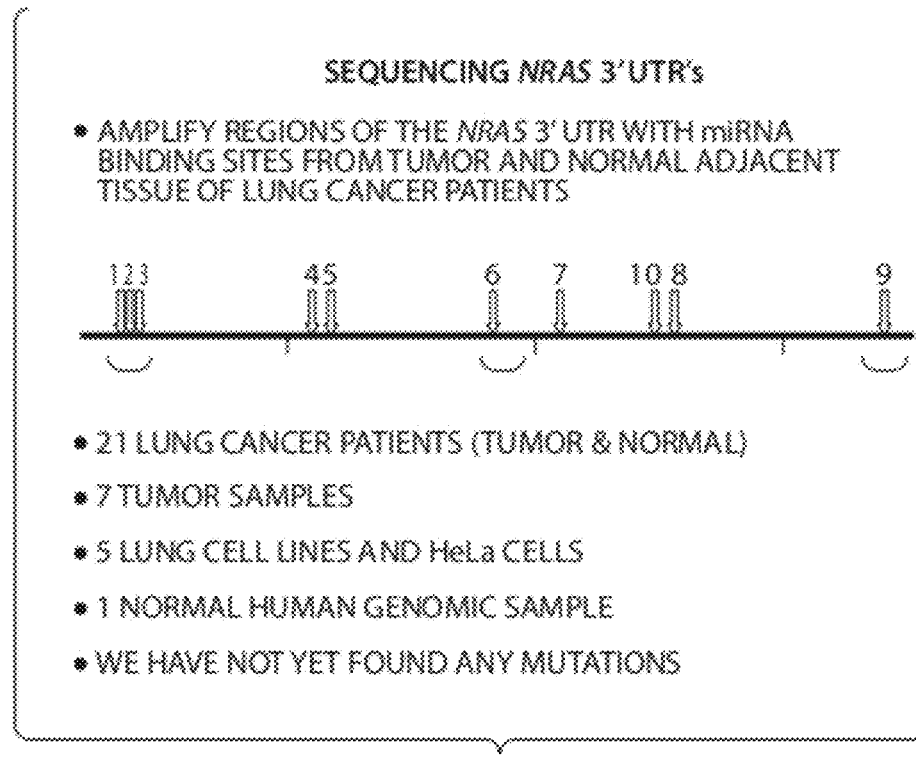
FIG. 15 is a schematic representation of miRNA complementary sites within 3'UTRs of NRAS and methods for sequencing these regions.
Figure 16:
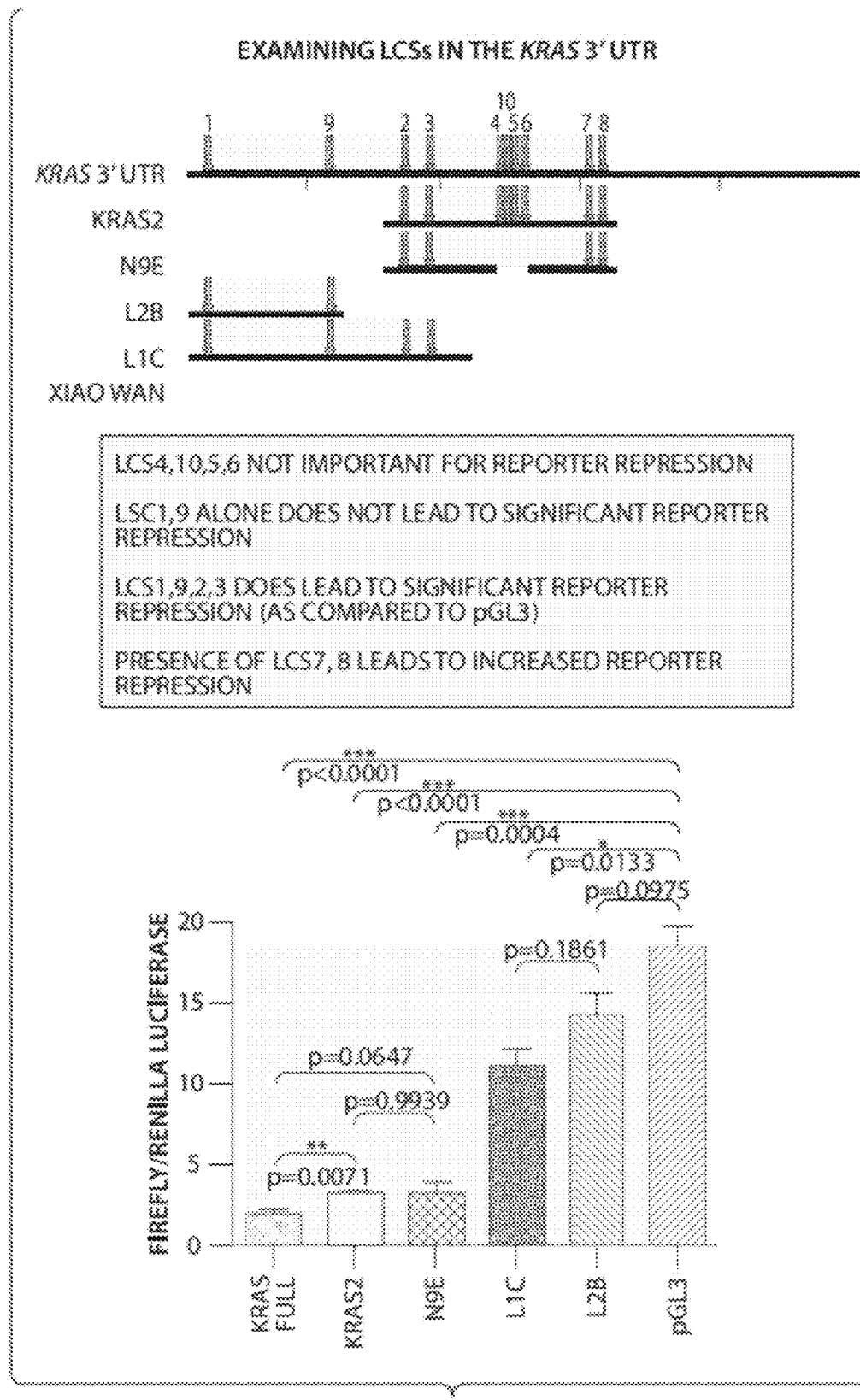
FIG. 16 shows an analysis of LCSs in KRAS 3'UTR with respect to ability of mutations in these regions to decrease reporter gene expression.
Figures 1, 17:
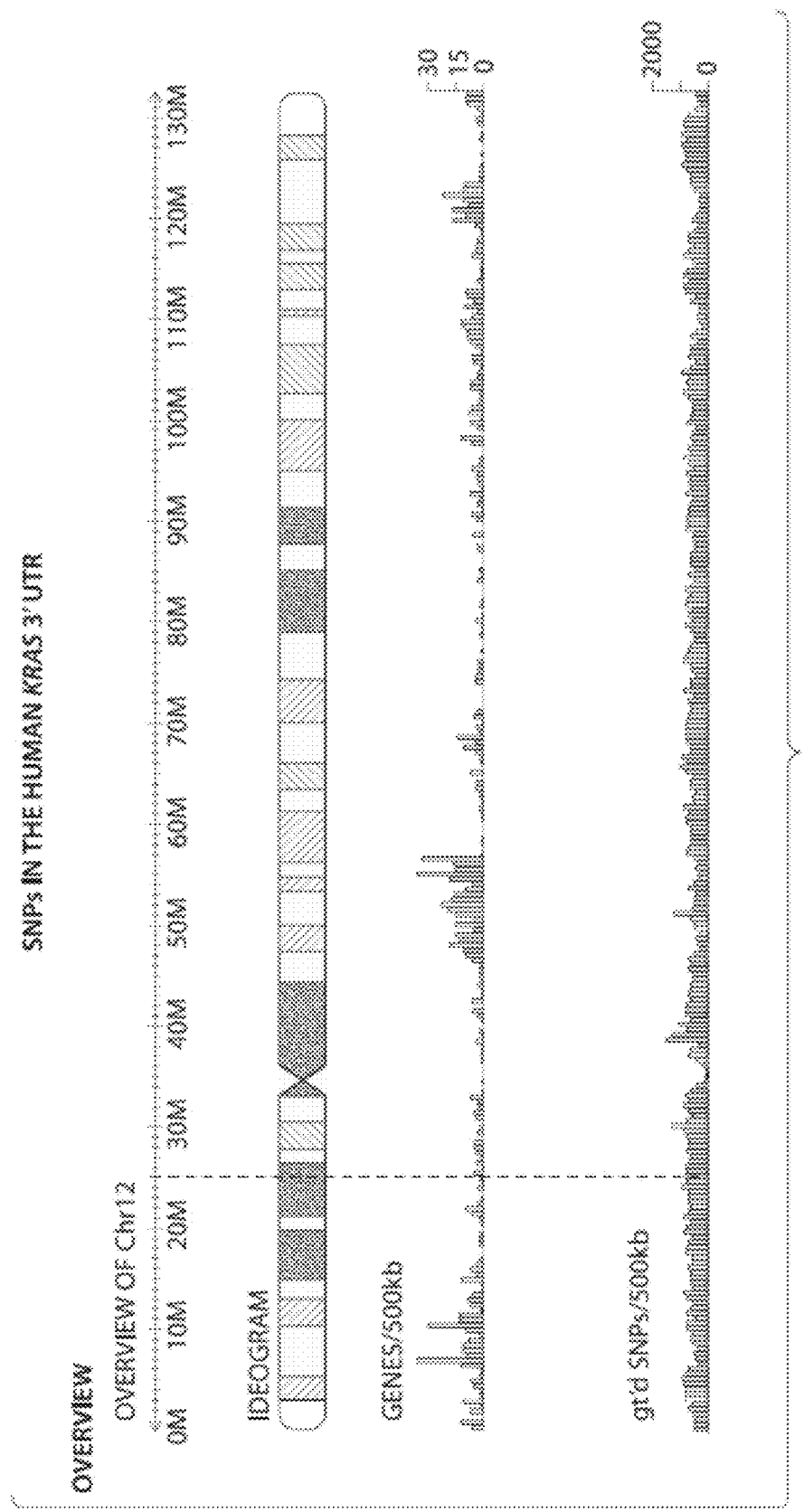
FIG. 17 is a screen shot of Ensembl report (www.ensembl.org) of SNP in the human KRAS 3'UTR.
Figures 2, 17:
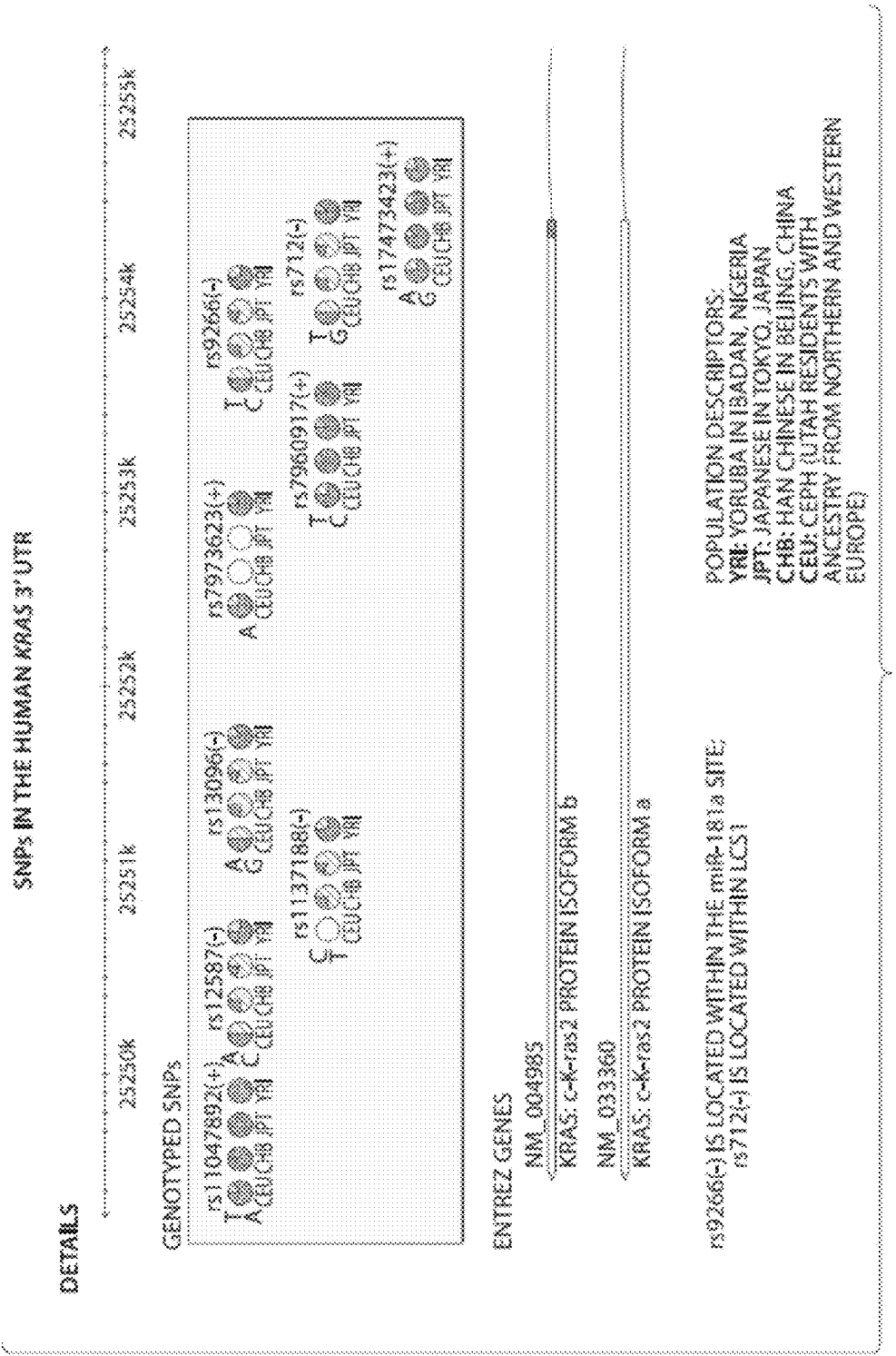
Figures 1, 18:
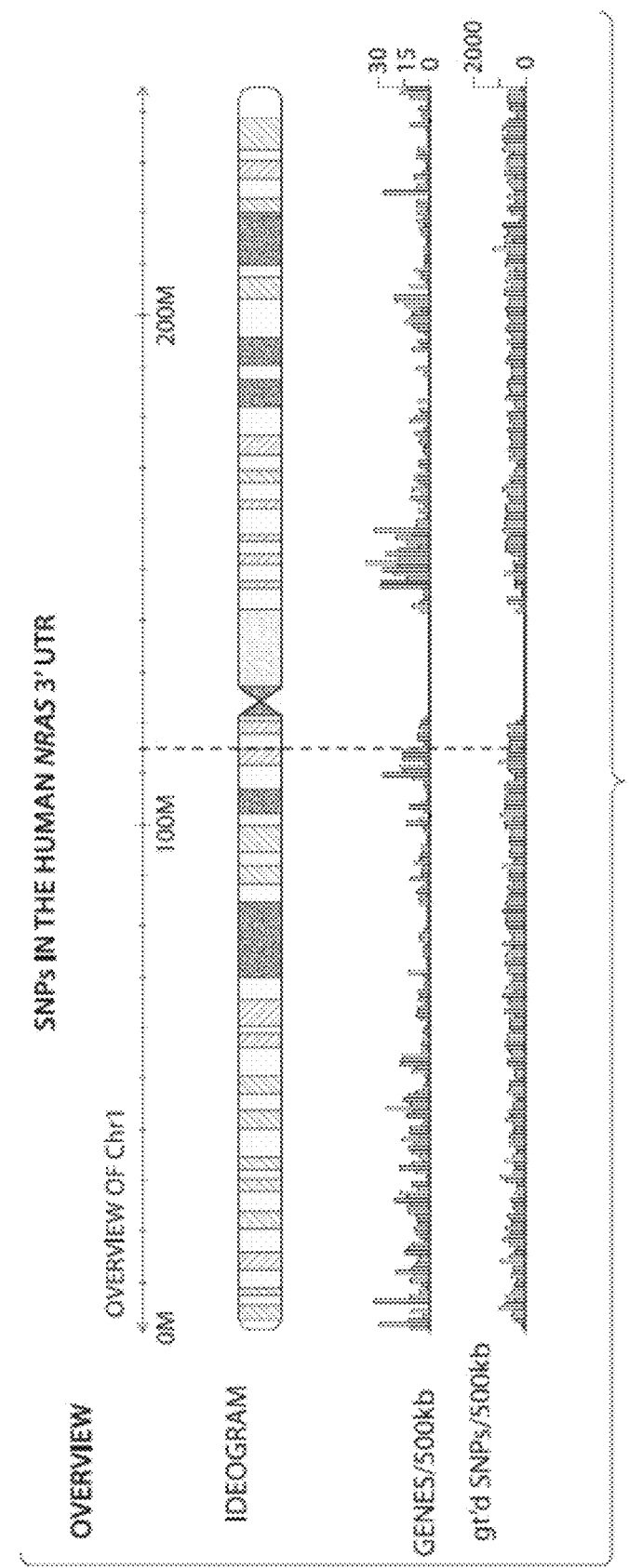
FIG. 18 is a screen shot of Ensembl report (www.ensembl.org) of SNP in the human NRAS 3'UTR.
Figures 2, 18:
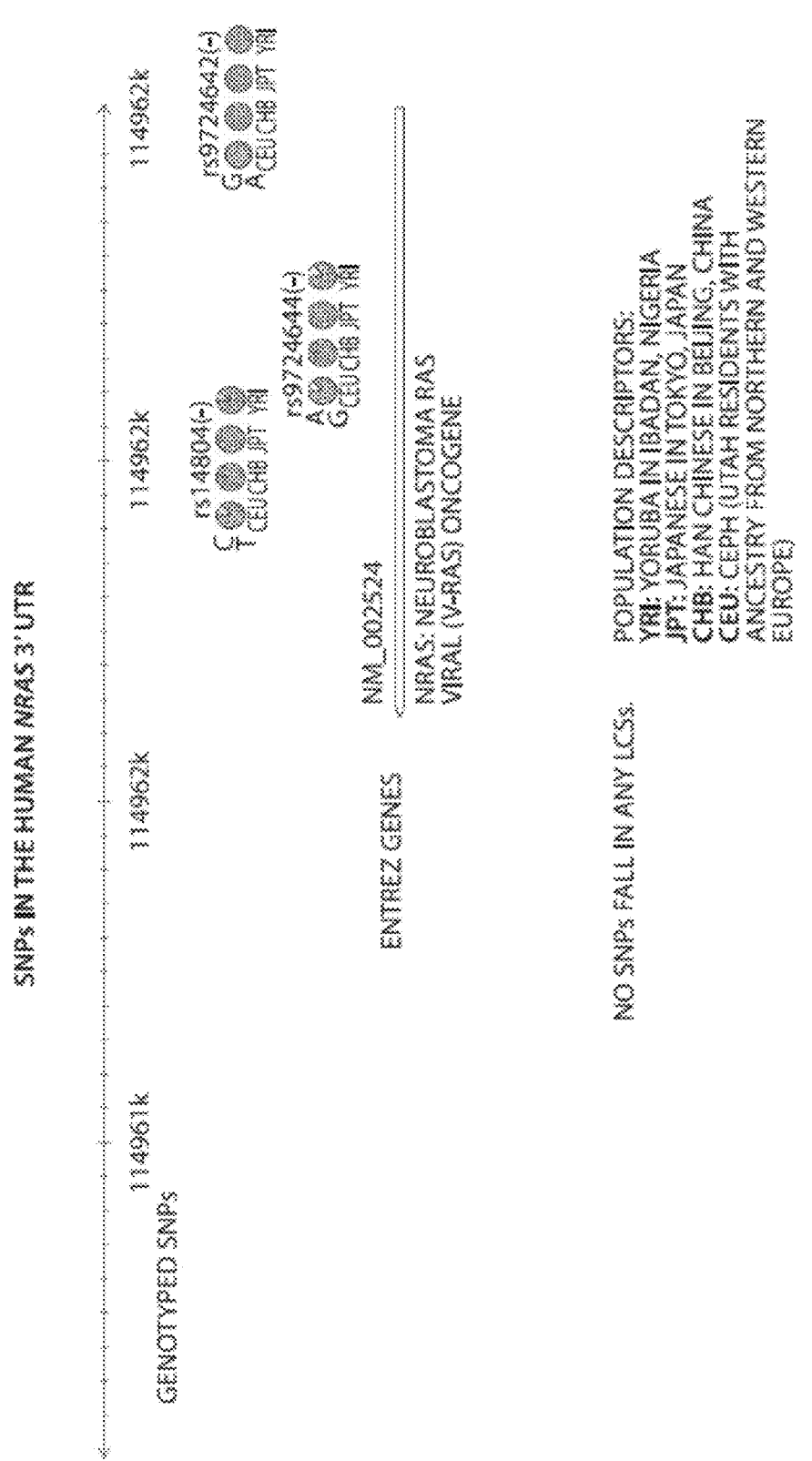

Human RAS is also a target of let-7 (FIG. 5). There are 3 human RAS genes: HRAS, KRAS, and NRAS. Each of these genes has multiple LCSs in their 3' UTRs (FIG. 7). Based on RAS levels in the absence or presence of let-7 (FIG. 10), luciferase reporters with the 3' UTRs of NRAS or KRAS (FIG. 22), and the inverse relationship between RAS and let-7 levels in lung cancer patients (FIG. 9), it was determined that let-7 represses RAS in a 3' UTR-dependent manner in human cells. Human let-7 is at low levels in various human cancers, suggesting that let-7 is a tumor suppressor, and lung cancer patients with low levels of let-7 have decreased survival rates, supporting the hypothesis that let-7 is important in lung cancer.

The KRAS and NRAS 3' UTRs have been sequenced from lung samples of lung cancer patients, normal lung samples, and human cell lines (FIGS. 6, 10, 12, and 15). In the KRAS 3' UTR, several LCSs containing mutations were found (FIGS. 14, 16, 20, 23, and 25). None of these mutations appeared to be associated with lung cancer. In contrast, a single nucleotide polymorphism (SNP) at the fourth base pair of LCS6, the LCS6 SNP was found in 20% of patient samples. The LCS6 SNP was associated with the risk of developing squamous cancers versus adenocarcinomas of the lung, with younger patients with lung cancer in our population, with patients that had additional cancers, and with patients with positive family histories of cancer.

To further validate the importance of this SNP in lung cancer predisposition the baseline prevalence in the 25 different human populations was first determined. The prevalence was highest in Caucasian populations, at 7.4%. In Caucasian lung cancer patients the prevalence was 24%, which is significantly higher. The association of this SNP with smoking-induced lung cancer was further validated in a case control study of smokers who did or did not develop lung cancer. A significant association of the SNP with non-small cell lung cancer development in patients matched for age, sex, race and smoking status was found. These results support the hypothesis that the presence of the LCS6 SNP is a genetic marker for an increased risk of lung cancer development.

Figure 25:
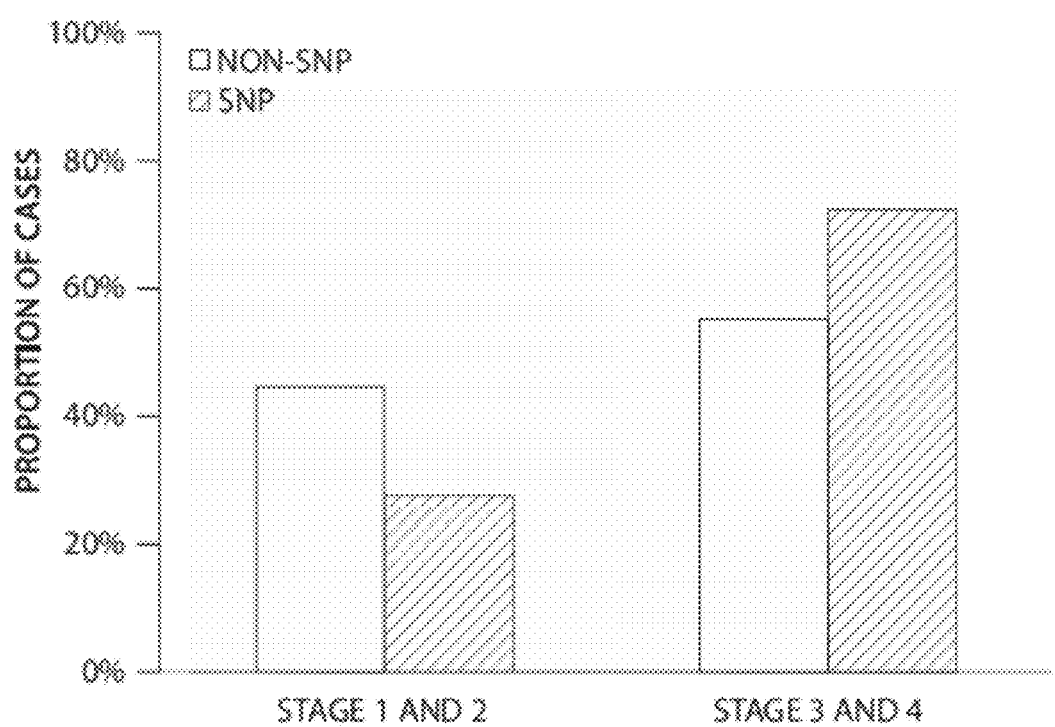
FIG. 25 shows the prevalence of the LCS6 SNP in ovarian cancers of higher stage rating. The graph illustrates that a greater proportion of ovarian cancer cases studied, in which the LCS6 SNP was present, presented at elevated stages resulting in worse prognoses for the individuals carrying the LCS6 SNP than for those who did not carry the LCS6 SNP.

The prevalence of the LCS6 SNP was further examined in several other cancers, including head and neck cancers, breast cancer, ovarian cancer, uterine cancer and pancreatic cancer. It was discovered that the LCS6 SNP is at a significantly higher prevalence than expected in these cancers. Moreover, the LCS6 SNP has been demonstrated to be associated with a specific subtype of each of these cancers (Table 1). Specifically, the LCS6 SNP was shown to be associated with the subtypes associated with the worst prognosis in each of these cancer types. With respect to ovarian cancer, for instance, the presence of the LCS6 SNP is also coincident with the presentation of more advanced stages of cancer (FIG. 25). Accordingly, the LCS6 SNP predicts whether the cancer is aggressive or resistant to current therapy, which are the most critical to prevent. This predictive ability demonstrates that the presence of the LCS6 SNP is a biomarker of cancer outcome.

TABLE 1

Prevalence of KRAS SNP in Cancer Types
Table 1. Prevalence studies based on the expected frequency of the SNP of 14%. Significance is based on a Chi-squared analysis. Chi-squared and OR numbers are based on the prevalence expected in Caucasian patients of 14%, and for some of these cancers up to ½ of cancer patients were AA, thus, these are underestimations.

| Cancer Type | Frequency of SNP | Significance |
|---|---|---|
| Case control Studies | | |
| Lung cancer (Non-small cell subtype) | 18.1-20.3% (from 2 independent case controls, 400 and 4000 pts.) | OR = 1.4-2.3, $p < 0.01$ |
| Pancreatic cancer (Exocrine pancreas) | 18.8% (800 patients, ongoing) | OR = 1.2 |
| Prevalence studies | | |
| Endometrial Cancer (High Risk subtypes) | 48% (10/21) | $p = .0004$ odds ratio = 5.57 |
| Ovarian Cancer (all subtypes) | 51% (22/43) | $p < 0.00000000001$ odds ratio = 8.45 |
| Head and Neck Cancer (Oropharynx subtype) | 33% (8/24) | $p = 0.011$ odds ratio = 3.07 |
| Breast Cancer (Her-2 + subtype) | 25% (7/22) | $p = 0.017$ odds ratio = 2.1 |
| Colon Cancer | 18.3% (249/1364) | $p < 0.001$ odds ratio = 1.4 |
| Melanoma | 28.6% (2/7) | $p < 0.01$ odds ratio = 2.0 |

Figure 22A:
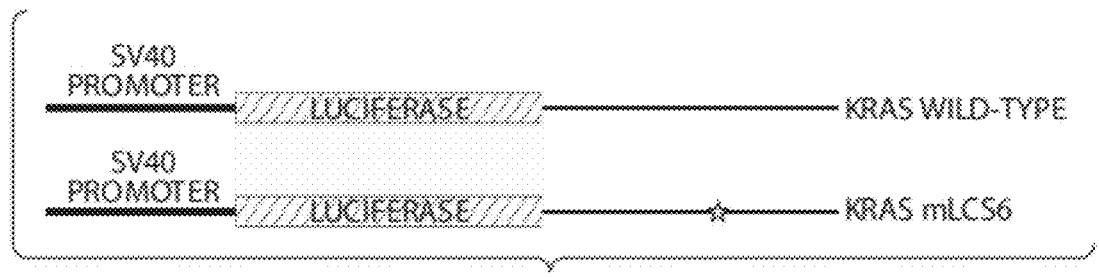
FIGS. 22A-C demonstrates the effects of let-7 miRNA silencing on KRAS wild type LCS6 and the KRAS LCS6 SNP. (A) Luciferase reporter constructs containing the KRAS 3'UTR. Striped boxes signify the 3'UTR used in the reporter constructs. A star represents the variant allele in LCS6. (B) Representative graph of luciferase activity of KRAS wild-type and KRAS mLCS6 (P<0.001) in A549 cells. Triplicate repeats were conducted showing similar results. (C) Representative graph of luciferase activity of KRAS wild-type and KRAS mLCS6 that were co-transfected with prelet-7b (Ambion) (P=0.001) in A549 cells. Luciferase expression values were normalized to the average luciferase expression value of samples treated with pre-miR Negative Control #1 (Ambion). Triplicate repeats were conducted showing similar results.
Figure 22B:
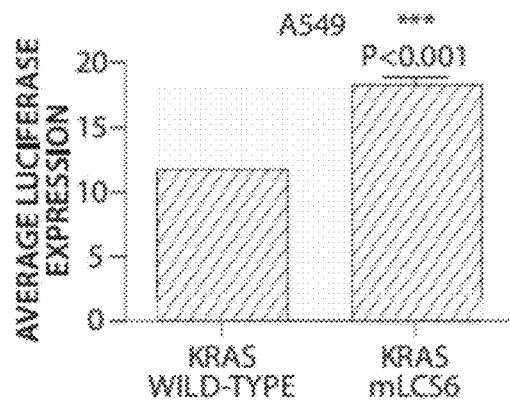
Figure 22C:
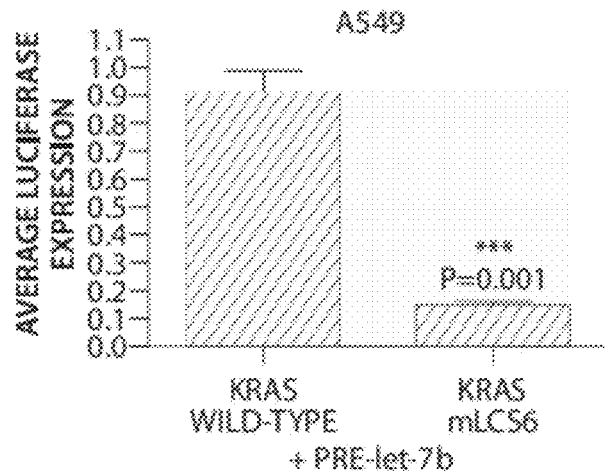
Figure 23A:
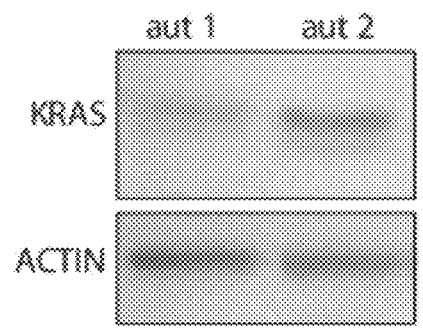
FIG. 23A-C demonstrates overexpression of KRAS in a human cancer patient carrying the LCS6 SNP. (A) KRAS protein levels were measured in two autopsy samples, one without the variant allele (Aut1) and one with the variant allele (Aut2). Actin shows similar loading (below). Levels were analyzed using Quantity One software from BioRad. (B) let-7a, b, d and g levels in eight tumors with and eight without the variant allele. Samples were normalized to two non-cancerous patients, whose let-7 levels were similar. Error bars represent variation between PCR reactions for each sample. (C) KRAS levels in a patient without and one with the variant allele higher KRAS in the tumor harboring the variant allele. Actin is shown below.
Figure 23B:
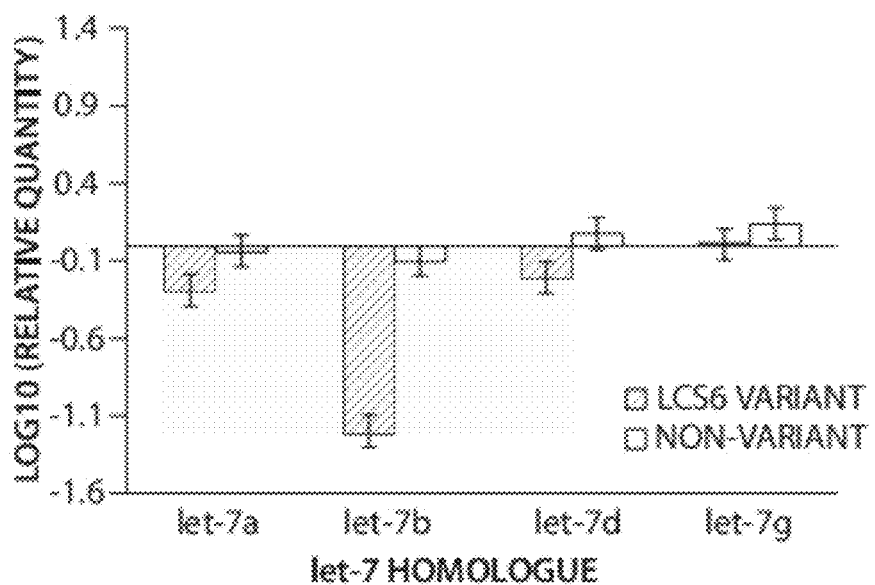
Figure 23C:
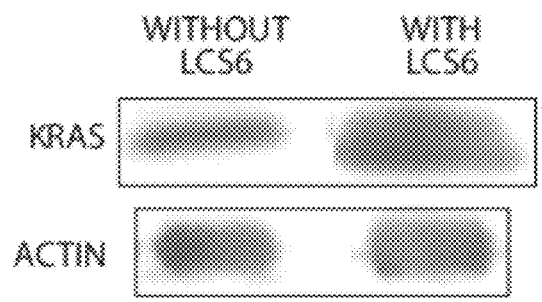

The LCS6 SNP was examined to determine how the presence of the SNP altered the binding efficacy of let-7 family miRNAs to KRAS. The LCS6 SNP was engineered in a luciferase reporter construct containing all LCSs (FIG. 22). The LCS6 SNP causes an increase in luciferase expression as compared to the non-SNP reporter in lung cancer cells.

In two case-controlled association studies, the presence of the variant allele predicts for an increased risk of non-small cell lung cancer (NSCLC) (OR=1.36-2.3, 95% CI=1.07-1.73, p=0.01, 95% CI=1.1-4.6, p=0.02) in patients with a <40 to 41 pack-year smoking history. One difference between the subjects of the case-control designs and the patient cohort at Yale University is that the case-control designs were primary lung cancer studies, and thus people with prior cancers were excluded from both. In contrast, in the retrospective patient cohort, 64% of the allele-carriers had additional cancers and 89% of these cancers were diagnosed before their lung cancer. This difference may actually lead to an under-estimation of the lung cancer risk for smokers carrying the variant allele. As such, these studies may underestimate the predictive power of the LCS6 SNP comprised by the invention.

While not limited by theory, the present invention includes and is based in part on the understanding that alteration of let-7 binding, brought about by the presence or absence of one or more SNP(s), impacts cellular levels of let-7. Increased let-7 binding could lead to sequestration of let-7 and a decrease in cellular let-7 levels. As let-7 is known to regulate cell proliferation genes, this could lead to excess cellular proliferation and oncogenesis. Equally as plausible, however, is the possibility that there exists a cellular feed-back system that would detect let-7 as too low due to its increased KRAS binding, leading to elevated cellular let-7 levels. As let-7 has been shown to regulate genes important in the DNA damage response pathway, a state of high let-7 could also lead to oncogenesis by leaving the cell open to excess DNA damage.

This LCS6 SNP is a marker for increased genetic susceptibility to smoking induced lung cancer and other cancers. Methods of the invention demonstrating means for identifying this SNP and similar SNPs are used to enhance screening programs to enrich for people at the highest risk of developing lung cancer, testing families with histories of lung cancer to determine individual risk, setting up smoking cessation programs and screening participants, and testing patients with smoking-induced cancers to determine the risk of developing additional, or secondary, cancers. This SNP variant, as well as all SNPs encompassed by the invention, are used to predict cancer outcome, e.g. prognosis, and to identify patients for whom therapies designed to target particular SNPs should be applied.

The LCS6 SNP comprises the first identified 3' UTR SNP affecting miRNA binding that is genetically linked to cancer. The methods of the invention demonstrate particular utility as an incentive for individuals who smoke to accurately access smoking-induced risk for developing lung cancer and/or additional cancers. The LCS6 SNP can also be used to assess an increased risk of developing ovarian, breast, colon, head and neck, pancreatic and kidney cancers.

Moreover, the presence of the LCS6 SNP indicates a greater risk for developing radon-associated non-small cell lung cancer, as well as other radon-associated cancers. Radon is a colorless, naturally occurring, radioactive noble gas that is formed from the decay of radium. The radiation decay products ionize genetic material, causing mutations that sometimes turn cancerous. It is one of the heaviest substances that are gases under normal conditions and is considered to be a health hazard. Radon is a significant contaminant that affects indoor air quality worldwide. Radon gas from natural sources can accumulate in buildings and reportedly causes 21,000 lung cancer deaths per year in the United States alone. Radon is the second most frequent cause of lung cancer, after cigarette smoking, and radon-induced lung cancer is thought to be the 6th leading cause of cancer death overall.

Methods of the invention were used to determine the prevalence of the LCS6 SNP among cancer patients whose occupation was mining. Among minors who developed lung cancer, data gathered using the methods of the invention show that the prevalence of the LCS6 SNP was higher than expected in this population (23% in minors with lung cancer patients versus 14% in control individuals who represent the general, non-cancerous population). The average radon exposure among the minors studied was 1362 work level months for the non-LCS6 SNP subset versus 1073 work level months for the LCS6 SNP carrying subset. Work level months is a measurement that reflects the number of hours of exposure to radon over an equal number of months.

These data show that LCS6 SNP carrying individuals are at a greater risk of developing radon associated lung cancer (as well as other radon-associated cancers) than individuals who do not carry the LCS6 SNP, because the LCS6 SNP carrying population are over-represented as cancer patients in this study despite having overall less exposure to radon. In other words, individuals who carry the LCS6 SNP appear to develop radon-associated cancers following a lower level or threshold of radon exposure. In a preferred embodiment, methods of the invention are used to determine an individual's risk for developing radon-associated cancer prior to, during, or following exposure to radon.

Isolated Nucleic Acid Molecules

The present invention provides isolated nucleic acid molecules that contain one or more SNPs. Exemplary isolated nucleic acid molecules containing one or more SNPs include, but are not limited to, the nucleic acid molecules of SEQ ID NOs: 21, 26, and 27. Isolated nucleic acid molecules containing one or more SNPs disclosed herein may be interchangeably referred to throughout the present text as "SNP-containing nucleic acid molecules". Isolated nucleic acid molecules may optionally encode a full-length variant protein or fragment thereof. The isolated nucleic acid molecules of the present invention also include probes and primers (which are described in greater detail below in the section entitled "SNP Detection Reagents"), which may be used for assaying the disclosed SNPs, and isolated full-length genes, transcripts, cDNA molecules, and fragments thereof, which may be used for such purposes as expressing an encoded protein.

As used herein, an "isolated nucleic acid molecule" generally is one that contains a SNP of the present invention or one that hybridizes to such molecule such as a nucleic acid with a complementary sequence, and is separated from most other nucleic acids present in the natural source of the nucleic acid molecule. Moreover, an "isolated" nucleic acid molecule, such as a cDNA molecule containing a SNP of the present invention, can be substantially free of other cellular material, or culture medium when produced by recombinant techniques, or chemical precursors or other chemicals when chemically synthesized. A nucleic acid molecule can be fused to other coding or regulatory sequences and still be considered "isolated". Nucleic acid molecules present in non-human transgenic animals, which do not naturally occur in the animal, are also considered "isolated". For example, recombinant DNA molecules contained in a vector are considered "isolated". Further examples of "isolated" DNA molecules include recombinant DNA molecules maintained in heterologous host cells, and purified (partially or substantially) DNA molecules in solution. Isolated RNA molecules include in vivo or in vitro RNA transcripts of the isolated SNP-containing DNA molecules of the present invention. Isolated nucleic acid molecules according to the present invention further include such molecules produced synthetically.

Generally, an isolated SNP-containing nucleic acid molecule comprises one or more SNP positions disclosed by the present invention with flanking nucleotide sequences on either side of the SNP positions. A flanking sequence can include nucleotide residues that are naturally associated with the SNP site and/or heterologous nucleotide sequences. Preferably the flanking sequence is up to about 500, 300, 100, 60, 50, 30, 25, 20, 15, 10, 8, or 4 nucleotides (or any other length in-between) on either side of a SNP position, or as long as the full-length gene, entire coding, or non-coding sequence (or any portion thereof such as an exon, intron, or a 5' or 3' untranslated region (UTR)), especially if the SNP-containing nucleic acid molecule is to be used to produce a protein or protein fragment.

For full-length genes and entire protein-coding sequences, a SNP flanking sequence can be, for example, up to about 5 KB, 4 KB, 3 KB, 2 KB, 1 KB on either side of the SNP. Furthermore, in such instances, the isolated nucleic acid molecule comprises exonic sequences (including protein-coding and/or non-coding exonic sequences), but may also include intronic sequences and untranslated regulatory sequences. Thus, any protein coding sequence may be either contiguous or separated by introns. The important point is that the nucleic acid is isolated from remote and unimportant flanking sequences and is of appropriate length such that it can be subjected to the specific manipulations or uses described herein such as recombinant protein expression, preparation of probes and primers for assaying the SNP position, and other uses specific to the SNP-containing nucleic acid sequences.

An isolated SNP-containing nucleic acid molecule can comprise, for example, a full-length gene or transcript, such as a gene isolated from genomic DNA (e.g., by cloning or PCR amplification), a cDNA molecule, or an mRNA transcript molecule. Furthermore, fragments of such full-length genes and transcripts that contain one or more SNPs disclosed herein are also encompassed by the present invention.

Thus, the present invention also encompasses fragments of the nucleic acid sequences including, but not limited to, SEQ ID NOs: 21, 26 and 27, and their complements. A fragment typically comprises a contiguous nucleotide sequence at least about 8 or more nucleotides, more preferably at least about 10 or more nucleotides, and even more preferably at least about 16 or more nucleotides. Further, a fragment could comprise at least about 18, 20, 21, 22, 25, 30, 40, 50, 60, 100, 250 or 500 (or any other number in-between) nucleotides in length. The length of the fragment will be based on its intended use. Such fragments can be isolated using nucleotide sequences such as, but not limited to, SEQ ID NOs: 15, 21, 24, 25, 26 and 27 for the synthesis of a polynucleotide probe. For example, a fragment may comprise nucleotides 3370-3400, 3360-3500, 3350-3600, 3340-3700, 3330-3800, 3320-3900, 3310-4000, 3300-4100, of SEQ ID NOs: 24, 25, 26, or 27, for example, or any range in between. A labeled probe can then be used, for example, to screen a cDNA library, genomic DNA library, or mRNA to isolate nucleic acid corresponding to the region of interest. Further, primers can be used in amplification reactions, such as for purposes of assaying one or more SNPs sites or for cloning specific regions of a gene.

An isolated nucleic acid molecule of the present invention further encompasses a SNP-containing polynucleotide that is the product of any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., Proc. Natl. Acad. Sci. USA 87: 1874, 1990). Based on such methodologies, a person skilled in the art can readily design primers in any suitable regions 5' and 3' to a SNP disclosed herein. Such primers may be used to amplify DNA of any length so long that it contains the SNP of interest in its sequence.

As used herein, an "amplified polynucleotide" of the invention is a SNP-containing nucleic acid molecule whose amount has been increased at least two fold by any nucleic acid amplification method performed in vitro as compared to its starting amount in a test sample. In other preferred embodiments, an amplified polynucleotide is the result of at least ten fold, fifty fold, one hundred fold, one thousand fold, or even ten thousand fold increase as compared to its starting amount in a test sample. In a typical PCR amplification, a polynucleotide of interest is often amplified at least fifty thousand fold in amount over the unamplified genomic DNA, but the precise amount of amplification needed for an assay depends on the sensitivity of the subsequent detection method used.

Generally, an amplified polynucleotide is at least about 10 nucleotides in length. More typically, an amplified polynucleotide is at least about 16 nucleotides in length. In a preferred embodiment of the invention, an amplified polynucleotide is at least about 20 nucleotides in length. In a more preferred embodiment of the invention, an amplified polynucleotide is at least about 21, 22, 23, 24, 25, 30, 35, 40, 45, 50, or 60 nucleotides in length. In yet another preferred embodiment of the invention, an amplified polynucleotide is at least about 100, 200, or 300 nucleotides in length. While the total length of an amplified polynucleotide of the invention can be as long as an exon, an intron, a 5' UTR, a 3' UTR, or the entire gene where the SNP of interest resides, an amplified product is typically no greater than about 1,000 nucleotides in length (although certain amplification methods may generate amplified products greater than 1000 nucleotides in length). More preferably, an amplified polynucleotide is not greater than about 600 nucleotides in length. It is understood that irrespective of the length of an amplified polynucleotide, a SNP of interest may be located anywhere along its sequence.

In a specific embodiment of the invention, the amplified product is at least about 21 nucleotides in length, and comprises a SNP in a let-7 complementary site (LCS) that modifies binding of a let-7 miRNA family member. In a specific embodiment, the amplified product is at least about 21 nucleotides in length, and comprises SEQ ID NOs: 21, 26, or 27. Such a product may have additional sequences on its 5' end or 3' end or both. In another embodiment, the amplified product is about 101 nucleotides in length, and it contains a SNP disclosed herein. Preferably, the SNP is located at the middle of the amplified product (e.g., at position 101 in an amplified product that is 201 nucleotides in length, or at position 51 in an amplified product that is 101 nucleotides in length), or within 1, 2, 3, 4, 5, 6, 7, 8, 9, 10, 12, 15, or 20 nucleotides from the middle of the amplified product (however, as indicated above, the SNP of interest may be located anywhere along the length of the amplified product).

The present invention provides isolated nucleic acid molecules that comprise, consist of, or consist essentially of one or more polynucleotide sequences that contain one or more SNPs disclosed herein, complements thereof, and SNP-containing fragments thereof.

Accordingly, the present invention provides nucleic acid molecules that consist of any of the nucleotide sequences of SEQ ID NO: 21, 26 and 27. A nucleic acid molecule consists of a nucleotide sequence when the nucleotide sequence is the complete nucleotide sequence of the nucleic acid molecule.

The present invention further provides nucleic acid molecules that consist essentially of any of the nucleotide sequences of SEQ ID NO: 21, 26 and 27. A nucleic acid molecule consists essentially of a nucleotide sequence when such a nucleotide sequence is present with only a few additional nucleotide residues in the final nucleic acid molecule.

The present invention further provides nucleic acid molecules that comprise any of the nucleotide sequences of SEQ ID NOs: 21, 26 or 27. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleotide residues, such as residues that are naturally associated with it or heterologous nucleotide sequences. Such a nucleic acid molecule can have one to a few additional nucleotides or can comprise many more additional nucleotides. A brief description of how various types of these nucleic acid molecules can be readily made and isolated is provided below, and such techniques are well known to those of ordinary skill in the art (Sambrook and Russell, 2000, Molecular Cloning: A Laboratory Manual, Cold Spring Harbor Press, NY).

The isolated nucleic acid molecules include, but are not limited to, nucleic acid molecules having a sequence encoding a peptide alone, a sequence encoding a mature peptide and additional coding sequences such as a leader or secretory sequence (e.g., a pre-pro or pro-protein sequence), a sequence encoding a mature peptide with or without additional coding sequences, plus additional non-coding sequences, for example introns and non-coding 5' and 3' sequences such as transcribed but untranslated sequences that play a role in, for example, transcription, mRNA processing (including splicing and polyadenylation signals), ribosome binding, and/or stability of mRNA. In addition, the nucleic acid molecules may be fused to heterologous marker sequences encoding, for example, a peptide that facilitates purification.

Isolated nucleic acid molecules can be in the form of RNA, such as mRNA, or in the form DNA, including cDNA and genomic DNA, which may be obtained, for example, by molecular cloning or produced by chemical synthetic techniques or by a combination thereof (Sambrook and Russell, 2000, Molecular Cloning: A Laboratory Manual, Cold Spring Harbor Press, NY). Furthermore, isolated nucleic acid molecules, particularly SNP detection reagents such as probes and primers, can also be partially or completely in the form of one or more types of nucleic acid analogs, such as peptide nucleic acid (PNA) (U.S. Pat. Nos. 5,539,082; 5,527,675; 5,623,049; 5,714,331). The nucleic acid, especially DNA, can be double-stranded or single-stranded. Single-stranded nucleic acid can be the coding strand (sense strand) or the complementary non-coding strand (anti-sense strand). DNA, RNA, or PNA segments can be assembled, for example, from fragments of the human genome (in the case of DNA or RNA) or single nucleotides, short oligonucleotide linkers, or from a series of oligonucleotides, to provide a synthetic nucleic acid molecule. Nucleic acid molecules can be readily synthesized using the sequences provided herein as a reference; oligonucleotide and PNA oligomer synthesis techniques are well known in the art (see, e.g., Corey, "Peptide nucleic acids: expanding the scope of nucleic acid recognition", Trends Biotechnol. 1997 June; 15(6):224-9, and Hyrup et al., "Peptide nucleic acids (PNA): synthesis, properties and potential applications", Bioorg Med Chem. 1996 January; 4(1):5-23). Furthermore, large-scale automated oligonucleotide/PNA synthesis (including synthesis on an array or bead surface or other solid support) can readily be accomplished using commercially available nucleic acid synthesizers, such as the Applied Biosystems (Foster City, Calif.) 3900 High-Throughput DNA Synthesizer or Expedite 8909 Nucleic Acid Synthesis System, and the sequence information provided herein.

The present invention encompasses nucleic acid analogs that contain modified, synthetic, or non-naturally occurring nucleotides or structural elements or other alternative/modified nucleic acid chemistries known in the art. Such nucleic acid analogs are useful, for example, as detection reagents (e.g., primers/probes) for detecting one or more SNPs identified in SEQ ID NOs: 21, 26 and 27. Furthermore, kits/systems (such as beads, arrays, etc.) that include these analogs are also encompassed by the present invention. For example, PNA oligomers that are based on the polymorphic sequences of the present invention are specifically contemplated. PNA oligomers are analogs of DNA in which the phosphate backbone is replaced with a peptide-like backbone (Lagriffoul et al., Bioorganic & Medicinal Chemistry Letters, 4: 1081-1082 (1994), Petersen et al., Bioorganic & Medicinal Chemistry Letters, 6: 793-796 (1996), Kumar et al., Organic Letters 3(9): 1269-1272 (2001), WO96/04000). PNA hybridizes to complementary RNA or DNA with higher affinity and specificity than conventional oligonucleotides and oligonucleotide analogs. The properties of PNA enable novel molecular biology and biochemistry applications unachievable with traditional oligonucleotides and peptides.

Additional examples of nucleic acid modifications that improve the binding properties and/or stability of a nucleic acid include the use of base analogs such as inosine, intercalators (U.S. Pat. No. 4,835,263) and the minor groove binders (U.S. Pat. No. 5,801,115). Thus, references herein to nucleic acid molecules, SNP-containing nucleic acid molecules, SNP detection reagents (e.g., probes and primers), oligonucleotides/polynucleotides include PNA oligomers and other nucleic acid analogs. Other examples of nucleic acid analogs and alternative/modified nucleic acid chemistries known in the art are described in Current Protocols in Nucleic Acid Chemistry, John Wiley & Sons, N.Y. (2002).

Further variants of the nucleic acid molecules including, but not limited to those identified as SEQ ID NOs: 21, 26 and 27, such as naturally occurring allelic variants (as well as orthologs and paralogs) and synthetic variants produced by mutagenesis techniques, can be identified and/or produced using methods well known in the art. Such further variants can comprise a nucleotide sequence that shares at least 70-80%, 80-85%, 85-90%, 91%, 92%, 93%, 94%, 95%, 96%, 97%, 98%, or 99% sequence identity with a nucleic acid sequence disclosed as SEQ ID NOs: 21, 26 or 27 (or a fragment thereof) and that includes a novel SNP allele disclosed as SEQ ID NOs: 21, 26 or 27. Thus, the present invention specifically contemplates isolated nucleic acid molecule that have a certain degree of sequence variation compared with the sequences of SEQ ID NOs: 21, 26 and 27, but that contain a novel SNP allele disclosed herein. In other words, as long as an isolated nucleic acid molecule contains a novel SNP allele disclosed herein, other portions of the nucleic acid molecule that flank the novel SNP allele can vary to some degree from the specific sequences identified herein as SEQ ID NOs: 21, 26, and 27.

The comparison of sequences and determination of percent identity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch algorithm (J. Mol. Biol. (48):444-453 (1970)) which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6.

In yet another preferred embodiment, the percent identity between two nucleotide sequences is determined using the GAP program in the GCG software package (Devereux, J., et al., Nucleic Acids Res. 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12, and a gap penalty of 4.

The nucleotide and amino acid sequences of the present invention can further be used as a "query sequence" to perform a search against sequence databases to, for example, identify other family members or related sequences. Such searches can be performed using the NBLAST and XBLAST programs (version 2.0) of Altschul, et al. (J. Mol. Biol. 215: 403-10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (Nucleic Acids Res. 25(17):3389-3402 (1997)). When utilizing BLAST and gapped BLAST programs, the default parameters of the respective programs (e.g., XBLAST and NBLAST) can be used. In addition to BLAST, examples of other search and sequence comparison programs used in the art include, but are not limited to, FASTA (Pearson, Methods Mol. Biol. 25, 365-389 (1994)) and KERR (Dufresne et al., Nat Biotechnol 2002 December; 20(12): 1269-71). For further information regarding bioinformatics techniques, see Current Protocols in Bioinformatics, John Wiley & Sons, Inc., N.Y.

SNP Detection Reagents

In a specific aspect of the present invention, the sequences disclosed herein can be used for the design of SNP detection reagents. In a preferred embodiment, sequences of SEQ ID NOs: 21, 24, 25, 26, and 27 are used for the design of SNP detection reagents. Methods of the invention encompass all sequences comprising let-7 complementary sites (LCSs). As such, any sequence comprising at least one LCS can be used to design a SNP detection reagent. As used herein, a "SNP detection reagent" is a reagent that specifically detects a specific target SNP position disclosed herein, and that is preferably specific for a particular nucleotide (allele) of the target SNP position (i.e., the detection reagent preferably can differentiate between different alternative nucleotides at a target SNP position, thereby allowing the identity of the nucleotide present at the target SNP position to be determined). Typically, such detection reagent hybridizes to a target SNP-containing nucleic acid molecule by complementary base-pairing in a sequence specific manner, and discriminates the target variant sequence from other nucleic acid sequences such as an art-known form in a test sample. An example of a detection reagent is a probe that hybridizes to a target nucleic acid containing SEQ ID NO: 21. In a preferred embodiment, such a probe can differentiate between nucleic acids having a particular nucleotide (allele) at a target SNP position from other nucleic acids that have a different nucleotide at the same target SNP position. In addition, a detection reagent may hybridize to a specific region 5' and/or 3' to a SNP position, particularly a region corresponding the 3'UTR. Another example of a detection reagent is a primer which acts as an initiation point of nucleotide extension along a complementary strand of a target polynucleotide. The SNP sequence information provided herein is also useful for designing primers, e.g. allele-specific primers, to amplify (e.g., using PCR) any SNP of the present invention.

In one preferred embodiment of the invention, a SNP detection reagent is an isolated or synthetic DNA or RNA polynucleotide probe or primer or PNA oligomer, or a combination of DNA, RNA and/or PNA, that hybridizes to a segment of a target nucleic acid molecule containing a SNP located within a LCS. In a specific embodiment, a SNP detection reagent is an isolated or synthetic DNA or RNA polynucleotide probe or primer or PNA oligomer, or a combination of DNA, RNA and/or PNA, that hybridizes to a segment of a target nucleic acid molecule containing SEQ ID NO: 21. A detection reagent in the form of a polynucleotide may optionally contain modified base analogs, intercalators or minor groove binders. Multiple detection reagents such as probes may be, for example, affixed to a solid support (e.g., arrays or beads) or supplied in solution (e.g., probe/primer sets for enzymatic reactions such as PCR, RT-PCR, TaqMan assays, or primer-extension reactions) to form a SNP detection kit.

A probe or primer typically is a substantially purified oligonucleotide or PNA oligomer. Such oligonucleotide typically comprises a region of complementary nucleotide sequence that hybridizes under stringent conditions to at least about 8, 10, 12, 16, 18, 20, 21, 22, 25, 30, 40, 50, 60, 100 (or any other number in-between) or more consecutive nucleotides in a target nucleic acid molecule. Depending on the particular assay, the consecutive nucleotides can either include the target SNP position, or be a specific region in close enough proximity 5' and/or 3' to the SNP position to carry out the desired assay.

It will be apparent to one of skill in the art that such primers and probes are directly useful as reagents for genotyping the SNPs of the present invention, and can be incorporated into any kit/system format.

In order to produce a probe or primer specific for a target SNP-containing sequence, the gene/transcript and/or context sequence surrounding the SNP of interest is typically examined using a computer algorithm which starts at the 5' or at the 3' end of the nucleotide sequence. Typical algorithms will then identify oligomers of defined length that are unique to the gene/SNP context sequence, have a GC content within a range suitable for hybridization, lack predicted secondary structure that may interfere with hybridization, and/or possess other desired characteristics or that lack other undesired characteristics.

A primer or probe of the present invention is typically at least about 8 nucleotides in length. In one embodiment of the invention, a primer or a probe is at least about 10 nucleotides in length. In a preferred embodiment, a primer or a probe is at least about 12 nucleotides in length. In a more preferred embodiment, a primer or probe is at least about 16, 17, 18, 19, 20, 21, 22, 23, 24 or 25 nucleotides in length. While the maximal length of a probe can be as long as the target sequence to be detected, depending on the type of assay in which it is employed, it is typically less than about 50, 60, 65, or 70 nucleotides in length. In the case of a primer, it is typically less than about 30 nucleotides in length. In a specific preferred embodiment of the invention, a primer or a probe is within the length of about 18 and about 28 nucleotides. However, in other embodiments, such as nucleic acid arrays and other embodiments in which probes are affixed to a substrate, the probes can be longer, such as on the order of 30-70, 75, 80, 90, 100, or more nucleotides in length (see the section below entitled "SNP Detection Kits and Systems").

For analyzing SNPs, it may be appropriate to use oligonucleotides specific for alternative SNP alleles. Such oligonucleotides which detect single nucleotide variations in target sequences may be referred to by such terms as "allele-specific oligonucleotides", "allele-specific probes", or "allele-specific primers". The design and use of allele-specific probes for analyzing polymorphisms is described in, e.g., Mutation Detection A Practical Approach, ed. Cotton et al. Oxford University Press, 1998; Saiki et al., Nature 324, 163-166 (1986); Dattagupta, EP235,726; and Saiki, WO 89/11548.

While the design of each allele-specific primer or probe depends on variables such as the precise composition of the nucleotide sequences flanking a SNP position in a target nucleic acid molecule, and the length of the primer or probe, another factor in the use of primers and probes is the stringency of the condition under which the hybridization between the probe or primer and the target sequence is performed. Higher stringency conditions utilize buffers with lower ionic strength and/or a higher reaction temperature, and tend to require a more perfect match between probe/primer and a target sequence in order to form a stable duplex. If the stringency is too high, however, hybridization may not occur at all. In contrast, lower stringency conditions utilize buffers with higher ionic strength and/or a lower reaction temperature, and permit the formation of stable duplexes with more mismatched bases between a probe/primer and a target sequence. By way of example and not limitation, exemplary conditions for high stringency hybridization conditions using an allele-specific probe are as follows: Prehybridization with a solution containing 5.times. standard saline phosphate EDTA (SSPE), 0.5% NaDodSO.sub.4 (SDS) at 55.degree. C., and incubating probe with target nucleic acid molecules in the same solution at the same temperature, followed by washing with a solution containing 2.times.SSPE, and 0.1% SDS at 55.degree. C. or room temperature.

Moderate stringency hybridization conditions may be used for allele-specific primer extension reactions with a solution containing, e.g., about 50 mM KCl at about 46.degree. C. Alternatively, the reaction may be carried out at an elevated temperature such as 60.degree. C. In another embodiment, a moderately stringent hybridization condition suitable for oligonucleotide ligation assay (OLA) reactions wherein two probes are ligated if they are completely complementary to the target sequence may utilize a solution of about 100 mM KCl at a temperature of 46.degree. C.

In a hybridization-based assay, allele-specific probes can be designed that hybridize to a segment of target DNA from one individual but do not hybridize to the corresponding segment from another individual due to the presence of different polymorphic forms (e.g., alternative SNP alleles/nucleotides) in the respective DNA segments from the two individuals. Hybridization conditions should be sufficiently stringent that there is a significant detectable difference in hybridization intensity between alleles, and preferably an essentially binary response, whereby a probe hybridizes to only one of the alleles or significantly more strongly to one allele. While a probe may be designed to hybridize to a target sequence that contains a SNP site such that the SNP site aligns anywhere along the sequence of the probe, the probe is preferably designed to hybridize to a segment of the target sequence such that the SNP site aligns with a central position of the probe (e.g., a position within the probe that is at least three nucleotides from either end of the probe). This design of probe generally achieves good discrimination in hybridization between different allelic forms.

In another embodiment, a probe or primer may be designed to hybridize to a segment of target DNA such that the SNP aligns with either the 5' most end or the 3' most end of the probe or primer. In a specific preferred embodiment which is particularly suitable for use in a oligonucleotide ligation assay (U.S. Pat. No. 4,988,617), the 3' most nucleotide of the probe aligns with the SNP position in the target sequence.

Oligonucleotide probes and primers may be prepared by methods well known in the art. Chemical synthetic methods include, but are limited to, the phosphotriester method described by Narang et al., 1979, Methods in Enzymology 68:90; the phosphodiester method described by Brown et al., 1979, Methods in Enzymology 68:109, the diethylphosphoamidate method described by Beaucage et al., 1981, Tetrahedron Letters 22:1859; and the solid support method described in U.S. Pat. No. 4,458,066.

Allele-specific probes are often used in pairs (or, less commonly, in sets of 3 or 4, such as if a SNP position is known to have 3 or 4 alleles, respectively, or to assay both strands of a nucleic acid molecule for a target SNP allele), and such pairs may be identical except for a one nucleotide mismatch that represents the allelic variants at the SNP position.

Commonly, one member of a pair perfectly matches a reference form of a target sequence that has a more common SNP allele (i.e., the allele that is more frequent in the target population) and the other member of the pair perfectly matches a form of the target sequence that has a less common SNP allele (i.e., the allele that is rarer in the target population). In the case of an array, multiple pairs of probes can be immobilized on the same support for simultaneous analysis of multiple different polymorphisms.

In one type of PCR-based assay, an allele-specific primer hybridizes to a region on a target nucleic acid molecule that overlaps a SNP position and only primes amplification of an allelic form to which the primer exhibits perfect complementarity (Gibbs, 1989, Nucleic Acid Res. 17 2427-2448). Typically, the primer's 3'-most nucleotide is aligned with and complementary to the SNP position of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e., the 3'-most position of the oligonucleotide aligns with the target SNP position) because this position is most destabilizing to elongation from the primer (see, e.g., WO 93/22456). This PCR-based assay can be utilized as part of the TaqMan assay, described below.

In a specific embodiment of the invention, a primer of the invention contains a sequence substantially complementary to a segment of a target SNP-containing nucleic acid molecule except that the primer has a mismatched nucleotide in one of the three nucleotide positions at the 3'-most end of the primer, such that the mismatched nucleotide does not base pair with a particular allele at the SNP site. In a preferred embodiment, the mismatched nucleotide in the primer is the second from the last nucleotide at the 3'-most position of the primer. In a more preferred embodiment, the mismatched nucleotide in the primer is the last nucleotide at the 3'-most position of the primer.

In another embodiment of the invention, a SNP detection reagent of the invention is labeled with a fluorogenic reporter dye that emits a detectable signal. While the preferred reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment of the invention, the detection reagent may be further labeled with a quencher dye such as Tamra, especially when the reagent is used as a self-quenching probe such as a TaqMan (U.S. Pat. Nos. 5,210,015 and 5,538,848) or Molecular Beacon probe (U.S. Pat. Nos. 5,118, 801 and 5,312,728), or other stemless or linear beacon probe (Livak et al., 1995, PCR Method Appl. 4:357-362; Tyagi et al., 1996, Nature Biotechnology 14: 303-308; Nazarenko et al., 1997, Nucl. Acids Res. 25:2516-2521; U.S. Pat. Nos. 5,866,336 and 6,117,635).

The detection reagents of the invention may also contain other labels, including but not limited to, biotin for streptavidin binding, hapten for antibody binding, and oligonucleotide for binding to another complementary oligonucleotide such as pairs of zipcodes.

The present invention also contemplates reagents that do not contain (or that are complementary to) a SNP nucleotide identified herein but that are used to assay one or more SNPs disclosed herein. For example, primers that flank, but do not hybridize directly to a target SNP position provided herein are useful in primer extension reactions in which the primers hybridize to a region adjacent to the target SNP position (i.e., within one or more nucleotides from the target SNP site). During the primer extension reaction, a primer is typically not able to extend past a target SNP site if a particular nucleotide (allele) is present at that target SNP site, and the primer extension product can readily be detected in order to determine which SNP allele is present at the target SNP site. For example, particular ddNTPs are typically used in the primer extension reaction to terminate primer extension once a ddNTP is incorporated into the extension product (a primer extension product which includes a ddNTP at the 3'-most end of the primer extension product, and in which the ddNTP corresponds to a SNP disclosed herein, is a composition that is encompassed by the present invention). Thus, reagents that bind to a nucleic acid molecule in a region adjacent to a SNP site, even though the bound sequences do not necessarily include the SNP site itself, are also encompassed by the present invention.

SNP Detection Kits and Systems

A person skilled in the art will recognize that, based on the SNP and associated sequence information disclosed herein, detection reagents can be developed and used to assay any SNP of the present invention individually or in combination, and such detection reagents can be readily incorporated into one of the established kit or system formats which are well known in the art. The terms "kits" and "systems", as used herein in the context of SNP detection reagents, are intended to refer to such things as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, etc.). Accordingly, the present invention further provides SNP detection kits and systems, including but not limited to, packaged probe and primer sets (e.g., TaqMan probe/primer sets), arrays/microarrays of nucleic acid molecules, and beads that contain one or more probes, primers, or other detection reagents for detecting one or more SNPs of the present invention. The kits/systems can optionally include various electronic hardware components; for example, arrays ("DNA chips") and microfluidic systems ("lab-on-a-chip" systems) provided by various manufacturers typically comprise hardware components. Other kits/systems (e.g., probe/primer sets) may not include electronic hardware components, but may be comprised of, for example, one or more SNP detection reagents (along with, optionally, other biochemical reagents) packaged in one or more containers.

In some embodiments, a SNP detection kit typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as amplification and/or detection of a SNP-containing nucleic acid molecule. A kit may further contain means for determining the amount of a target nucleic acid, and means for comparing the amount with a standard, and can comprise instructions for using the kit to detect the SNP-containing nucleic acid molecule of interest. In one embodiment of the present invention, kits are provided which contain the necessary reagents to carry out one or more assays to detect one or more SNPs disclosed herein. In a preferred embodiment of the present invention, SNP detection kits/systems are in the form of nucleic acid arrays, or compartmentalized kits, including microfluidic/lab-on-a-chip systems.

SNP detection kits/systems may contain, for example, one or more probes, or pairs of probes, that hybridize to a nucleic acid molecule at or near each target SNP position. Multiple pairs of allele-specific probes may be included in the kit/system to simultaneously assay large numbers of SNPs, at least one of which is a SNP of the present invention. In some kits/systems, the allele-specific probes are immobilized to a substrate such as an array or bead.

The terms "arrays", "microarrays", and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619), all of which are incorporated herein in their entirety by reference. In other embodiments, such arrays are produced by the methods described by Brown et al., U.S. Pat. No. 5,807,522.

Nucleic acid arrays are reviewed in the following references: Zammatteo et al., "New chips for molecular biology and diagnostics", Biotechnol Annu Rev. 2002; 8:85-101; Sosnowski et al., "Active microelectronic array system for DNA hybridization, genotyping and pharmacogenomic applications", Psychiatr Genet. 2002 December; 12(4):181-92; Heller, "DNA microarray technology: devices, systems, and applications", Annu Rev Biomed Eng. 2002; 4:129-53. Epub 2002 Mar. 22; Kolchinsky et al., "Analysis of SNPs and other genomic variations using gel-based chips", Hum Mutat. 2002 April; 19(4):343-60; and McGall et al., "High-density gene-chip oligonucleotide probe arrays", Adv Biochem Eng Biotechnol. 2002; 77:21-42.

Any number of probes, such as allele-specific probes, may be implemented in an array, and each probe or pair of probes can hybridize to a different SNP position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array.

A microarray can be composed of a large number of unique, single-stranded polynucleotides, usually either synthetic antisense polynucleotides or fragments of cDNAs, fixed to a solid support. Typical polynucleotides are preferably about 6-60 nucleotides in length, more preferably about 15-30 nucleotides in length, and most preferably about 18-25 nucleotides in length. For certain types of microarrays or other detection kits/systems, it may be preferable to use oligonucleotides that are only about 7-20 nucleotides in length. In other types of arrays, such as arrays used in conjunction with chemiluminescent detection technology, preferred probe lengths can be, for example, about 15-80 nucleotides in length, preferably about 50-70 nucleotides in length, more preferably about 55-65 nucleotides in length, and most preferably about 60 nucleotides in length. The microarray or detection kit can contain polynucleotides that cover the known 5' or 3' sequence of a gene/transcript or target SNP site, sequential polynucleotides that cover the full-length sequence of a gene/transcript; or unique polynucleotides selected from particular areas along the length of a target gene/transcript sequence, particularly areas corresponding to one or more SNPs, for instance the LCS6 SNP identified within SEQ ID NOs: 21, 26, and 27. Polynucleotides used in the microarray or detection kit can be specific to a SNP or SNPs of interest (e.g., specific to a particular SNP allele at a target SNP site, or specific to particular SNP alleles at multiple different SNP sites), or specific to a polymorphic gene/transcript or genes/transcripts of interest.

Hybridization assays based on polynucleotide arrays rely on the differences in hybridization stability of the probes to perfectly matched and mismatched target sequence variants. For SNP genotyping, it is generally preferable that stringency conditions used in hybridization assays are high enough such that nucleic acid molecules that differ from one another at as little as a single SNP position can be differentiated (e.g., typical SNP hybridization assays are designed so that hybridization will occur only if one particular nucleotide is present at a SNP position, but will not occur if an alternative nucleotide is present at that SNP position). Such high stringency conditions may be preferable when using, for example, nucleic acid arrays of allele-specific probes for SNP detection. Such high stringency conditions are described in the preceding section, and are well known to those skilled in the art and can be found in, for example, Current Protocols in Molecular Biology, John Wiley & Sons, N.Y. (1989), 6.3.1-6.3.6.

In other embodiments, the arrays are used in conjunction with chemiluminescent detection technology. The following patents and patent applications, which are all hereby incorporated by reference, provide additional information pertaining to chemiluminescent detection: U.S. patent application Ser. Nos. 10/620,332 and 10/620,333 describe chemiluminescent approaches for microarray detection; U.S. Pat. Nos. 6,124,478, 6,107,024, 5,994,073, 5,981,768, 5,871,938, 5,843,681, 5,800,999, and 5,773,628 describe methods and compositions of dioxetane for performing chemiluminescent detection; and U.S. published application US2002/0110828 discloses methods and compositions for microarray controls.

In one embodiment of the invention, a nucleic acid array can comprise an array of probes of about 15-25 nucleotides in length. In further embodiments, a nucleic acid array can comprise any number of probes, in which at least one probe is capable of detecting the LCS6 SNP of SEQ ID NOs: 21, 26 and 27, and/or at least one probe comprises a fragment of one of the sequences selected from the group consisting of those disclosed in the Sequence Listing, sequences complementary thereto, and fragment thereof comprising at least about 8 consecutive nucleotides, preferably 10, 12, 15, 16, 18, 20, more preferably 22, 25, 30, 40, 47, 50, 55, 60, 65, 70, 80, 90, 100, or more consecutive nucleotides (or any other number in-between) and containing (or being complementary to) a novel SNP allele disclosed in SEQ ID NOs: 21, 26, and 27. In some embodiments, the nucleotide complementary to the SNP site is within 5, 4, 3, 2, or 1 nucleotide from the center of the probe, more preferably at the center of said probe.

A polynucleotide probe can be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more polynucleotides, or any other number which lends itself to the efficient use of commercially available instrumentation.

Using such arrays or other kits/systems, the present invention provides methods of identifying the SNPs disclosed herein in a test sample. Such methods typically involve incubating a test sample of nucleic acids with an array comprising one or more probes corresponding to at least one SNP position of the present invention, and assaying for binding of a nucleic acid from the test sample with one or more of the probes. Conditions for incubating a SNP detection reagent (or a kit/system that employs one or more such SNP detection reagents) with a test sample vary. Incubation conditions depend on such factors as the format employed in the assay, the detection methods employed, and the type and nature of the detection reagents used in the assay. One skilled in the art will recognize that any one of the commonly available hybridization, amplification and array assay formats can readily be adapted to detect the SNPs disclosed herein.

A SNP detection kit/system of the present invention may include components that are used to prepare nucleic acids from a test sample for the subsequent amplification and/or detection of a SNP-containing nucleic acid molecule. Such sample preparation components can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue specimens. The test samples used in the above-described methods will vary based on such factors as the assay format, nature of the detection method, and the specific tissues, cells or extracts used as the test sample to be assayed. Methods of preparing nucleic acids, proteins, and cell extracts are well known in the art and can be readily adapted to obtain a sample that is compatible with the system utilized. Automated sample preparation systems for extracting nucleic acids from a test sample are commercially available, and examples are Qiagen's BioRobot 9600, Applied Biosystems' PRISM 6700, and Roche Molecular Systems' COBAS AmpliPrep System.

Another form of kit contemplated by the present invention is a compartmentalized kit. A compartmentalized kit includes any kit in which reagents are contained in separate containers. Such containers include, for example, small glass containers, plastic containers, strips of plastic, glass or paper, or arraying material such as silica. Such containers allow one to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one probe or other SNP detection reagent for detecting one or more SNPs of the present invention, one or more containers which contain wash reagents (such as phosphate buffered saline, Tris-buffers, etc.), and one or more containers which contain the reagents used to reveal the presence of the bound probe or other SNP detection reagents. The kit can optionally further comprise compartments and/or reagents for, for example, nucleic acid amplification or other enzymatic reactions such as primer extension reactions, hybridization, ligation, electrophoresis (preferably capillary electrophoresis), mass spectrometry, and/or laser-induced fluorescent detection. The kit may also include instructions for using the kit. Exemplary compartmentalized kits include microfluidic devices known in the art (see, e.g., Weigl et al., "Lab-on-a-chip for drug development", Adv Drug Deliv Rev. 2003 Feb. 24; 55(3):349-77). In such microfluidic devices, the containers may be referred to as, for example, microfluidic "compartments", "chambers", or "channels".

Microfluidic devices, which may also be referred to as "lab-on-a-chip" systems, biomedical micro-electro-mechanical systems (bioMEMs), or multicomponent integrated systems, are exemplary kits/systems of the present invention for analyzing SNPs. Such systems miniaturize and compartmentalize processes such as probe/target hybridization, nucleic acid amplification, and capillary electrophoresis reactions in a single functional device. Such microfluidic devices typically utilize detection reagents in at least one aspect of the system, and such detection reagents may be used to detect one or more SNPs of the present invention. One example of a microfluidic system is disclosed in U.S. Pat. No. 5,589,136, which describes the integration of PCR amplification and capillary electrophoresis in chips. Exemplary microfluidic systems comprise a pattern of microchannels designed onto a glass, silicon, quartz, or plastic wafer included on a microchip. The movements of the samples may be controlled by electric, electroosmotic or hydrostatic forces applied across different areas of the microchip to create functional microscopic valves and pumps with no moving parts. Varying the voltage can be used as a means to control the liquid flow at intersections between the micro-machined channels and to change the liquid flow rate for pumping across different sections of the microchip. See, for example, U.S. Pat. No. 6,153,073, Dubrow et al., and U.S. Pat. No. 6,156,181, Parce et al.

For genotyping SNPs, an exemplary microfluidic system may integrate, for example, nucleic acid amplification, primer extension, capillary electrophoresis, and a detection method such as laser induced fluorescence detection. In a first step of an exemplary process for using such an exemplary system, nucleic acid samples are amplified, preferably by PCR. Then, the amplification products are subjected to automated primer extension reactions using ddNTPs (specific fluorescence for each ddNTP) and the appropriate oligonucleotide primers to carry out primer extension reactions which hybridize just upstream of the targeted SNP. Once the extension at the 3' end is completed, the primers are separated from the unincorporated fluorescent ddNTPs by capillary electrophoresis. The separation medium used in capillary electrophoresis can be, for example, polyacrylamide, polyethyleneglycol or dextran. The incorporated ddNTPs in the single nucleotide primer extension products are identified by laser-induced fluorescence detection. Such an exemplary microchip can be used to process, for example, at least 96 to 384 samples, or more, in parallel.

Uses of Nucleic Acid Molecules

The nucleic acid molecules of the present invention have a variety of uses, especially in the assessing the risk of developing a disorder. Exemplary disorders include but are not limited to, inflammatory, degenerative, metabolic, proliferative, circulatory, cognitive, reproductive, and behavioral disorders. In a preferred embodiment of the invention the disorder is cancer. For example, the nucleic acid molecules are useful as hybridization probes, such as for genotyping SNPs in messenger RNA, transcript, cDNA, genomic DNA, amplified DNA or other nucleic acid molecules, and for isolating full-length cDNA and genomic clones.

A probe can hybridize to any nucleotide sequence along the entire length of a LCS-containing nucleic acid molecule. Preferably, a probe of the present invention hybridizes to a region of a target sequence that encompasses a SNP such as the sequences of SEQ ID NOs: 21, 26, and 27. More preferably, a probe hybridizes to a SNP-containing target sequence in a sequence-specific manner such that it distinguishes the target sequence from other nucleotide sequences which vary from the target sequence only by which nucleotide is present at the SNP site. Such a probe is particularly useful for detecting the presence of a SNP-containing nucleic acid in a test sample, or for determining which nucleotide (allele) is present at a particular SNP site (i.e., genotyping the SNP site).

A nucleic acid hybridization probe may be used for determining the presence, level, form, and/or distribution of nucleic acid expression. The nucleic acid whose level is determined can be DNA or RNA. Accordingly, probes specific for the SNPs described herein can be used to assess the presence, expression and/or gene copy number in a given cell, tissue, or organism. These uses are relevant for diagnosis of disorders involving an increase or decrease in gene expression relative to normal levels. In vitro techniques for detection of mRNA include, for example, Northern blot hybridizations and in situ hybridizations. In vitro techniques for detecting DNA include Southern blot hybridizations and in situ hybridizations (Sambrook and Russell, 2000, Molecular Cloning: A Laboratory Manual, Cold Spring Harbor Press, Cold Spring Harbor, N.Y.).

Thus, the nucleic acid molecules of the invention can be used as hybridization probes to detect the SNPs disclosed herein, thereby determining whether an individual with the polymorphisms is at risk for developing a disorder. Detection of a SNP associated with a disease phenotype provides a prognostic tool for an active disease and/or genetic predisposition to the disease.

The nucleic acid molecules of the invention are also useful for designing ribozymes corresponding to all, or a part, of an mRNA molecule expressed from a SNP-containing nucleic acid molecule described herein.

The nucleic acid molecules of the invention are also useful for constructing transgenic animals expressing all, or a part, of the nucleic acid molecules and variant peptides. The production of recombinant cells and transgenic animals having nucleic acid molecules which contain the LCS6 SNP disclosed herein allow, for example, effective clinical design of treatment compounds and dosage regimens.

SNP Genotyping Methods

The process of determining which specific nucleotide (i.e., allele) is present at each of one or more SNP positions, such as a SNP position in a nucleic acid molecule disclosed in SEQ ID NO: 21, 26 or 27, is referred to as SNP genotyping. The present invention provides methods of SNP genotyping, such as for use in screening for a variety of disorders, or determining predisposition thereto, or determining responsiveness to a form of treatment, or prognosis, or in genome mapping or SNP association analysis, etc.

Nucleic acid samples can be genotyped to determine which allele(s) is/are present at any given genetic region (e.g., SNP position) of interest by methods well known in the art. The neighboring sequence can be used to design SNP detection reagents such as oligonucleotide probes, which may optionally be implemented in a kit format. Exemplary SNP genotyping methods are described in Chen et al., "Single nucleotide polymorphism genotyping: biochemistry, protocol, cost and throughput", Pharmacogenomics J. 2003; 3(2):77-96; Kwok et al., "Detection of single nucleotide polymorphisms", Curr Issues Mol. Biol. 2003 April; 5(2):43-60; Shi, "Technologies for individual genotyping: detection of genetic polymorphisms in drug targets and disease genes", Am J Pharmacogenomics. 2002; 2(3):197-205; and Kwok, "Methods for genotyping single nucleotide polymorphisms", Annu Rev Genomics Hum Genet 2001; 2:235-58. Exemplary techniques for high-throughput SNP genotyping are described in Marnellos, "High-throughput SNP analysis for genetic association studies", Curr Opin Drug Discov Devel. 2003 May; 6(3):317-21. Common SNP genotyping methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

Various methods for detecting polymorphisms include, but are not limited to, methods in which protection from cleavage agents is used to detect mismatched bases in RNA/RNA or RNA/DNA duplexes (Myers et al., Science 230:1242 (1985); Cotton et al., PNAS 85:4397 (1988); and Saleeba et al., Meth. Enzymol. 217:286-295 (1992)), comparison of the electrophoretic mobility of variant and wild type nucleic acid molecules (Orita et al., PNAS 86:2766 (1989); Cotton et al., Mutat. Res. 285:125-144 (1993); and Hayashi et al., Genet. Anal. Tech. Appl. 9:73-79 (1992)), and assaying the movement of polymorphic or wild-type fragments in polyacrylamide gels containing a gradient of denaturant using denaturing gradient gel electrophoresis (DGGE) (Myers et al., Nature 313:495 (1985)). Sequence variations at specific locations can also be assessed by nuclease protection assays such as RNase and SI protection or chemical cleavage methods.

In a preferred embodiment, SNP genotyping is performed using the TaqMan assay, which is also known as the 5' nuclease assay (U.S. Pat. Nos. 5,210,015 and 5,538,848). The TaqMan assay detects the accumulation of a specific amplified product during PCR. The TaqMan assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively, or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

Preferred TaqMan primer and probe sequences can readily be determined using the SNP and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the SNPs of the present invention are useful in prognostic assays for a variety of disorders including cancer, and can be readily incorporated into a kit format. The present invention also includes modifications of the Taqman assay well known in the art such as the use of Molecular Beacon probes (U.S. Pat. Nos. 5,118,801 and 5,312,728) and other variant formats (U.S. Pat. Nos. 5,866,336 and 6,117,635).

The identity of polymorphisms may also be determined using a mismatch detection technique, including but not limited to the RNase protection method using riboprobes (Winter et al., Proc. Natl. Acad Sci. USA 82:7575, 1985; Meyers et al., Science 230:1242, 1985) and proteins which recognize nucleotide mismatches, such as the *E. coli* mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nuci. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruano et al., Nucl. Acids Res. 17:8392, 1989; Ruano et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO89/10414).

Another preferred method for genotyping the SNPs of the present invention is the use of two oligonucleotide probes in an OLA (see, e.g., U.S. Pat. No. 4,988,617). In this method, one probe hybridizes to a segment of a target nucleic acid with its 3' most end aligned with the SNP site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the SNP site. If there is a mismatch, ligation would not occur. After the reaction, the ligated probes are separated from the target nucleic acid molecule, and detected as indicators of the presence of a SNP.

The following patents, patent applications, and published international patent applications, which are all hereby incorporated by reference, provide additional information pertaining to techniques for carrying out various types of OLA: U.S. Pat. Nos. 6,027,889, 6,268,148, 5,494,810, 5,830,711, and 6,054,564 describe OLA strategies for performing SNP detection; WO 97/31256 and WO 00/56927 describe OLA strategies for performing SNP detection using universal arrays, wherein a zipcode sequence can be introduced into one of the hybridization probes, and the resulting product, or amplified product, hybridized to a universal zip code array; U.S. application US01/17329 (and Ser. No. 09/584,905) describes OLA (or LDR) followed by PCR, wherein zipcodes are incorporated into OLA probes, and amplified PCR products are determined by electrophoretic or universal zipcode array readout; U.S. application 60/427,818, 60/445,636, and 60/445,494 describe SNPlex methods and software for multiplexed SNP detection using OLA followed by PCR, wherein zipcodes are incorporated into OLA probes, and amplified PCR products are hybridized with a zipchute reagent, and the identity of the SNP determined from electrophoretic readout of the zipchute. In some embodiments, OLA is carried out prior to PCR (or another method of nucleic acid amplification). In other embodiments, PCR (or another method of nucleic acid amplification) is carried out prior to OLA.

Another method for SNP genotyping is based on mass spectrometry. Mass spectrometry takes advantage of the unique mass of each of the four nucleotides of DNA. SNPs can be unambiguously genotyped by mass spectrometry by measuring the differences in the mass of nucleic acids having alternative SNP alleles. MALDI-TOF (Matrix Assisted Laser Desorption Ionization-Time of Flight) mass spectrometry technology is preferred for extremely precise determinations of molecular mass, such as SNPs. Numerous approaches to SNP analysis have been developed based on mass spectrometry. Preferred mass spectrometry-based methods of SNP genotyping include primer extension assays, which can also be utilized in combination with other approaches, such as traditional gel-based formats and microarrays.

Typically, the primer extension assay involves designing and annealing a primer to a template PCR amplicon upstream (5') from a target SNP position. A mix of dideoxynucleotide triphosphates (ddNTPs) and/or deoxynucleotide triphosphates (dNTPs) are added to a reaction mixture containing template (e.g., a SNP-containing nucleic acid molecule which has typically been amplified, such as by PCR), primer, and DNA polymerase. Extension of the primer terminates at the first position in the template where a nucleotide complementary to one of the ddNTPs in the mix occurs. The primer can be either immediately adjacent (i.e., the nucleotide at the 3' end of the primer hybridizes to the nucleotide next to the target SNP site) or two or more nucleotides removed from the SNP position. If the primer is several nucleotides removed from the target SNP position, the only limitation is that the template sequence between the 3' end of the primer and the SNP position cannot contain a nucleotide of the same type as the one to be detected, or this will cause premature termination of the extension primer. Alternatively, if all four ddNTPs alone, with no dNTPs, are added to the reaction mixture, the primer will always be extended by only one nucleotide, corresponding to the target SNP position. In this instance, primers are designed to bind one nucleotide upstream from the SNP position (i.e., the nucleotide at the 3' end of the primer hybridizes to the nucleotide that is immediately adjacent to the target SNP site on the 5' side of the target SNP site). Extension by only one nucleotide is preferable, as it minimizes the overall mass of the extended primer, thereby increasing the resolution of mass differences between alternative SNP nucleotides. Furthermore, mass-tagged ddNTPs can be employed in the primer extension reactions in place of unmodified ddNTPs. This increases the mass difference between primers extended with these ddNTPs, thereby providing increased sensitivity and accuracy, and is particularly useful for typing heterozygous base positions. Mass-tagging also alleviates the need for intensive sample-preparation procedures and decreases the necessary resolving power of the mass spectrometer.

The extended primers can then be purified and analyzed by MALDI-TOF mass spectrometry to determine the identity of the nucleotide present at the target SNP position. In one method of analysis, the products from the primer extension reaction are combined with light absorbing crystals that form a matrix. The matrix is then hit with an energy source such as a laser to ionize and desorb the nucleic acid molecules into the gas-phase. The ionized molecules are then ejected into a flight tube and accelerated down the tube towards a detector. The time between the ionization event, such as a laser pulse, and collision of the molecule with the detector is the time of flight of that molecule. The time of flight is precisely correlated with the mass-to-charge ratio (m/z) of the ionized molecule. Ions with smaller m/z travel down the tube faster than ions with larger m/z and therefore the lighter ions reach the detector before the heavier ions. The time-of-flight is then converted into a corresponding, and highly precise, m/z. In this manner, SNPs can be identified based on the slight differences in mass, and the corresponding time of flight differences, inherent in nucleic acid molecules having different nucleotides at a single base position. For further information regarding the use of primer extension assays in conjunction with MALDI-TOF mass spectrometry for SNP genotyping, see, e.g., Wise et al., "A standard protocol for single nucleotide primer extension in the human genome using matrix-assisted laser desorption/ionization time-of-flight mass spectrometry", Rapid Commun Mass Spectrom. 2003; 17(11): 1195-202.

The following references provide further information describing mass spectrometry-based methods for SNP genotyping: Bocker, "SNP and mutation discovery using base-specific cleavage and MALDI-TOF mass spectrometry", Bioinformatics. 2003 July; 19 Suppl 1:144-153; Storm et al., "MALDI-TOF mass spectrometry-based SNP genotyping", Methods Mol. Biol. 2003; 212:241-62; Jurinke et al., "The use of MassARRAY technology for high throughput genotyping", Adv Biochem Eng Biotechnol. 2002; 77:57-74; and Jurinke et al., "Automated genotyping using the DNA MassArray technology", Methods Mol. Biol. 2002; 187:179-92.

SNPs can also be scored by direct DNA sequencing. A variety of automated sequencing procedures can be utilized ((1995) Biotechniques 19:448), including sequencing by mass spectrometry (see, e.g., PCT International Publication No. WO94/16101; Cohen et al., Adv. Chromatogr. 36:127-162 (1996); and Griffin et al., Appl. Biochem. Biotechnol. 38:147-159 (1993)). The nucleic acid sequences of the present invention enable one of ordinary skill in the art to readily design sequencing primers for such automated sequencing procedures. Commercial instrumentation, such as the Applied Biosystems 377, 3100, 3700, 3730, and 3730.times.1 DNA Analyzers (Foster City, Calif.), is commonly used in the art for automated sequencing.

Other methods that can be used to genotype the SNPs of the present invention include single-strand conformational polymorphism (SSCP), and denaturing gradient gel electrophoresis (DGGE) (Myers et al., Nature 313:495 (1985)). SSCP identifies base differences by alteration in electrophoretic migration of single stranded PCR products, as described in Orita et al., Proc. Nat. Acad. Single-stranded PCR products can be generated by heating or otherwise denaturing double stranded PCR products. Single-stranded nucleic acids may refold or form secondary structures that are partially dependent on the base sequence. The different electrophoretic mobilities of single-stranded amplification products are related to base-sequence differences at SNP positions. DGGE differentiates SNP alleles based on the different sequence-dependent stabilities and melting properties inherent in polymorphic DNA and the corresponding differences in electrophoretic migration patterns in a denaturing gradient gel (Erlich, ed., PCR Technology, Principles and Applications for DNA Amplification, W. H. Freeman and Co, New York, 1992, Chapter 7).

Sequence-specific ribozymes (U.S. Pat. No. 5,498,531) can also be used to score SNPs based on the development or loss of a ribozyme cleavage site. Perfectly matched sequences can be distinguished from mismatched sequences by nuclease cleavage digestion assays or by differences in melting temperature. If the SNP affects a restriction enzyme cleavage site, the SNP can be identified by alterations in restriction enzyme digestion patterns, and the corresponding changes in nucleic acid fragment lengths determined by gel electrophoresis SNP genotyping can include the steps of, for example, collecting a biological sample from a human subject (e.g., sample of tissues, cells, fluids, secretions, etc.), isolating nucleic acids (e.g., genomic DNA, mRNA or both) from the cells of the sample, contacting the nucleic acids with one or more primers which specifically hybridize to a region of the isolated nucleic acid containing a target SNP under conditions such that hybridization and amplification of the target nucleic acid region occurs, and determining the nucleotide present at the SNP position of interest, or, in some assays, detecting the presence or absence of an amplification product (assays can be designed so that hybridization and/or amplification will only occur if a particular SNP allele is present or absent). In some assays, the size of the amplification product is detected and compared to the length of a control sample; for example, deletions and insertions can be detected by a change in size of the amplified product compared to a normal genotype.

SNP genotyping is useful for numerous practical applications, as described below. Examples of such applications include, but are not limited to, SNP-disease association analysis, disease predisposition screening, disease diagnosis, disease prognosis, disease progression monitoring, determining therapeutic strategies based on an individual's genotype ("pharmacogenomics"), developing therapeutic agents based on SNP genotypes associated with a disease or likelihood of responding to a drug, stratifying a patient population for clinical trial for a treatment regimen, and predicting the likelihood that an individual will experience toxic side effects from a therapeutic agent.

Disease Screening Assays

Information on association/correlation between genotypes and disease-related phenotypes can be exploited in several ways. For example, in the case of a highly statistically significant association between one or more SNPs with predisposition to a disease for which treatment is available, detection of such a genotype pattern in an individual may justify immediate administration of treatment, or at least the institution of regular monitoring of the individual. In the case of a weaker but still statistically significant association between a SNP and a human disease, immediate therapeutic intervention or monitoring may not be justified after detecting the susceptibility allele or SNP. Nevertheless, the subject can be motivated to begin simple life-style changes (e.g., diet, exercise, quit smoking, increased monitoring/examination) that can be accomplished at little or no cost to the individual but would confer potential benefits in reducing the risk of developing conditions for which that individual may have an increased risk by virtue of having the susceptibility allele(s).

In one aspect, the invention provides methods of identifying SNPs which increase the risk, susceptibility, or probability of developing a disease such as a cell proliferative disorder (e.g. cancer). In a further aspect, the invention provides methods for identifying a subject at risk for developing a disease, determining the prognosis a disease or predicting the onset of a disease. For example, a subject's risk of developing a cell proliferative disease, the prognosis of an individual with a disease, or the predicted onset of a cell proliferative disease is are determined by detecting a mutation in the 3' untranslated region (UTR) of a member of the RAS gene superfamily. In a specific example, a subject's risk of developing a cell proliferative disease, the prognosis of an individual with a disease, or the predicted onset of a cell proliferative disease is are determined by detecting a mutation in the 3' untranslated region (UTR) of KRAS. Identification of the mutation indicates an increases risk of developing a cell proliferative disorder, poor prognosis or an earlier onset of developing a cell proliferative disorder.

The mutation is for a example a deletion, insertion, inversion, substitution, frameshift or recombination. In one aspect, the mutation occurs within a let-7 complementary site (LCS). The mutation is for example, one or more SNPs in the 3' untranslated region of RAS. RAS includes KRAS, HRAS, or NRAS. For example the mutation is a SNP at position 4 of LCS6 of KRAS of which results in a uracil (U) or thymine (T) to guanine (G) conversion.

The mutation modulates, e.g. increases or decreases, the binding efficacy of an miRNA, such as a let-7 family miRNA. By "binding efficacy" it is meant the ability of a miRNA molecule to bind to a target gene or transcript, and therefore, silence, decrease, reduce, inhibit, or prevent the transcription or translation of the target gene or transcript, respectively. Binding efficacy is determined by the ability of the miRNA to inhibit protein production or inhibit reporter protein production. Alternatively, or in addition, binding efficacy is defined as binding energy and measured in minimum free energy (mfe) (kilocalories/mole) (see FIGS. 26 and 16).

"Risk" in the context of the present invention, relates to the probability that an event will occur over a specific time period, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion.

"Risk evaluation," or "evaluation of risk" in the context of the present invention encompasses making a prediction of the probability, odds, or likelihood that an event or disease state may occur, the rate of occurrence of the event or conversion from one disease state to another, i.e., from a primary tumor to a metastatic tumor or to one at risk of developing a metastatic, or from at risk of a primary metastatic event to a secondary metastatic event or from at risk of a developing a primary tumor of one type to developing a one or more primary tumors of a different type. Risk evaluation can also comprise prediction of future clinical parameters, traditional laboratory risk factor values, or other indices of cancer, either in absolute or relative terms in reference to a previously measured population.

An "increased risk" is meant to describe an increased probably that an individual who carries a SNP within a let-7 family miRNA binding site, particularly the LCS6 SNP, will develop at least one of a variety of disorders, such as cancer, compared to an individual who does not carry a SNP within a let-7 family miRNA binding site. In certain embodiments, a LCS6 SNP carrier is 1.5×, 2×, 2.5×, 3×, 3.5×, 4×, 4.5×, 5×, 5.5×, 6×, 6.5×, 7×, 7.5×, 8×, 8.5×, 9×, 9.5×, 10×, 20×, 30×, 40×, 50×, 60×, 70×, 80×, 90×, or 100× more likely to develop at least one type of cancer than an individual who does not carry the LCS6 SNP. Moreover, an increased risk is meant to describe an increased susceptibility to developing at least one of a variety of disorders. In a specific embodiment, individuals who carry the LCS6 SNP are more susceptible to the deleterious effects of smoking and develop smoking-induced non-small cell lung cancer (NSCLC) earlier and more frequently than smokers who do not carry the LCS6 SNP. In certain embodiments, LCS6 SNP carriers who smoke develop at least one type of cancer 1, 2, 5, 7, 10, 12, 15, 17, 20, 22, 25, 27, or 30 years prior to the average age that a smoker who does not carry the LCS6 SNP develops at least one type of cancer. In other embodiments, a LCS6 SNP carrier who smokes is 1.5×, 2×, 2.5×, 3×, 3.5×, 4×, 4.5×, 5×, 5.5×, 6×, 6.5×, 7×, 7.5×, 8×, 8.5×, 9×, 9.5×, 10×, 20×, 30×, 40×, 50×, 60×, 70×, 80×, 90×, or 100× more likely to develop at least one type of cancer than a smoking individual who does not carry the LCS6 SNP. Moreover, carriers of the LCS6 SNP who have developed one cancer are more likely to develop secondary cancers. In certain embodiments, LCS6 SNP carriers who smoke develop at least one secondary cancer 1, 2, 5, 7, 10, 12, 15, 17, 20, 22, 25, 27, or 30 years prior to the average age that a smoker who does not carry the LCS6 SNP develops at least one secondary cancer.

By poor prognosis is meant that the probability of the individual surviving the development of particularly aggressive or high-risk subtypes of cancer is less than the probability of surviving more benign forms. Poor prognosis is also meant to describe a less satisfactory recovery, longer recovery period, more invasive or high-risk therapeutic regime, or an increased probability of reoccurrence of the cancer. It has been shown that the LCS6 SNP is predicative of the occurrence of aggressive subtypes of cancer. These aggressive subtypes of cancers are associated with the worst prognosis of each of these cancer resulting in a poor prognosis.

"Predicting the onset" is meant to describe a method of detecting the presence of a SNP within an miRNA binding site that not only predicts the development of a disorder, but also correlates with an earlier presentation of that disorder. In a preferred embodiment, the disorder that develops as a result of the SNP is cancer. For example, it has been shown that cancer patients who carry the LCS6 SNP are younger, on average, than other cancer patients. As such, individuals who carry the LCS6 SNP will experience the onset of particular types of cancer including, but not limited to, all varieties of lung cancer (NSCLC and small cell lung cancer), ovarian cancer, breast cancer, uterine cancer, head and neck cancer, pancreatic cancer, and colon cancer at an earlier age. In certain embodiments, the presence of the LCS6 SNP, predicts that presentation of at least one type of cancer 1, 2, 5, 7, 10, 12, 15, 17, 20, 22, 25, 27, or 30 years prior to the average age that an individual who does not carry the LCS6 SNP develops at least one type of cancer. In other embodiments, the identification of a SNP within an miRNA binding site of the invention, predicts that presentation of at least one disorder 1, 2, 5, 7, 10, 12, 15, 17, 20, 22, 25, 27, or 30 years prior to the average age that an individual who does not carry the same SNP develops this same disorder.

Cell proliferative disorders include a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue.

Cancers include, but are not limited to, acute lymphoblastic leukemia, acute myeloid leukemia, adrenocortical carcinoma, adrenocortical carcinoma, AIDS-related cancers, AIDS-related lymphoma, anal cancer, appendix cancer, childhood cerebellar astrocytoma, childhood cerebral astrocytoma, basal cell carcinoma, skin cancer (non-melanoma), extrahepatic bile euct cancer, bladder cancer, bone cancer, osteosarcoma and malignant fibrous histiocytoma, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, mycosis fungoides, Sézary Syndrome, endometrial cancer, esophageal cancer, extracranial germ cell tumor, extragonadal germ cell tumor, extrahepatic bile duct cancer, eye cancer, tntraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, islet cell tumors (endocrine pancreas), Kaposi Sarcoma, kidney (renal cell) cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, non-small cell lung cancer, small cell lung cancer, AIDS-related lymphoma, non-Hodgkin lymphoma, primary central nervous system lymphoma, Waldenström macroglobulinemia, medulloblastoma, melanoma, intraocular (eye) melanoma, merkel cell carcinoma, mesothelioma malignant, mesothelioma, metastatic squamous neck cancer, mouth cancer, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, tterine sarcoma, skin cancer (nonmelanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular Cancer, throat Cancer, thymoma, thymoma and thymic carcinoma, thyroid cancer, transitional cell cancer of the renal pelvis and ureter, gestational trophoblastic tumor, urethral cancer, endometrial uterine cancer, uterine sarcoma, vaginal cancer, vulvar cancer, and Wilms Tumor.

A subject is preferably a mammal. The mammal can be a human, non-human primate, mouse, rat, dog, cat, horse, or cow, but are not limited to these examples. Mammals other than humans can be advantageously used as subjects that represent animal models of a particular disease. A subject can be male or female. A subject can be one who has been previously diagnosed or identified as having a disease and optionally has already undergone, or is undergoing, a therapeutic intervention for the disease. Alternatively, a subject can also be one who has not been previously diagnosed as having the disease. For example, a subject can be one who exhibits one or more risk factors for a disease.

The biological sample can be any tissue or fluid that contains nucleic acids. Various embodiments include paraffin imbedded tissue, frozen tissue, surgical fine needle aspirations, cells of the skin, muscle, lung, head and neck, esophagus, kidney, pancreas, mouth, throat, pharynx, larynx, esophagus, facia, brain, prostate, breast, endometrium, small intestine, blood cells, liver, testes, ovaries, uterus, cervix, colon, stomach, spleen, lymph node, bone marrow or kidney. Other embodiments include fluid samples such as bronchial brushes, bronchial washes, bronchial ravages, peripheral blood lymphocytes, lymph fluid, ascites, serous fluid, pleural effusion, sputum, cerebrospinal fluid, lacrimal fluid, esophageal washes, and stool or urinary specimens such as bladder washing and urine.

Linkage disequilibrium (LD) refers to the co-inheritance of alleles (e.g., alternative nucleotides) at two or more different SNP sites at frequencies greater than would be expected from the separate frequencies of occurrence of each allele in a given population. The expected frequency of co-occurrence of two alleles that are inherited independently is the frequency of the first allele multiplied by the frequency of the second allele. Alleles that co-occur at expected frequencies are said to be in "linkage equilibrium". In contrast, LD refers to any non-random genetic association between allele(s) at two or more different SNP sites, which is generally due to the physical proximity of the two loci along a chromosome. LD can occur when two or more SNPs sites are in close physical proximity to each other on a given chromosome and therefore alleles at these SNP sites will tend to remain unseparated for multiple generations with the consequence that a particular nucleotide (allele) at one SNP site will show a non-random association with a particular nucleotide (allele) at a different SNP site located nearby. Hence, genotyping one of the SNP sites will give almost the same information as genotyping the other SNP site that is in LD.

For screening individuals for genetic disorders (e.g. prognostic or risk) purposes, if a particular SNP site is found to be useful for screening a disorder, then the skilled artisan would recognize that other SNP sites which are in LD with this SNP site would also be useful for screening the condition. Various degrees of LD can be encountered between two or more SNPs with the result being that some SNPs are more closely associated (i.e., in stronger LD) than others. Furthermore, the physical distance over which LD extends along a chromosome differs between different regions of the genome, and therefore the degree of physical separation between two or more SNP sites necessary for LD to occur can differ between different regions of the genome.

For screening applications, polymorphisms (e.g., SNPs and/or haplotypes) that are not the actual disease-causing (causative) polymorphisms, but are in LD with such causative polymorphisms, are also useful. In such instances, the genotype of the polymorphism(s) that is/are in LD with the causative polymorphism is predictive of the genotype of the causative polymorphism and, consequently, predictive of the phenotype (e.g., disease) that is influenced by the causative SNP(s). Thus, polymorphic markers that are in LD with causative polymorphisms are useful as markers, and are particularly useful when the actual causative polymorphism(s) is/are unknown.

Linkage disequilibrium in the human genome is reviewed in: Wall et al., "Haplotype blocks and linkage disequilibrium in the human genome", Nat Rev Genet. 2003 August; 4(8): 587-97; Gamer et al., "On selecting markers for association studies: patterns of linkage disequilibrium between two and three diallelic loci", Genet Epidemiol. 2003 January; 24(1): 57-67; Ardlie et al., "Patterns of linkage disequilibrium in the human genome", Nat Rev Genet. 2002 April; 3(4):299-309 (erratum in Nat Rev Genet 2002 July; 3(7):566); and Remm et al., "High-density genotyping and linkage disequilibrium in the human genome using chromosome 22 as a model"; Curr Opin Chem Biol. 2002 February; 6(1):24-30.

The contribution or association of particular SNPs and/or SNP haplotypes with disease phenotypes, such as cancer, enables the SNPs of the present invention to be used to develop superior tests capable of identifying individuals who express a detectable trait, such as cancer, as the result of a specific genotype, or individuals whose genotype places them at an increased or decreased risk of developing a detectable trait at a subsequent time as compared to individuals who do not have that genotype. As described herein, screening may be based on a single SNP or a group of SNPs. To increase the accuracy of predisposition/risk screening, analysis of the SNPs of the present invention can be combined with that of other polymorphisms or other risk factors of the disease, such as disease symptoms, pathological characteristics, family history, diet, environmental factors or lifestyle factors.

The screening techniques of the present invention may employ a variety of methodologies to determine whether a test subject has a SNP or a SNP pattern associated with an increased or decreased risk of developing a detectable trait or whether the individual suffers from a detectable trait as a result of a particular polymorphism/mutation, including, for example, methods which enable the analysis of individual chromosomes for haplotyping, family studies, single sperm DNA analysis, or somatic hybrids. The trait analyzed using the diagnostics of the invention may be any detectable trait that is commonly observed in pathologies and disorders.

EXAMPLES

Example 1

General Methods

Study Populations

Lung tissue samples from patients with a diagnosis of NSCLC were collected following Yale University Human Investigation Committee approval. Cases were chosen based on the availability of frozen stored tissue from lung tumor resections from 1994 through 2003, and from recent cases with extra tissue available. Tissue was collected from 87 patients. Seven patients were excluded due to other risk factors for lung cancer (e.g., immunosuppression, tuberculosis) and six were excluded due to their tumors being non-lung primary metastatic disease. Seventy-four patients were included in the analysis (Table 2).

TABLE 2

Table 2. Yale NSCLC patient characteristics. Proportion male (M) (51.3%) and female (F) (48.6%), proportion Caucasian (85.1%), African American (AA)(8.1%), Hispanic (2.7%) and Asian (4.1%). For patients with multiple simultaneously diagnosed lung cancers both cancer types are listed. The presence or absence of the SNP is denoted as Yes (Y) or No (N).

| Patient | Sex | Population | Age | Pack-Year | Cancer Type | LCS6 SNP |
|---|---|---|---|---|---|---|
| 1 | F | Caucasian | 64 | 150 | Adenocarcinoma | N |
| 2 | M | Caucasian | 73 | 20 | Adenosquamous | N |
| 3 | M | Caucasian | 64 | 50 | Large cell | N |
| 4 | F | Caucasian | 76 | unknown | Adenocarcinoma | N |
| 5 | M | Hispanic | 54 | 70 | Squamous cell | N |
| 6 | M | Caucasian | 64 | 10 | Squamous cell | Y |
| 7 | M | Caucasian | 86 | 60 | Squamous cell | N |
| 8 | F | Caucasian | 54 | 0 | Adenocarcinoma | N |
| 9 | F | Caucasian | 58 | 40 | Adenosquamous | N |
| 10 | F | Caucasian | 65 | 150 | Adenocarcinoma | N |
| 11 | M | Caucasian | 64 | 17 | Adenocarcinoma | Y |
| 12 | F | Hispanic | 65 | 20 | Adenocarcinoma | N |
| 13 | F | Caucasian | 89 | unknown | Adenocarcinoma | N |
| 14 | F | Caucasian | 47 | 0 | Large cell | N |
| 15 | M | Caucasian | 48 | 45 | Squamous cell | Y |
| 16 | M | Caucasian | 85 | 70 | Adenocarcinoma | N |
| 17 | M | Caucasian | 86 | 75 | Adenosquamous | N |
| 18 | F | Caucasian | 49 | 15 | Squamous cell, Adenocarcinoma | Y |
| 19 | M | Asian | 55 | 40 | Squamous cell | N |
| 20 | F | Caucasian | 74 | 0 | Adenocarcinoma | N |
| 21 | F | Caucasian | 58 | 2 | Adenocarcinoma | Y |
| 22 | F | AA | 40 | 20 | Adenocarcinoma | N |
| 23 | F | Caucasian | 52 | 30 | Adenocarcinoma, BAC | N |
| 24 | M | Caucasian | 50 | 40 | Large cell | N |
| 25 | M | Caucasian | 69 | 105 | Adenocarcinoma | N |
| 26 | F | Caucasian | 75 | 50 | Adenocarcinoma | N |
| 27 | M | Caucasian | 83 | 60 | Large cell | N |
| 28 | M | Caucasian | 42 | 20 | Adenocarcinoma | Y |
| 29 | F | Caucasian | 52 | 35 | Adenocarcinoma | N |
| 30 | M | Caucasian | 71 | 70 | Adenocarcinoma, Squamous cell | N |
| 31 | F | AA | 69 | 50 | Adenocarcinoma | N |
| 32 | M | Caucasian | 44 | 50 | Adenocarcinoma | N |
| 33 | F | Caucasian | 66 | $2^{nd}$ hand | Adenocarcinoma | Y |
| 34 | F | Caucasian | 73 | 75 | Adenocarcinoma | N |
| 35 | M | AA | 72 | 30 | Adenocarcinoma | N |
| 36 | F | Caucasian | 72 | 120 | Squamous cell | Y |
| 37 | F | Caucasian | 62 | 50 | Adenocarcinoma | N |

TABLE 2-continued

Table 2. Yale NSCLC patient characteristics. Proportion male (M) (51.3%) and female (F) (48.6%), proportion Caucasian (85.1%), African American (AA)(8.1%), Hispanic (2.7%) and Asian (4.1%). For patients with multiple simultaneously diagnosed lung cancers both cancer types are listed. The presence or absence of the SNP is denoted as Yes (Y) or No (N).

| Patient | Sex | Population | Age | Pack-Year | Cancer Type | LCS6 SNP |
|---|---|---|---|---|---|---|
| 38 | M | Caucasian | 74 | unknown | Adenocarcinoma | N |
| 39 | M | Caucasian | 78 | 20 | Adenocarcinoma | N |
| 40 | M | Caucasian | 68 | 32 | Adenocarcinoma | N |
| 41 | M | Caucasian | 66 | 40 | Adenosquamous | N |
| 42 | M | Caucasian | 88 | 40 | Squamous cell | Y |
| 43 | F | Caucasian | 63 | 60 | Adenocarcinoma | N |
| 44 | F | AA | 69 | 0 | Adenocarcinoma | N |
| 45 | M | Caucasian | 60 | 17 | Squamous cell | Y |
| 46 | F | AA | 49 | 50 | Adenocarcinoma | N |
| 47 | F | Caucasian | 65 | 60 | Adenosquamous | N |
| 48 | M | Caucasian | 63 | 45 | Adenocarcinoma | N |
| 49 | F | Asian | 67 | 0 | Adenocarcinoma | N |
| 50 | M | Caucasian | 60 | 100 | Adenocarcinoma | Y |
| 51 | M | Caucasian | 65 | 125 | Carcinoma | N |
| 52 | M | Caucasian | 52 | 80 | Squamous cell | N |
| 53 | M | Caucasian | 62 | 90 | Squamous cell | N |
| 54 | F | Caucasian | 69 | 140 | Large cell | N |
| 55 | F | Caucasian | 61 | 40 | Squamous cell | N |
| 56 | F | Caucasian | 80 | 15 | Squamous cell | N |
| 57 | M | Caucasian | 73 | 60 | Squamous cell | Y |
| 58 | F | Caucasian | 57 | 120 | Adenocarcinoma | N |
| 59 | F | Caucasian | 56 | 15 | Adenocarcinoma | N |
| 60 | M | Caucasian | 43 | 40 | Adenocarcinoma | Y |
| 61 | F | Asian | 47 | 10 | Adenocarcinoma | N |
| 62 | F | Caucasian | 39 | $2^{nd}$ hand | BAC | N |
| 63 | M | Caucasian | 76 | 55 | Adenocarcinoma | N |
| 64 | F | Caucasian | 43 | 33 | Adenocarcinoma | Y |
| 65 | F | Caucasian | 50 | 30 | Squamous cell | N |
| 66 | M | Caucasian | 70 | 100 | Squamous cell, Adenocarcinoma | N |
| 67 | M | Caucasian | 70 | 56 | Squamous cell | N |
| 68 | F | Caucasian | 73 | 94 | Adenocarcinoma | N |
| 69 | F | AA | 62 | 40 | Adenocarcinoma | N |
| 70 | M | Caucasian | 58 | 80 | Adenocarcinoma | N |
| 71 | M | Caucasian | 71 | 55 | Adenocarcinoma | N |
| 72 | M | Caucasian | 78 | 90 | Squamous cell | N |
| 73 | M | Caucasian | 72 | 45 | Squamous cell | N |
| 74 | M | Caucasian | 65 | 65 | Squamous cell, Adenosquamous | Y |

To determine the frequency of the SNP alleles, 2433 individuals were typed from a global sample of 46 populations. According to population ancestry and geographic locations, these 46 populations are categorized into 4 groups: European (including West Asia), African, Asian (including the Pacific) and Native American. Sample descriptions and samples sizes can be found in the ALlele FREquency Database (ALFRED) (Cheung, K. et al. Nucleic Acids Res 2000; 28:361-3) by searching for the population names (alfred.med.yale.edu). DNA samples were extracted from lymphoblastoid cell lines that have been established and/or grown in the Yale University laboratory of K.K.K. The methods of transformation, cell culture, and DNA purification have previously been described (Anderson, M. and G, J. F. In Vitro 1984; 20: 856-8). All volunteers were apparently normal and otherwise healthy adult males or females and samples were collected after receipt of appropriate informed consent.

Lung cancer cases (n=325) for the New Mexico case-control study were recruited from Albuquerque through two local hospitals, the Veterans hospital and the University of New Mexico (UNM) hospital. All stages and histological types of lung cancer were included. Controls (n=325) with no history of any prior cancer were recruited from two ongoing local smoker cohorts, the Veterans Smokers Cohort (mainly veterans from Albuquerque) and the Lovelace Smokers Cohort (general residents in Albuquerque). Those two cohorts started to recruit participants in 2001 to conduct longitudinal studies on molecular markers of respiratory carcinogenesis in biological fluids such as sputum from people at risk for lung cancer. Enrollment of lung cancer patients from these populations began in 2004. A standardized questionnaire was used to collect information on medical, family, and smoking exposure history, and quality of life for both lung cancer cases and control cohort members. Controls were randomly matched to lung cancer cases after categorization into different age groups (5-year differences) by sex and cohort (Table 3). Cases with small cell lung cancer were excluded to more precisely assess the effect of the LCS6 SNP on risk for NSCLC. Cases over 82 years old (the maximum age in the control group), cases with any prior cancer history, never smokers or cases with missing data on smoking-related covariates were also excluded in the data analysis, resulting in 218 cases included in the analysis.

TABLE 3

Table 3. Demographic New Mexico Lung Cancer Case-Control Data. Cases indicate patients with lung cancer and controls are non-cancerous patients.

| Variables | Controls | Cases | P-value |
|---|---|---|---|
| N | 325 | 218 | |
| Age | 64.6 ± 9.0 | 65.1 ± 9.0 | $0.72^a$ |
| Sex (male, %) | 68.9 | 73.9 | $0.22^b$ |
| Ethnicity (%) | | | $0.01^b$ |
| White | 67.4 | 75.7 | |
| Hispanic | 24.9 | 14.7 | |
| Others | 7.7 | 9.6 | |
| Current smoking status (current smoker, %) | 32.9 | 37.2 | $0.31^b$ |
| Pack-years | 41.4 ± 28.5 | 56.9 ± 32.4 | $<0.0001^c$ |
| Family history of cancer (yes, %) | 44.6 | 59.4 | $0.0006^b$ |
| Histology (%) | | | |
| Adenocarcinoma | | 45.9 | |
| Squamous cell carcinoma | | 24.8 | |
| Others$^d$ | | 29.4 | |

$^a$Two-sided two-sample t-test between cases and controls.
$^b$2 test for differences between cases and controls.
$^c$Two-sided Wilcoxon rank sum test between cases and controls.
$^d$Others included large cell lung cancer, poorly differentiated and other non-small cell lung cancer.

The Boston study population was derived from a large ongoing molecular epidemiological study that began in 1992 and now has more than 2205 NSCLC patients recruited at MGH. Details of this case-control population have been described previously (Zhai, R. et al. Clin Cancer Res 2008; 14:612-7; Su, L. et al. Carcinogenesis 2006; 27:1024-9; and Zhou, W. et al. Cancer Research 2002; 62: 1377-81). This study was approved by the Human Subjects Committees of Massachusetts General Hospital (MGH) and Harvard School of Public Health, Boston, Mass. Briefly, all histologically confirmed, newly diagnosed patients with NSCLC at MGH were recruited between December 1992 and February 2006. Before 1997, only early stage (stage I and II) patients were recruited. After 1997, all stages of NSCLC cases were recruited in this study. Controls were recruited at MGH from healthy friends and non-blood-related family members (usually spouses) of several groups of hospital patients: (a) patients with cancer, whether related or not related to a case; or (b) patients with a cardiothoracic condition undergoing surgery. No matching was performed. Importantly, none of the controls were themselves patients. Potential controls who carried a previous diagnosis of any cancer (other than non-melanoma skin cancer) were excluded from participation. Over 85% eligible cases and over 90% controls participated in this study and provided blood samples. A research nurse administered questionnaires on demographic information and a detailed smoking history of each participant. To reduce potential variation in allele frequency by ethnicity, only Caucasians were considered in the analysis. Detailed demographics of the participants of this case control are in Table 4.

Evaluation of 3'UTR Sequences and the LCS6 SNP

DNA was isolated from fresh-frozen and formalin-fixed paraffin-embedded (FFPE) lung tumors and non-cancerous lungs, and non-primary lung tumors using the DNeasy Blood and Tissue Kit (Qiagen). The tissue samples were acquired through the Yale-New Haven Hospital Pathology Department after HIC approval. Segments of the KRAS 3'UTR were amplified using PfuTurbo DNA polymerase (Stratagene) and DNA primers (Table 5). PCR products were purified using the

TABLE 4

Supplementary Table 3B. Demographic characteristics among Boston NSCLC cases and controls
Table 4. Demographic characteristics among Boston NSCLC cases and controls.

| Characteristics | Overall | | | Male | | | Female | |
|---|---|---|---|---|---|---|---|---|
| | Cases (n = 2205) | Controls (n = 1497) | p | Cases (n = 1118) | Controls (n = 665) | p | Cases (n = 1087) | Controls (n = 832) |
| Age (mean ± SD) | 64.9 ± 10.7 | 58.2 ± 12.1 | <0.01 | 65.8 ± 10.5 | 60.2 ± 12.8 | <0.01 | 64.8 ± 11.0 | 58.8 ± 11.4 |
| Gender, N (%) | | | | | | | | |
| Female | 1087 (49.3%) | 822 (55.6%) | <0.01 | | | | | |
| Male | 1118 (50.7%) | 665 (44.4%) | | | | | | |
| Smoking, N (%) | | | | | | | | |
| Never | 204 (9.3%) | 522 (34.9%) | <0.01 | 77 (6.8%) | 206 (30.8%) | <0.01 | 128 (11.7%) | 324 (38.5%) |
| Ex-smoker | 1174 (53.2%) | 688 (46.9%) | | 649 (57.6%) | 362 (53.8%) | | 535 (48.8%) | 333 (39.7%) |
| Curent smoker | 827 (37.5%) | 287 (19.2%) | | 401 (35.6%) | 105 (15.6%) | | 434 (39.6%) | 183 (21.8%0) |
| Years since quit (median)[a,b] | 12 (1-99) | 18 (1-65) | <0.01 | 14 (1-59) | 20 (1-65) | <0.01 | 12 (1-55) | 17 (1-99) |
| Pack-years[b] | 50 (0.1-231) | 25 (0.1-218) | <0.01 | 58 (0.2-231) | 29 (0.1-210) | <0.01 | 44 (0.02-210) | 21 (0.03-218) |
| Tumor stage (%) | | | | | | | | |
| I and II | 48.6% | | | 49.0% | | | 48.0% | |
| III and IV | 51.3% | | | 51.0% | | | 52.0% | |
| Cell type (%) | | | | | | | | |
| Adenocarcinoma | 57.0% | | | 50.6% | | | 63.4% | |
| Squamous cell carcinoma | 21.9% | | | 28.1% | | | 15.6% | |
| Others | 21.1% | | | 21.3% | | | 21.0% | |
| Kraslet7 genotype | | | | | | | | |
| TT | 1885 (81.9%) | 1248 (83.4%) | 0.32 | 944 (84.4%) | 549 (82.6%) | 0.46 | 861 (79.2%) | 699 (84.0%) |
| TG | 378 (17.4%) | 231 (15.4%) | | 161 (14.4%) | 105 (19.8%) | | 217 (20.0%) | 126 (15.1%) |
| GG | 22 (1.0%) | 18 (1.2%) | | 13 (1.2%) | 11 (1.7%) | | 9 (0.8%) | 7 (0.8%) |
| TG + GG | 400 (18.3%) | 249 (16.6) | 0.25* | 174 (15.6%) | 116 (17.4%) | 0.32* | 226 (20.6%) | 133 (15.8%)[c] |

[a]Ex-smokers only;
[b]Median (range), tested by non-parametric Wilcoxon's rank sum test;
[c]Continuous variables tested with the Student categorical variables tested using the $1^2$ test.
*Compared with TT genotype, Fisher's exact test.

QIAquick PCR Purification Kit or 96 PCR Purification Kit (Qiagen) and sequenced using the same primers. The NRAS 3'UTR was sequenced in the same manner

TABLE 5

Table 5. Primer Sequences Used in the Study.

| | Primer | Sequence (5'-3') | |
|---|---|---|---|
| For sequencing the KRAS 3'UTR | SMJ104 | CTAGCTAGCATACAATTTGTACTTTTTTCTTAAGGCATAC | (SEQ ID NO: 29) |
| | LJC1 | GGCACACCACCACCCCAAAATCTC | (SEQ ID NO: 30) |
| | LJC2 | CCATCTTCAGTGCCAGTCTTGGG | (SEQ ID NO: 31) |
| | LJC3 | GGGTCGTATACCAAAGGCCTTAG | (SEQ ID NO: 32) |
| | LJC4 | GCCTGAACTAGTTCACAGACAAGGG | (SEQ ID NO: 33) |
| | LJC5 | CTAGCTAGCTCAATGCAGAATTCATGCTATCCAG | (SEQ ID NO: 34) |
| For sequencing only LCS6 and RFLP analysis | LJC21 | GGTGTCAGAGTCTCGCTCTT | (SEQ ID NO: 35) |
| | LJC3 | GGGTCGTATACCAAAGGCCTTAG | (SEQ ID NO: 36) |
| | LJC27* | CCTGAGTAGCTGGGATTACA | (SEQ ID NO: 37) |
| | LJC28* | GGATACCATATACCCAGTGCCTT | (SEQ ID NO: 38) |

TABLE 5-continued

Table 5. Primer Sequences Used in the Study.

| | Primer | Sequence (5'-3') | |
|---|---|---|---|
| For sequencing the NRAS 3'UTR | LJC13 | CCACTTTCAAGCTGCACTGACAC | (SEQ ID NO: 39) |
| | LJC8 | CTAGCTGGAGTTACTGGTGCAATGAGC | (SEQ ID NO: 40) |
| | LJC9 | GATACCTATGAGGATTTGGAGGC | (SEQ ID NO: 41) |
| | LJC10 | GCATGGTAGCCTTCAGACAGAAC | (SEQ ID NO: 42) |
| | LJC11 | CTGCTTCTTGTAATTCATCTCTGC | (SEQ ID NO: 43) |
| | LJC12 | CAACTTAAAATATCGGCCCTTCC | (SEQ ID NO: 44) |
| For making KRAS wild-type | SMJ104 | CTAGCTAGCATACAATTTGTACTTTTTTCTTAAGGCATAC | (SEQ ID NO: 29) |
| | LJC5 | CTAGCTAGCTCAATGCAGAATTCATGCTATCCAG | (SEQ ID NO: 34) |
| For making KRAS mLCS6 | LJC16 | CGAACTCCTGACCTCAAGTGATgCACCCACCTT | (SEQ ID NO: 45) |
| | LJC17 | ATCACTTGAGGTCAGGAGTTCGAGACCAGCCT | (SEQ ID NO: 46) |

* = used for nested PCR

Restriction Fragment Length Polymorphism (RFLP) Analysis

DNA isolated for sequencing was amplified using Pfu-Turbo DNA polymerase (Stratagene) and primers listed in Table 5. The PCR product was then digested with Hin fI and analyzed on agarose gels.

TaqMan Assay

For high-throughput genotyping, the DNA isolated from lymphocytes, blood, or tumor samples was amplified using TaqMan PCR assays designed specifically to identify the LSC6 SNP (Applied Biosciences). Data was analyzed using standard software on the real-time PCR machine used for each study.

Statistical Analysis

All statistical analyses were performed using the SAS statistical software (SAS Institute, Cary, N.C.) and a chi-square test was used to test for departures from Hardy-Weinberg equilibrium (HWE) for the variant allele in the Yale study population. To calculate significance a Chi-Square test was used for categorical variables, a t-test was used for continuous variables and in some cases a two-sided Fisher's exact test was used. For the case-control association studies, to compare controls and cases, two-sided two-sample t-tests, Chi-Square analyses and two-sided Wilcoxon rank-sum tests were performed, as appropriate. For evaluating the association between the KRAS LCS6 allele and risk for NSCLC in light or heavy smokers, age, race, sex, smoking status, pack-years of smoking and years since smoking cessation (if ex-smokers) were adjusted with an unconditional logistic regression model. To test the association with the allele and the pack-year interaction for NSCLC, a likelihood ratio test was used. The median pack year was used as the evaluation point for the gene-environment interaction in both studies. The variant homozygotes were few and pooled with the heterozygotes for these analyses and are referred to collectively as those "with the variant."

Methods of Detecting SNPs

The invention encompasses methods of detecting the LCS6 SNP including, but not limited to, polymerase chain reaction (PCR) using either the primers disclosed herein (SEQ ID NOs: 22-39) or with any primer that amplifies any portion of the 3'UTR of a RAS family gene or mRNA transcript comprising the LCS6 SNP, nucleic acid/probe hybridization (for example, all forms of DNA and RNA are contemplated as probes), probe hybridization (for example, in vitro assays, in situ hybridization, Northern and/or Southern blots), sequencing, RFLP analysis, functional assays (for example, introduction of a test polynucleotide into a cell in vivo or in vitro and examination of resulting cell proliferation, cell death, cell metastasis, change of morphology, degredation of extracellular matrix, protein expression, reporter protein/marker expression), miRNA-binding assays (for example, in vitro or in vivo assays to determine ability of miRNAs of bind, silence, degrade, or inhibit the translation of the test polynucleotide), translational assays (for example, expression of polypeptides encoded for by test polynucleotides, expression of reporter polypeptides or detectable markers/labels linked to the test polynucleotide, Western blot analysis to determine translation of the test polynucleotide), and all other art-recognized methods.

Probes used to identify or detect the LCS6 SNP are polynucleic acids, either DNA or RNA, and correspond to either the entire 3'UTR of KRAS, or any fragment thereof. The term "fragment", as used herein, is meant to describe a polynucleotide that is 100% identical to the polynucleotide from which it is derived over a span that is less than the entire length of the polynucleotide from which it is derived. Encompassed probes comprise SEQ ID NO: 15, e.g., wild type LCS6, or SEQ ID NO: 21, e.g. the LCS6 SNP. Probes used to detect the LCS6 SNP comprise the sequences of SEQ ID NOs: 15 or 21, as well as any sequences complementary to SEQ ID NOs: 15 or 21. Contemplated probles also include wild type and/or modified miRNA sequences, and fragments thereof.

Luciferase Reporters and Transient Transfections

The luciferase reporter with an altered LCS6 KRAS 3'UTR corresponding to the LCS6 variant (pGL3-KRASm6) was constructed through site-directed mutagenesis of pGL3-KRAS (Johnson, S. M. et al. Cell 2005; 120(5): 635-47) using GeneTailor (Invitrogen) (Table 5). HeLa S3 and CRL-2741 cells were grown in DMEM with 10% FBS or Keratinocyte-SFM, both with penicillin/streptomycin (Invitrogen). Cells were transiently transfected with 700 ng pGL3-KRAS, pGL3-KRASm6, or pGL3-Control (Promega) and 70 ng pRL-TK (Promega) using Lipofectamine 2000 (Invitrogen) for 24 hours. Reporter expression was analyzed with the Dual-Luciferase Reporter Assay (Promega) and Wallac Victor 1420 (PerkinElmer) (Chen, K. et al. Nature Genetics 2006; 38). Two-tailed t-tests were done to verify statistical significance of differences in luciferase expression using GraphPad Prism.

Example 2

Identification of a Candidate let-7 SNP let-7 complementary sites (LCSs) were sequenced in the KRAS 3' untranslated region (UTR) from 74 non-small cell lung cancer (NSCLC) cases to identify mutations and single nucleotide polymorphisms (SNPs) that correlated with NSCLC. A candidate SNP was identified and the allele frequency was determined by typing the polymorphism in 2433 people (representing 46 human populations). The association was further assessed between the SNP and the risk of smoking-induced NSCLC in two independent case-control studies.

The novel SNP was identified in an LCS in 24% of Caucasian NSCLC patients, compared to 7.4% of the general Caucasian population. The presence of the SNP predicted for squamous cell carcinoma versus adenocarcinoma and a positive family history of cancer. The variant allele at the SNP is associated with earlier onset NSCLC (< versus >50 years of age) and additional cancer diagnoses. The frequency of the variant is 20.3% in our cohort of NSCLC patients and 5.8% in world populations. Both independent case-control studies found that smokers with the variant and <40 or 41 pack-year smoking histories had an elevated risk of developing NSCLC compared to smokers without the variant (ORs=1.36-2.3, 95% CI=1.07-1.73, p=0.01 and 1.1-4.6, p=0.02). Functionally, the variant allele leads to increased let-7 binding and KRAS suppression in vitro.

A variant allele in a KRAS miRNA complementary site is significantly associated with increased smoking-induced NSCLC risk. These findings represent a new paradigm for miRNAs in cancer susceptibility and are used to better direct lung cancer screening programs.

Example 3

Identification of a SNP in a let-7 Complementary Site in the KRAS 3'UTR

Figures 20A, 20B, 20C:
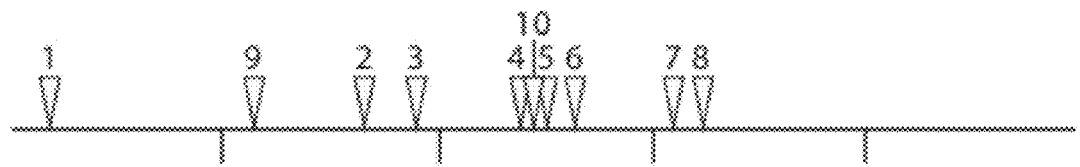
FIGS. 20A-D describes the prevalence of the LCS6 SNP in primary cancer tissue. (A) Location of the putative LCSs in the KRAS 3_UTR. LCS1-LCS8 had been previously identified.12 LCSs where mutations are found are shown in red. The KRAS 3_UTR is 5016 bp, and the markers are positioned every 1000 bp. (B) The sequence of LCS6 with either the reference allele (GAUUCACCCACCUUGGCCUCA (SEQ ID NO: 15)) or the variant allele (GAUGCACCCACCUUG-GCCUCA (SEQ ID NO: 21, SNP bolded). (C) The variant allele in LCS6 was seen in 20.3% of the primary lung tumors and was present in the adjacent tissue when available. (D) Representative sequencing traces from a tumor (T) and adjacent, non-cancerous (A) sample from a patient with the variant allele (18T and A) and a patient without the variant allele (7C). Solid arrows point to heterozygosity (T/G) at the fourth nucleotide of LCS6. The double arrow points to the homozygous T allele. (D-1) provides the following sequences from top to bottom: GATKCACCCACCTTGGCCTCA (SEQ ID NO: 90), gattcacccaccttggcctca (SEQ ID NO: 91), GATGCACCCACCTTGGCCTCA (SEQ ID NO: 92), GATGCACCCACCTTGGCCTCA (SEQ ID NO: 92), GATKCACCCACCTTGGCCTCA (SEQ ID NO: 90), gattcacccaccttggcctca (SEQ ID NO: 91), GATTCACCCACCTTGGCCTCA (SEQ ID NO: 93), and GATNCACCCACCTTGGCCTCA (SEQ ID NO: 94). (D-2) provides the following sequences from top to bottom: GATTCACCCACCTTGGCCTCA (SEQ ID NO: 93), gattcacccaccttggcctca (SEQ ID NO: 91), and GATTCACCCACCTTGGCCTCA (SEQ ID NO: 93).
Figures 1, 20D:
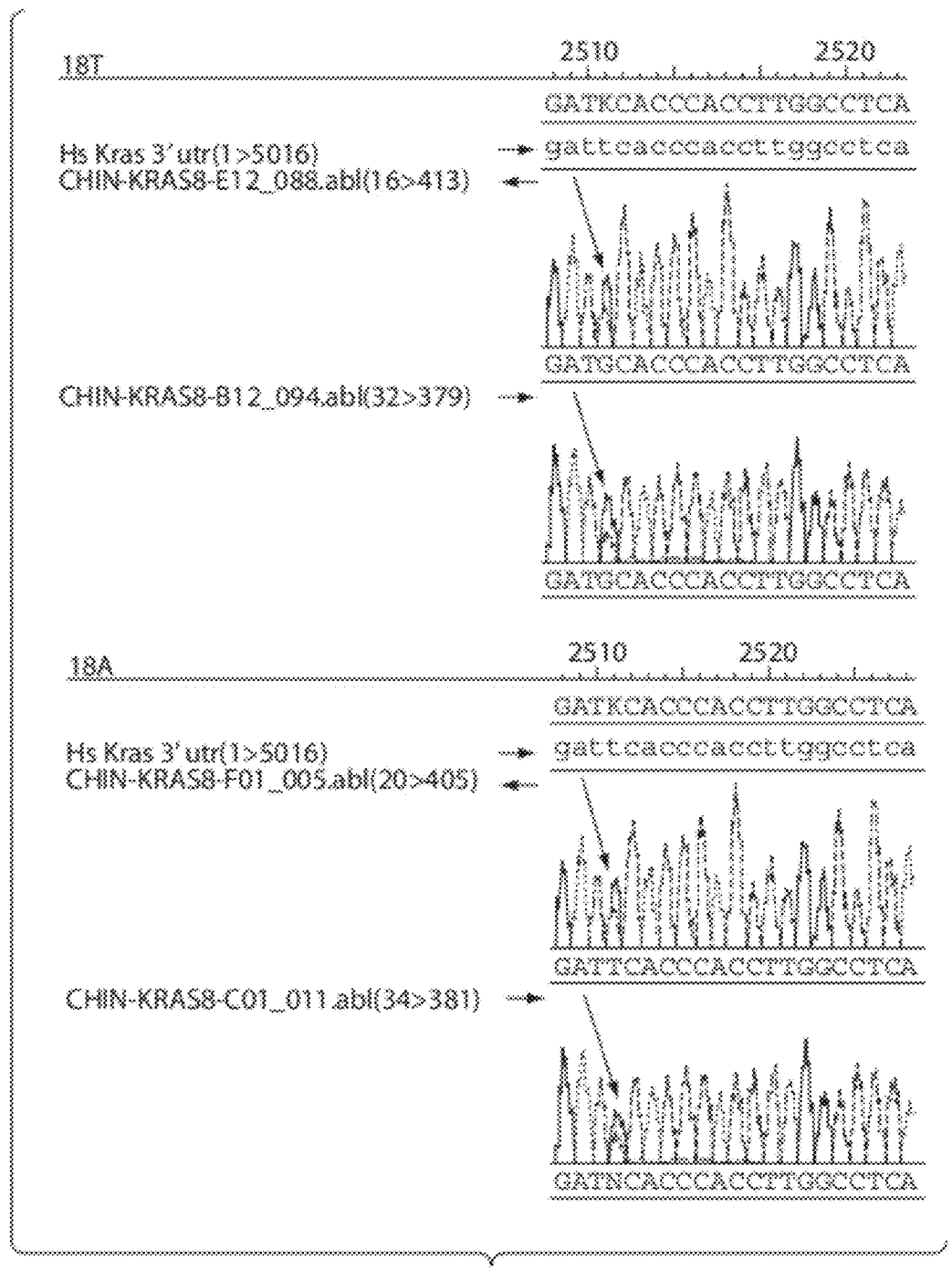
Figures 2, 20D:
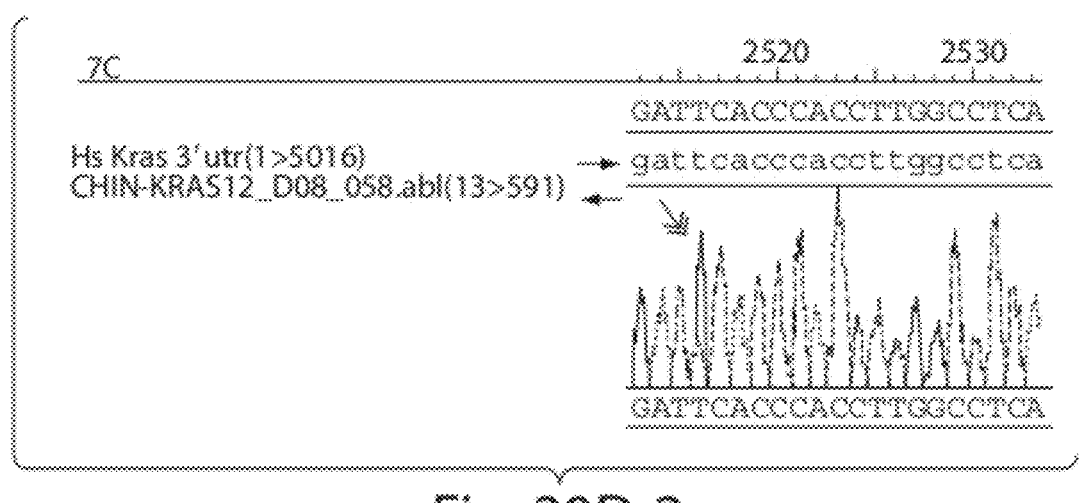
Figure 21:
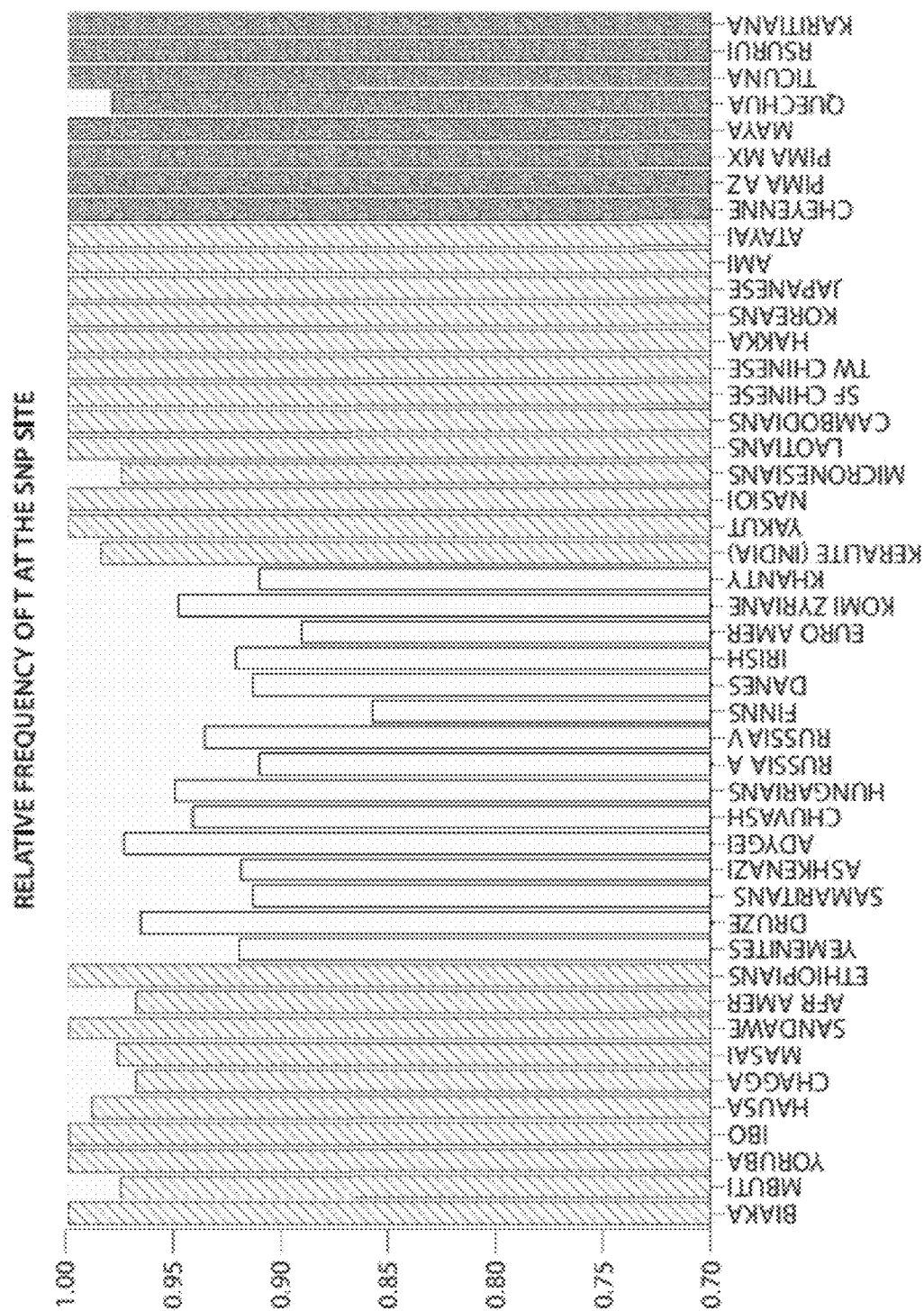
FIG. 21 demonstrates the frequency of the reference allele across the world. Frequency of the reference allele (T) at the SNP locus was examined in 2433 people. They represented 46 populations from around the world, which were categorized based on geography (from left to right): Africa (diagonal stripes), Europe, Southwest Asia and Western Siberia (white), South central Asia, East Asia and the Pacific (diagonal stripes), and the Americas (black dots). The frequency of the reference allele (T) across all populations is 97.1% and the frequency of the alternative allele (G) is 2.9%. The frequency of the G allele in African populations is 1.9%, in European populations is 7.6%, in Asian populations is 0.03%, and in Native American populations is 0.03%. The allele frequencies in the individual populations are in ALFRED.

RAS expression is regulated in a 3'UTR and let-7-dependent manner through ten putative let-7 complementary sites (LCSs) in the human KRAS 3'UTR (FIG. 23A) (Johnson, S. M. et al. Cell 2005; 120(5): 635-47). Based on data from the HapMap (Consortium TIH. Nature 2003; 426:789-96) and dbSNP (Sherry, S. et al. Genome Res 1999; 9:677-9) databases, only one SNP, rs712(−), is reported in an LCS. Tissue from seventy-four patients with NSCLC exhibited changes from the reference human sequence in at least one LCSs. Changes in LCS1, LCS9, and LCS4 (Table 7) did not appear to correlate with NSCLC. However, a SNP (T to G, with G the less frequent variant) identified at the fourth nucleotide in LCS6 was found in 20.3% of the NSCLC patients (FIG. 20B-20D). Supporting the hypothesis that the variant allele at this SNP is a genetic marker of increased lung cancer risk, an increased frequency of the allele was found in younger patients, in patients with a high frequency of additional cancers, and in patients with a reported family history of cancer (Table 6). However, because of the small numbers of patients in this retrospectively studied case series, firm conclusions were not drawn.

As a control, the 3'UTR of NRAS was sequenced in the same NSCLC patients to look for similar SNPs. NRAS is not associated with lung cancer but contains 9 putative LCSs. No SNPs were identified within the LCSs of the NRAS 3'UTR, supporting the idea that the identified SNP in the KRAS 3'UTR is an important change with respect to lung cancer.

TABLE 6

| | Among cancer patients | | |
|---|---|---|---|
| | Wildtype | Variant Allele | P-Value[a] |
| Cancer Type | | | |
| Adenocarcinoma | 40 (83.3%) | 8 (16.7%) | |
| Squamous | 11 (61.1%) | 7 (38.9%) | 0.096[b] |
| | 48 | 15 | |
| No. of Other Cancers | | | |
| None | 39 (88.9%) | 5 (11.1%) | |
| 1 | 12 (75.0%) | 4 (25.0%) | |
| 2 and More | 6 (54.6%) | 5 (45.4%) | 0.034[b] |
| | 57 | 14 | |
| Mean pack year for patients with 2nd cancers | 66.7 ± 36.5 | 47.4 ± 39.3 | 0.220 |
| Mean Packyear of cases | 52.8 ± 38.4 | 37.1 ± 35.2 | 0.257 |
| Cancer Onset | | | |
| <50 | 6 | 5 | |
| ≧50 | 51 | 9 | 0.034[b] |
| Family History | | | |
| Negative | 12 (100%) | 0 (0%) | |
| Positive | 19 (66.7%) | 9 (33.3%) | 0.038[b] |
| | 31 | 9 | |

Table 6: Characteristics of Yale NSCLC Patients.

[a]P-value is for t-test (continuous variables) or χ2 test (categorical variables), except where noted.
[b]P-value is for two-sided Fisher's exact test.

TABLE 7

Table 7. Alterations in KRAS 3'UTR LCSs. All LCSs in which mutations were identified in are listed here, as are the number of NSCLC patients with these mutations.

| | | Primary Lung Tumor/Adjacent Non-tumor Tissue | Primary Lung Tumor | Non-primary Lung Tumor with or without Adjacent Non-tumor Tissue | Non-cancerous Lung |
|---|---|---|---|---|---|
| LCS1 | 4th bp = A | 35 | 16 | 5 | 3 |
| | 4th bp = A/C | 6† | 1 | 11 | 0 |
| | 25th bp = G | 14 | 5 | 2 | 3 |
| | rs712 (−) = T/G | 27§ | 12 | 4 | 0 |
| | Total Patients | 41 | 17 | 6 | 3 |
| LCS9 | 20th bp = T | 37 | 15 | 6 | 1 |
| | 20th bp = T/C | 3‡ | 2 | 0 | 2 |
| | 15th bp = C | 39 | 17 | 6 | 3 |

TABLE 7-continued

Table 7. Alterations in KRAS 3'UTR LCSs. All LCSs in which mutations were identified in are listed here, as are the number of NSCLC patients with these mutations.

| | | Primary Lung Tumor/Adjacent Non-tumor Tissue | Primary Lung Tumor | Non-primary Lung Tumor with or without Adjacent Non-tumor Tissue | Non-cancerous Lung |
|---|---|---|---|---|---|
| | 15th bp = C/T | 31 | 0 | 0 | 0 |
| | 12th bp = A | 40 | 16 | 6 | 3 |
| | 12th bp = A/C | 0 | 1 | 0 | 0 |
| | Total Patients | 40 | 17 | 6 | 3 |
| LCS4 | 14th bp = C | 40 | 16 | 6 | 3 |
| | 14th bp = C/T | 1¶ | 0 | 0 | 0 |
| | Total patients | 41 | 18 | 6 | 3 |

68% of the primary lung tumors and 67% of the non-primary lung tumors examined were heterozygous at the rs712 locus in LCS1. A mutation at the fourth nucleotide of LCS1 was found in patients of both sexes and in a variety of non-small cell lung cancers types. The change at the twentieth nucleotide of LCS9 and was found in both sexes and in cancerous and non-cancerous lungs. The mutation at the twelfth base of LCS9 was seen in the adjacent tissue sample of a female, adenosquamous carcinoma patient. A mutation at the fifteenth base pair of LCS9 was found in the adjacent tissue of a female, squamous cell carcinoma patient, where as the primary lung tumor sample was normal. Lastly, there was one case of a mutation in LCS4. Both the tumor and adjacent tissue samples were heterozygous at this site.
†Only tumor sample (3 patients), only adjacent sample (3 patients).
§Tumor and adjacent samples (24 patients), only tumor sample (1 patient), only adjacent sample (2 patients).
‡Only tumor sample (2 patients), tumor and adjacent samples (1 patient). ψOnly adjacent sample.
¶Tumor and adjacent samples.

Example 4

Frequency of the Variant Allele Across Populations

To determine the allele frequencies of the SNP in the general population, a collection of genomic DNA from 2433 healthy individuals from a global set of 46 populations was used. Considerable polymorphism data already exist on these samples and can be found, along with the population descriptions in ALFRED, the ALlele FREquency Database (alfred.med.yale.edu). The results of a TaqMan assay revealed that <3% of the 4866 chromosomes tested had the G allele (variant) at the LCS6 SNP site (FIG. 24). The frequency of this allele varied across geographic populations, with "European" populations exhibiting the variant allele most frequently (7.6% of the chromosomes tested); African populations less frequently (<2.0% of chromosomes tested); and "Asian" and Native American populations infrequently (<0.4% of chromosomes tested). Of note, over 85% of the patients in the retrospective patient cohort were of European descent. It is apparent from this data that the SNP arose in Africa and is now frequently found outside of this geographic area, consistent with random genetic drift involved in the bottleneck of expansion out of Africa. The findings are also consistent with subsequent loss of the variant allele with expansion into East Asia and the Americas.

Example 5

The Variant Allele is Associated with Smoking-Induced NSCLC Risk

Two independent lung cancer case-control designs were used, referred to as the New Mexico (Table 8A, 325 patients) and the Boston (Table 8B, 3702 patients) studies, to determine the impact of the SNP on smoking-induced lung cancer. The frequency of the variant allele in the NSCLC cases in these studies was 18.8% and 18.1% respectively, not significantly different from the frequency in the lung cancer patients studied at Yale (p=0.20). While the presence of the LCS6 variant allele did not predict NSCLC risk for the entire patient cohort in either study (Table 8A and 8B), the variant allele was associated with increased NSCLC risk in smokers with less than a 41 or 40 pack-year smoking history (Table 8A and 8B, New Mexico Study odds ratio (OR)=2.3, 95% confidence interval (CI)=1.1-4.6, p=0.02, Boston Study odds ratio (OR)=1.36, 95% confidence interval (CI)=1.07-1.73, p=0.01), which are the medians in the respective populations. The ORs were adjusted for age, gender, smoking status, pack-years of smoking, and years since smoking cessation in both studies.

These findings indicate that the variant allele is a marker for increased risk of smoking-induced NSCLC in patients with less cigarette exposure, which in these studies was less than the mean smoking exposure of ~40 pack years, meaning a person has smoked the equivalent of one pack of cigarettes per day for 40 years. The finding that the variant SNP only impacts cancer risk for less cigarette exposure agrees with other studies showing a dose-dependent gene-environment interaction for smoking-induced lung cancer risk (Zhou, W. et al. Cancer Research 2002; 62: 1377-81; Zhou, W. et al. Cancer Epidemiology, Biomarkers & Prevention 2005; 14:491-6; and Liu, G. et al. Int. J. Cancer 2007, online); with higher smoking exposure any genetic predisposition is hypothesized to be overwhelmed by the extent of smoking-related damage.

TABLE 8A

Association between KRAS variant allele and non-small cell lung cancer in the New Mexico Case Control
Table 8A. Association between KRAS variant allele and non-small cell lung cancer in the New Mexico Case Control.

| Genotype | Controls (n = 325) | Cases (n = 218) | Crude OR | Adjusted OR[a] |
|---|---|---|---|---|
| TT | 280 | 177 | reference | reference |
| TG | 44 | 38 | 1.4 (0.9-2.2) p = 0.19 | 1.4 (0.8-2.3) p = 0.21 |

TABLE 8A-continued

Association between KRAS variant allele and non-small cell lung
cancer in the New Mexico Case Control
Table 8A. Association between KRAS variant allele and
non-small cell lung cancer in the New Mexico Case Control.

| GG | 1 | 3 | 4.7 (0.5-45.9) p = 0.17 | 5.3 (0.5-54.4) p = 0.17 |
|---|---|---|---|---|
| TG or GG | 45 | 41 | 1.4 (0.9-2.3) p = 0.13 | 1.5 (0.9-2.4) p = 0.13 |

| Pack-years[b] | Genotype | Controls | Cases | Crude OR | Adjusted OR[a] |
|---|---|---|---|---|---|
| <41 | TT | 171 | 57 | reference | reference |
|  | TG or GG | 24 | 18 | 2.3 (1.1-4.4) p = 0.02 | 2.3 (1.1-4.6) p = 0.02 |
| ≧41 | TT | 109 | 120 | reference | reference |
|  | TG or GG | 21 | 23 | 1.0 (0.5-1.9) p = 0.99 | 0.9 (0.5-1.8) p = 0.86 |

[a]Age, race, sex and current smoking status were adjusted in unconditional logistic regression model. P value for SNP-pack-years interaction was equal to 0.08 by likelihood ratio test.
[b]41 pack-years is the median of 543 study subjects. The result is not sensitive to different cutoffs.

TABLE 8B

Association between KRAS variant allele and non-small
cell lung cancer in the Boston Case Control
Table 8B. Association between KRAS variant allele and
non-small cell lung cancer in the Boston Case Control.

| Group | Genotype | Crude OR | p | Adjusted OR[#] | p |
|---|---|---|---|---|---|
| Overall (2205 cases vs. 1497 controls) | TT | 1.0 |  |  |  |
|  | TG + GG | 1.11 (0.93-1.32) | 0.23 | 1.17 (0.97-1.44) | 0.15 |
| Pack-years* <40 (956 cases vs. 1214 controls) | TT | 1.0 |  |  |  |
|  | TG + GG | 1.28 (1.03-1.60) | 0.03 | 1.36 (1.07-1.73) | 0.01 |
| Pack-years ≧40 (1249 cases vs. 283 controls) | TT | 1.0 |  |  |  |
|  | TG + GG | 0.85 (0.61-1.29) | 0.34 | 0.89 (0.63-1.25) | 0.49 |

* Pack-years is the median in smokers.
[#]Adjusted for age, gender, smoking status, pack-years of smoking, and years since smoking cessation (if ex-smoker)

Example 6

The LCS6 SNP Impacts KRAS Expression

Figure 13:
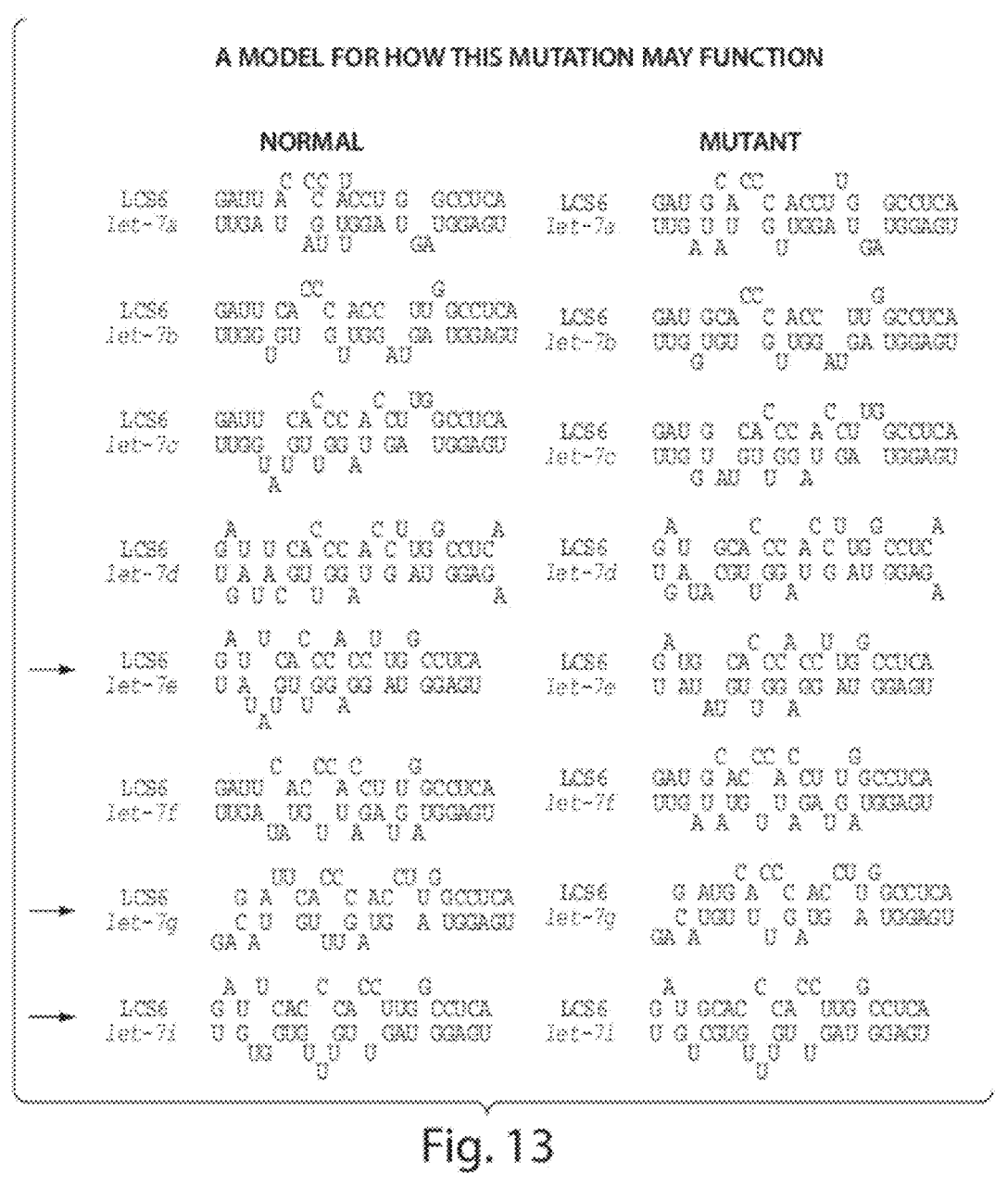

One criterion for the quality of putative miRNA binding sites is the free energy at the proposed mRNA:miRNA interaction, where the lower the free energy value, the higher the likelihood for an interaction between the miRNA and the mRNA. Based on RNAhybrid (Kruger, J. and Rehmsmeier, M. Nucleic Acids Res 2006; 34:W451-4) (bibiserv.techfak.uni-bielefeld.de/rnahybrid) values, changing the fourth nucleotide of LCS6 in the KRAS 3'UTR from a T to a G resulted in reduced free energy values for the proposed binding of each of the human let-7 sequences (FIGS. 24 and 13). These results demonstrate that the variant allele results in improved let-7 miRNA binding at this site.

To determine the effect of the LCS6 variant allele on KRAS expression, a luciferase reporter was used to represent KRAS expression (Johnson, S. M. et al. Cell 2005; 120(5):635-47). When the luciferase reporter with the alternative LCS6 (pGL3-KRASm6) was transiently transfected into HeLa S3 cells, which make abundant let-7, luciferase expression was reduced ~5-fold as compared to the unaltered reporter (p<0.0001, FIG. 22).

The KRAS gene was evaluated for common activating mutations (in codons 12, 13, and 61) in 9 of our patients carrying the variant allele and did not find any activating mutations. Unexpectedly, activated KRAS alleles were not identified among the LCS6 variant allele-carriers (as KRAS is activated in 30% of adenocarcinomas) (Rodenhuis, S. Semin Cancer Biol 1992; 3:241-7).

Example 7

The LCS6 SNP is Associated with Increased NSCLC Risk

Methods of the invention and case controlled studies were used to assess the impact of the LCS6 SNP on the occurrence and severity of non-small cell lung cancer (NSCLC). There are a documented 200,000 cases reported each year with an average 5-year survival rate of 15%. Of the 74 NSCLC cases included in this study, 15 of those individuals carried the LCS6 SNP which represents 20.3% of the population (p=0.2) (Table 1). When the odds ratio (OR) is considered (1.4-2.3), the presence of the LCS6 SNP indicates a 40%-130% increased risk of developing lung cancer (Table 1). This odds ratio was calculated from two independent case control studies with 400 and 4000 patients respectively (95% CI=1.1-4.6, p<0.02; 1.1-1.7, p<0.01).

Example 8

The LCS6 SNP is Associated with Increased Ovarian Cancer Risk

There are 25,000 documented cases of Ovarian Cancer per year, with an average 5-year survival rate of 10%. Of the 43 ovarian cancer patients included in this study, 22 of these individuals carried the LCS6 SNP, representing 51% of the cancer population (p<0.0000000001, odds ratio=6.4). Among those patients who were diagnosed with high-risk subtypes, such as the Pap serous subtype (makes up ~75 percent of epithelial ovarian cancer), 22 of the 38 individuals studied carried the LCS6 SNP, representing 58% of the high-risk ovarian cancer population (p<0.0000000001, odds ratio=8.45) (Table 1). The data of the instant study were validated using data from a set of Italian subjects (200 cases, expected prevalence of the LCS6 SNP only 8%). The LCS6 SNP was found to be present in 40% of these cases (all subtypes, OR=3.86) (all subtypes except mucinous which together make up 90% of epithelial cancers, OR=4.3) (Table 1).

Example 9

The LCS6 SNP is Associated with Increased Uterine/Endometrial Cancer Risk

There are 45,000 documented cases of uterine/endometrial cancer per year, with an average 5-year survival rate of 85% for the endometriod subtype and a significantly less average 5-year survival rate of 10% for "high risk"subtypes. Among the 25 cases of endometriod subtype cancer included in the study, only one individual was a carrier for the LCS6 SNP (p=0.04, significantly not present). Importantly, of the 21 individuals included in the study who were diagnosed with high-risk subtypes of endometrial cancer, 10 subjects were carriers for the LCS6 SNP, representing 48% of the high-risk cancer population (p=0.0004, odds ratio=10/11/280/1720=5.57) (Table 1). Of the high risk subtypes, the most serious form is the pap serous subtype. Of the 9 subjects included in this study with the pap serous subtype, 5 individuals carried the LCS6 SNP, representing 56% of this group (p=0.0001, odds ratio=5/4/280/1720=7.67) (Table 1). As such, the LCS6 SNP appears to be a marker for the most serious subtypes of endometrial cancer which lead to the worst prognosis for the individuals who carry this marker.

Example 10

The LSC6 SNP is Associated with Increased Breast Cancer Risk

There are 230,000 documented cases of breast cancer per year, with an average 5 year survival rate of 50%. The prevalence of the LCS6 SNP across all subtypes of breast cancer is about 20%, which is statistically non-significant compared to the prevalence in the general population (of non-cancerous individuals). Importantly, the prevalence of the LCS6 SNP in the high-risk Her-2$^+$ subtype (which represents about 25% of all breast cancer with worst prognosis, only 25% 5-year survival) is 25% (11 individuals of the 44 high-risk subtype patients studied carried the LCS6 SNP) (p=0.004, odds ratio=2.1) (Table 1).

Example 11

The LCS6 SNP is Associated with Increased Head and Neck Cancer Risk

There are 15,000 documented cases of head and neck cancer per year, with a 5-year average survival of 50%. Among the 21 patients studied who were diagnosed with the oropharynx subtype, 7 individuals carried the LCS6 SNP, representing 25% of the population (p=0.03, odds ratio=3.07) (Table 1).

The LCS6 SNP is found at a significantly higher prevalence than expected in head and neck cancers, and is usually associated with particular subtypes, e.g. the oropharynx subtype. Specifically, the SNP occurred in 33% of the 24 head and neck cancer patients tested (Table 1). The statistical significance of this number is indicated by a p-value of 0.011.

Example 12

The LCS6 SNP is Associated with Increased Pancreatic Cancer Risk

There are a documented 50,000 cases per year, with less than 5% of those individuals surviving more than 5-years from diagnosis. Of the 51 cases of cancer of the exocrine pancreas included in the current study, 12 individuals carried the LCS6 SNP which represents 23.5% of the pancreatic cancer study population (p=0.05) (Table 1). When the odds ratio (OR) is considered (1.2), the presence of the LCS6 SNP indicates a 20% increased risk of developing pancreatic cancer (Table 1). This odds ratio was calculated from an ongoing analysis of a case control study with 800 patients.

Example 13

The LCS6 SNP is Associated with Increased Melanoma Risk

The LCS6 SNP is found at a significantly higher prevalence than expected in melanoma. Specifically, the SNP occurred in 28.6% of the 7 melanoma patients tested, (Table 1). The statistical significance of this number is indicated by a p-value of 0.01.

Example 14

The LCS6 SNP is Associated with Increased Colon Cancer Risk

There are 108,070 documented cases of colon cancer per year with an average 5 year survival rate of 60%. The instant study included 1364 samples of adenocarcinomas. The LCS6 SNP was present in 18.3% of these samples (p<0.001, odds ratio=1.4) (Table 1).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying a subject at risk for developing cancer, comprising detecting a mutation in let-7 complementary site LCS6 of human KRAS in a patient sample, wherein the mutation is a SNP comprising a uracil (U) or thymine (T) to guanine (G) transition at position 4 of LCS6, and determining that the presence of the mutation indicates the subject has a greater risk of developing cancer.

2. A method of predicting the onset of developing cancer in a subject at risk for developing cancer, comprising detecting a mutation in let-7 complementary site LCS6 of human KRAS in a patient sample, wherein the mutation is a SNP comprising a uracil (U) or thymine (T) to guanine (G) transition at position 4 of LCS6, and determining that the presence of the mutation predicts an earlier onset of developing cancer in the subject.

3. The method of claim 1 or 2, wherein said cancer is lung cancer.

4. The method of claim 1 or 2, wherein said cancer is a lung, an ovarian, a breast, a uterine, a head and neck, a pancreatic, or a colon cancer.

5. A method of detecting a SNP in let-7 complementary site LCS6 of human KRAS, comprising assaying for the presence of a uracil or thymine to guanine transition at position 4 of LCS6 of KRAS, wherein the transition modulates the binding efficacy of a let-7 family miRNA molecule, thereby detecting a SNP in the LCS6 of human KRAS.

6. A method of determining a cancer prognosis, the method comprising assaying for the presence of a uracil or thymine to guanine transition at position 4 of let-7 complementary site LCS6 of human KRAS, whereby identifying the presence of the transition indicates a poor prognosis, thereby determining a cancer prognosis.

* * * * *